(12) United States Patent  (10) Patent No.: US 8,354,217 B2
Ichikawa et al.  (45) Date of Patent: Jan. 15, 2013

(54) SALT AND PHOTORESIST COMPOSITION CONTAINING THE SAME

(75) Inventors: Koji Ichikawa, Toyonaka (JP); Masako Sugihara, Nishinomiya (JP); Tatsuro Masuyama, Toyonaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 161 days.

(21) Appl. No.: 12/786,799

(22) Filed: May 25, 2010

(65) Prior Publication Data

US 2010/0304294 A1 Dec. 2, 2010

(30) Foreign Application Priority Data

May 28, 2009 (JP) ................................. 2009-129344

(51) Int. Cl.
G03F 7/00 (2006.01)
G03F 7/004 (2006.01)
G03F 7/028 (2006.01)
G03F 7/04 (2006.01)

(52) U.S. Cl. ..................... 430/270.1; 430/330; 430/913; 430/914

(58) Field of Classification Search ............... 430/270.1, 430/913, 914, 330
See application file for complete search history.

(56) References Cited

U.S. PATENT DOCUMENTS

| | | | |
|---|---|---|---|
| 7,749,679 B2 * | 7/2010 | Wada et al. ................ | 430/270.1 |
| 2003/0194639 A1 | 10/2003 | Miya et al. | |
| 2006/0194982 A1 | 8/2006 | Harada et al. | |
| 2007/0148592 A1 * | 6/2007 | Wada et al. ................ | 430/270.1 |
| 2008/0138742 A1 | 6/2008 | Kodama et al. | |
| 2010/0136478 A1 * | 6/2010 | Kawaue et al. ............ | 430/270.1 |
| 2010/0248149 A1 * | 9/2010 | Tsuchimura et al. ......... | 430/296 |
| 2010/0273105 A1 * | 10/2010 | Utsumi et al. ............. | 430/270.1 |

* cited by examiner

Primary Examiner — Amanda C. Walke
(74) Attorney, Agent, or Firm — Birch, Stewart, Kolasch & Birch, LLP

(57) ABSTRACT

A salt represented by the formula (I-AA):

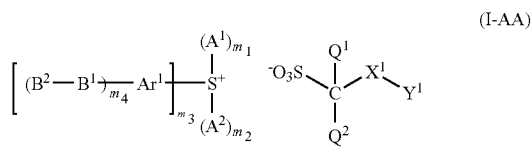

wherein $Q^1$ and $Q^2$ each independently represent a fluorine atom or a C1-C4 perfluoroalkyl group,
$X^1$ represents a single bond etc.,
$Y^1$ represents a C1-C36 aliphatic hydrocarbon group etc.,
$A^1$ and $A^2$ independently each represents a C1-C20 aliphatic hydrocarbon group etc.,
$Ar^1$ represents a $(m_4+1)$-valent C6-C20 aromatic hydrocarbon group which can have one or more substituents,
$B^1$ represents a single bond etc.,
$m_1$ and $m_2$ independently each represents an integer of 0 to 2, $m_3$ represents an integer of 1 to 3, with the proviso that $m_1$ plus $m_2$ plus $m_3$ equals 3, and $m_4$ represents an integer of 1 to 3, and a photoresist composition comprising the salt represented by the formula (I-AA) and a resin comprising a structural unit having an acid-labile group and being insoluble or poorly soluble in an aqueous alkali solution but becoming soluble in an aqueous alkali solution by the action of an acid.

10 Claims, No Drawings

SALT AND PHOTORESIST COMPOSITION CONTAINING THE SAME

This nonprovisional application claims priority under 35 U.S.C. §119(a) on Patent Application No. 2009-129344 filed in JAPAN on May 28, 2009, the entire contents of which are hereby incorporated by reference.

FIELD OF THE INVENTION

The present invention relates to a salt suitable for an acid generator and a photoresist composition containing the same.

BACKGROUND OF THE INVENTION

A chemically amplified positive resist composition used for semiconductor microfabrication employing a lithography process contains an acid generator comprising a compound generating an acid by irradiation.

US 2006/0194982 A1 discloses a photoresist composition comprising triphenylsulfonium 1-[(3-hydroxyadamantyl)methoxycarbonyl]difluoromethanesulfonate as an acid generator.

SUMMARY OF THE INVENTION

An object of the present invention is to provide a novel salt suitable for an acid generator and a photoresist composition containing the same.

The present invention relates to the followings:
<1> A salt represented by the formula (I-AA):

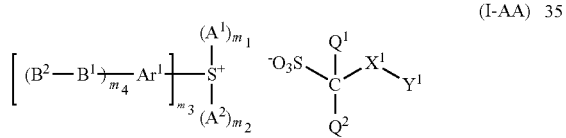

(I-AA)

wherein $Q^1$ and $Q^2$ each independently represent a fluorine atom or a C1-C4 perfluoroalkyl group, $X^1$ represents a single bond or $-(CH_2)_k-$, and one or more $-CH_2-$ in $-(CH_2)_k-$ can be replaced by $-O-$ or $-CO-$ and one or more hydrogen atoms in $-(CH_2)_k-$ can be replaced by a C1-C4 aliphatic hydrocarbon group, and k represents an integer of 1 to 17, $Y^1$ represents a C1-C36 aliphatic hydrocarbon group, a C3-C36 alicyclic hydrocarbon group or a C6-C36 aromatic hydrocarbon group, and the aliphatic hydrocarbon group, the alicyclic hydrocarbon group and the aromatic hydrocarbon group can have one or more substituents having no fluorine atom, and one or more $-CH_2-$ in the aliphatic hydrocarbon group and the alicyclic hydrocarbon group can be replaced by $-O-$ or $-CO-$, $A^1$ and $A^2$ independently each represents a C1-C20 aliphatic hydrocarbon group, a C3-C20 alicyclic hydrocarbon group or a C6-C20 aromatic hydrocarbon group, or $A^1$ and $A^2$ are bonded each other to form a C3-C20 ring, and one or more hydrogen atoms in the aliphatic hydrocarbon group, the alicyclic hydrocarbon group, the aromatic hydrocarbon group and the ring can be replaced by a hydroxyl group, a C1-C12 alkyl group, a C1-C12 alkoxy group or a C3-C36 alicyclic hydrocarbon group, $Ar^1$ represents a $(m_4+1)$-valent C6-C20 aromatic hydrocarbon group which can have one or more substituents, $B^1$ represents a single bond or C1-C6 alkylene group, and one or more $-CH_2-$ in the alkylene group can be replaced by $-O-$ or $-CO-$, $B^2$ represents a C4-C18 lactone ring group not capable of being eliminated by the action of an acid and one or more hydrogen atoms in the lactone ring group can be replaced by a cyano group, a C1-C20 aliphatic hydrocarbon group or a C3-C20 alicyclic hydrocarbon group, $m_1$ and $m_2$ independently each represents an integer of 0 to 2, $m_3$ represents an integer of 1 to 3, with the proviso that $m_1$ plus $m_2$ plus $m_3$ equals 3, and $m_4$ represents an integer of 1 to 3;

<2> The salt according to <1>, wherein $Y^1$ represents a C1-C36 aliphatic hydrocarbon group, a C3-C36 alicyclic hydrocarbon group or a C6-C36 aromatic hydrocarbon group, and one or more hydrogen atoms in the aliphatic hydrocarbon group, the alicyclic hydrocarbon group and the aromatic hydrocarbon group can be replaced by a chlorine atom, a bromine atom, a hydroxyl group, a cyano group, a C2-C7 acyl group, a C2-C18 acyloxy group, a C1-C6 alkoxy group, a C2-C7 alkoxylcarbonyl group, a C1-C12 aliphatic hydrocarbon group, a C3-C10 alicyclic hydrocarbon group or a C6-C20 aromatic hydrocarbon group, and one or more $-CH_2-$ in the aliphatic hydrocarbon group and the alicyclic hydrocarbon group can be replaced by $-O-$ or $-CO-$ and one or more hydrogen atoms in the C6-C20 aromatic hydrocarbon group can be replaced by a C1-C12 aliphatic hydrocarbon group, a C3-C10 alicyclic hydrocarbon group or a C1-C6 alkoxy group, and $Ar^1$ represents a $(m_4+1)$-valent C6-C20 aromatic hydrocarbon group and one or more hydrogen atoms in the aromatic hydrocarbon group can be replaced by a halogen atom, a hydroxyl group, a C1-C12 aliphatic hydrocarbon group, a C3-C10 alicyclic hydrocarbon group, a C2-C4 acyl group or a C1-C6 alkoxy group;

<3> The salt according to <1> or <2>, wherein $B^2$ is a group represented by the formula (B2-1a) or (B2-1b):

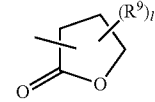

(B2-1a)

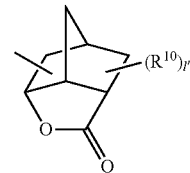

(B2-1b)

wherein $R^9$ is independently in each occurrence a C1-C20 aliphatic hydrocarbon group or a C3-C20 alicyclic hydrocarbon group, l represents an integer of 0 to 5, $R^{10}$ is independently in each occurrence a cyano group, a C1-C20 aliphatic hydrocarbon group or a C3-C20 alicyclic hydrocarbon group, and l' represents an integer of 0 to 3;

<4> The salt according to any one of <1> to <3>, wherein $Ar^1$ is a phenylene group and $m_4$ is 1;

<5> The salt according to any one of <1> to <4>, wherein $m_1$, $m_2$ and $m_3$ are 1;

<6> The salt according to any one of <1> to <5>, wherein $B^1$ is *$-O-CO-$, *$-CO-O-$, $-O-$ or *$-O-CH_2-CO-O-$ wherein * represents a binding position to $Ar^1$;

<7> The salt according to any of <1> to <6>, wherein $Ar^1$ is a p-phenylene group;

<8> A photoresist composition comprising the salt according to any one of <1> to <7> and a resin comprising a structural unit having an acid-labile group and being insoluble or poorly soluble in an aqueous alkali solution but becoming soluble in an aqueous alkali solution by the action of an acid;
<9> The photoresist composition according to <8>, wherein the photoresist composition further contains a basic compound;
<10> A process for producing a photoresist pattern comprising the following steps (1) to (5):
(1) a step of applying the photoresist composition according to <8> or <9> on a substrate,
(2) a step of forming a photoresist film by conducting drying,
(3) a step of exposing the photoresist film to radiation,
(4) a step of baking the exposed photoresist film, and
(5) a step of developing the baked photoresist film with an alkaline developer, thereby forming a photoresist pattern.

DESCRIPTION OF PREFERRED EMBODIMENTS

The salt of the present invention is a salt represented by the formula (I-AA):

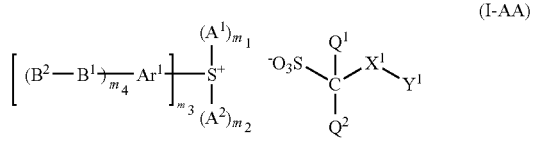

(I-AA)

wherein $Q^1$ and $Q^2$ each independently represent a fluorine atom or a C1-C4 perfluoroalkyl group,
$X^1$ represents a single bond or $-(CH_2)_k-$, and one or more $-CH_2-$ in $-(CH_2)_k-$ can be replaced by $-O-$ or $-CO-$ and one or more hydrogen atoms in $-(CH_2)_k-$ can be replaced by a C1-C4 aliphatic hydrocarbon group, and k represents an integer of 1 to 17,
$Y^1$ represents a C1-C36 aliphatic hydrocarbon group, a C3-C36 alicyclic hydrocarbon group or a C6-C36 aromatic hydrocarbon group, and the aliphatic hydrocarbon group, the alicyclic hydrocarbon group and the aromatic hydrocarbon group can have one or more substituents having no fluorine atom, and one or more $-CH_2-$ in the aliphatic hydrocarbon group and the alicyclic hydrocarbon group can be replaced by $-O-$ or $-CO-$,
$A^1$ and $A^2$ independently each represents a C1-C20 aliphatic hydrocarbon group, a C3-C20 alicyclic hydrocarbon group or a C6-C20 aromatic hydrocarbon group, or $A^1$ and $A^2$ are bonded each other to form a C3-C20 ring, and one or more hydrogen atoms in the aliphatic hydrocarbon group, the alicyclic hydrocarbon group, the aromatic hydrocarbon group and the ring can be replaced by a hydroxyl group, a C1-C12 alkyl group, a C1-C12 alkoxy group or a C3-C36 alicyclic hydrocarbon group,
$Ar^1$ represents a $(m_4+1)$-valent C6-C20 aromatic hydrocarbon group which can have one or more substituents,
$B^1$ represents a single bond or C1-C6 alkylene group, and one or more $-CH_2-$ in the alkylene group can be replaced by $-O-$ or $-CO-$,
$B^2$ represents a C4-C18 lactone ring group not capable of being eliminated by the action of an acid and one or more hydrogen atoms in the lactone ring group can be replaced by a cyano group, a C1-C20 aliphatic hydrocarbon group or a C3-C20 alicyclic hydrocarbon group, $m_1$ and $m_2$ independently each represents an integer of 0 to 2, $m_3$ represents an integer of 1 to 3, with the proviso that $m_1$ plus $M_2$ plus $m_3$ equals 3, and $m_4$ represents an integer of 1 to 3.

The salt of the present invention is preferably a salt represented by the formula (I-AA) wherein $Q^1$, $Q^2$, $X^1$, $A^1$, $A^2$, $B1$, $B^2$, $m_1$, $M_2$, $m_3$ and $m_4$ are the same as defined above, and $Y^1$ represents a C1-C36 aliphatic hydrocarbon group, a C3-C36 alicyclic hydrocarbon group or a C6-C36 aromatic hydrocarbon group, and one or more hydrogen atoms in the aliphatic hydrocarbon group, the alicyclic hydrocarbon group and the aromatic hydrocarbon group can be replaced by a chlorine atom, a bromine atom, a hydroxyl group, a cyano group, a C2-C7 acyl group, a C2-C18 acyloxy group, a C1-C6 alkoxy group, a C2-C7 alkoxylcarbonyl group, a C1-C12 aliphatic hydrocarbon group, a C3-C10 alicyclic hydrocarbon group or a C6-C20 aromatic hydrocarbon group, and one or more $-CH_2-$ in the aliphatic hydrocarbon group and the alicyclic hydrocarbon group can be replaced by $-O-$ or $-CO-$ and one or more hydrogen atoms in the C6-C20 aromatic hydrocarbon group can be replaced by a C1-C12 aliphatic hydrocarbon group, a C3-C10 alicyclic hydrocarbon group or a C1-C6 alkoxy group, and $Ar^1$ represents a $(m_4+1)$-valent C6-C20 aromatic hydrocarbon group and one or more hydrogen atoms in the aromatic hydrocarbon group can be replaced by a halogen atom, a hydroxyl group, a C1-C12 aliphatic hydrocarbon group, a C3-C10 alicyclic hydrocarbon group, a C2-C4 acyl group or a C1-C6 alkoxy group.

Examples of the C1-C6 perfluoroalkyl group include a trifluoromethyl group, a pentafluoroethyl group, a heptafluoropropyl group, a nonafluorobutyl group, an undecafluoropentyl group and a tridecafluorohexyl group, and a trifluoromethyl group is preferable. $Q^1$ and $Q^2$ each independently preferably represent a fluorine atom or a trifluoromethyl group, and $Q^1$ and $Q^2$ are more preferably fluorine atoms.

Examples of $-(CH_2)_k-$ in $X^1$ include a C1-C17 alkylene group such as a methylene group, an ethylene group, a trimethylene group, a tetramethylene group, a pentamethylene group, a hexamethylene group, a heptamethylene group, an octamethylene group, a nonamethylene group, a decamethylene group, an undecamethylene group, a dodecamethylene group, a tridecamethylene group, a tetradecamethylene group, a pentadecamethylene group, a hexadecamethylene group, a heptadecamethylene group, an isopropylene group, a sec-bytylene group and a tert-butylene group.

Examples of $-(CH_2)_k-$ in which one or more $-CH_2-$ in $-(CH_2)_k-$ are replaced by $-O-$ or $-CO-$ include $*-CO-O-X^{10}-$, $*-CO-O-X^{11}-CO-O-$, $*-X^{10}-O-CO-$, $*-X^{13}-O-X^{14}-$, $*-X^{15}-O-$ and $*-X^{10}-CO-O-$ wherein * is a binding position to $-CQ^1Q^2-$, $X^{10}$ is a single bond or a C1-C15 alkylene group, $X^{11}$ is a single bond or a C1-C13 alkylene group, $X^{13}$ is a single bond or a C1-C16 alkylene group, $X^{14}$ is a single bond or a C1-C16 alkylene group, with the proviso that total carbon numbers of $X^{13}$ and $X^{14}$ is 1 to 16, and $X^{15}$ is a single bond or a C1-C16 alkylene group. Among them, $*-CO-O-X^{10}-$, $*-CO-O-X^{11}-CO-O-$, $*-X^{10}-O-CO-$ and $*-X^{13}-O-X^{14}-$ are preferable, and $*-CO-O-X^{10}-$ is more preferable.

Examples of the aliphatic hydrocarbon group include an alkyl group such as a methyl group, an ethyl group, a propyl group, an isopropyl group, a butyl group, a sec-butyl group, a tert-butyl group, a pentyl group, a hexyl group, a heptyl group, a 2-ethyl hexyl group, an octyl group, a nonyl group, a decyl group, an undecyl group and a dodecyl group.

Examples of the alicyclic hydrocarbon group include a saturated alicyclic hydrocarbon group such as a cyclopropyl group, a cyclobutyl group, a cyclopentyl group, a cyclohexyl group, a cycloheptyl group, a cyclooctyl group, a cyclononyl group, a cyclodecyl group, a norbornyl group, a 1-adamantyl group, a 2-adamantyl group and an isobornyl group.

Examples of the aromatic hydrocarbon group include an aryl group such as a phenyl group, a naphthyl group, an anthryl group, a p-methylphenyl group, a p-tert-butylphenyl group, a p-adamantylphenyl group, a xylyl group, a qumyl group, a mesityl group, a biphenyl group, a phenathryl group, a 2,6-diethylphenyl group and a 2-methyl-6-ethylphenyl group.

Examples of the group represented by —S$^+$A$^1$A$^2$ which is formed by bonding A$^1$ and A$^2$ each other to form a C3-C20 ring, include the followings.

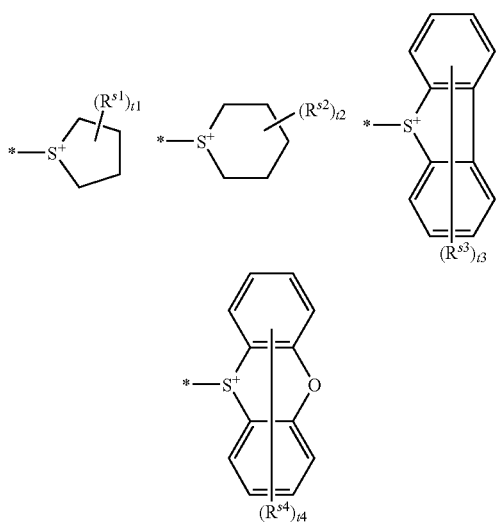

wherein R$^{s1}$, R$^{s2}$, R$^{s3}$ and R$^{s4}$ are independently in each occurrence a hydroxyl group or a C1-C12 alkyl group, t1 represents an integer of 0 to 4, t2 represents an integer of 0 to 5, t3 represents an integer of 0 to 8, and t4 represents an integer of 0 to 8.

Examples of the C4-C18 lactone ring group not capable of being eliminated by the action of an acid include a C4-C18 lactone ring group of which carbon atom bonded to B$^1$ is not a quaternary carbon atom. The lactone ring may be a monocyclic lactone ring such as γ-lactone ring and δ-lactone ring, or a polycyclic lactone ring.

Examples of the substituents of the C1-C36 aliphatichydrocarbon group, the C3-C36 alicyclic hydrocarbon group and the C6-C36 aromatic hydrocarbon group represented by Y$^1$ include a chlorine atom, a bromine atom, a hydroxyl group, a cyano group, a C2-C7 acyl group, a C2-C18 acyloxy group, a C1-C6 alkoxy group, a C2-C7 alkoxylcarbonyl group, a C1-C12 aliphatic hydrocarbon group, a C3-C10 alicyclic hydrocarbon group and a C6-C20 aromatic hydrocarbon group.

Examples of the substituents of the (m$_4$+1)-valent C6-C20 aromatic hydrocarbon group represented by Ar$^1$ include a halogen atom, a hydroxyl group, a C1-C12 aliphatic hydrocarbon group, a C3-C10 alicyclic hydrocarbon group, a C2-C4 acyl group and a C1-C6 alkoxy group.

Examples of the halogen atom include a fluorine atom, a chlorine atom, a bromine atom and an iodine atom. Examples of the acyl group include an acetyl group, a propionyl group and a butyryl group.

Examples of the acyloxy group include an acetyloxyl group, a propionyloxy group and a butyryloxy group.

Examples of the alkoxy group include a methoxy group, an ethoxy group, a propoxy group, an isopropoxy group, a butoxy group, a sec-butoxy group, a tert-butoxy group, a pentyloxy group, a hexyloxy group, a heptyloxy group, an octyloxy group, a 2-ethylhexyloxy group, a nonyloxy group, a decyloxy group, an undecyloxy group and a dodecyloxy group.

Examples of the alkoxycarbonyl group include a methoxycarbonyl group, an ethoxycarbonyl group, a propoxycarbonyl group, an isopropoxycarbonyl group, a butoxycarbonyl group, a sec-butoxycarbonyl group, a tert-butoxycarbonyl group and a pentyloxycarbonyl group. Examples of the alkyl group include a methyl group, an ethyl group, a propyl group, an isopropyl group, a butyl group, a sec-butyl group, a tert-butyl group, a pentyl group, a hexyl group, a heptyl group, a 2-ethylhexyl group, an octyl group, a nonyl group, a decyl group, an undecyl group and a dodecyl group.

It is preferred that A$^1$ and A$^2$ independently each represents the aromatic hydrocarbon group such as a phenyl group and a naphthyl group. A$^1$ and A$^2$ are more preferably phenyl groups. A$^1$ and A$^2$ can be bonded each other to form a C3-C20 ring and preferably a C4-C6 ring.

Ar$^1$ is preferably a phenylene group, and more preferably a p-phenylene group.

In B$^1$, one or more —CH$_2$— in the alkylene group can be replaced by —O— or —CO—, and B$^1$ is preferably *—O—CO—, *—CO—O—, —O— or *—O—CH$_2$—CO—O— wherein * represents a binding position to Ar$^1$.

Examples of the monocyclic lactone ring group in B$^2$ include a group represented by the formula (B2-1a):

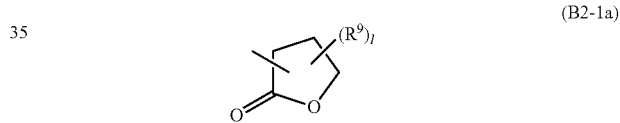

(B2-1a)

wherein R$^9$ is independently in each occurrence a C1-C20 aliphatic hydrocarbon group or a C3-C20 alicyclic hydrocarbon group and l represents an integer of 0 to 5. Examples of the polycyclic lactone ring group include a group represented by the formula (B2-1b) or (B2-1c)

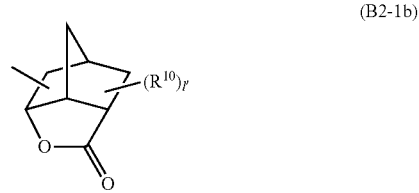

(B2-1b)

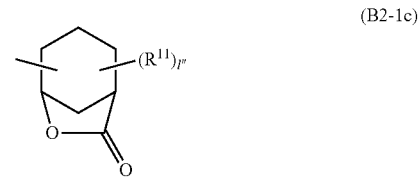

(B2-1c)

wherein R$^{10}$ is independently in each occurrence a cyano group, a C1-C20 aliphatic hydrocarbon group or a C3-C20 alicyclic hydrocarbon group, l' represents an integer of 0 to 3, R$^{11}$ is independently in each occurrence a cyano group, a C1-C20 aliphatic hydrocarbon group or a C3-C20 alicyclic hydrocarbon group, and l" represents an integer of 0 to 3, and the group represented by the formula (B2-1b) is preferable.

In the formula (I-AA), $m_1$, $m_2$ and $m_3$ are preferably 1.

$Y^1$ is preferably a C3-C36 alicyclic hydrocarbon group which can have one or more substituents selected from the group consisting of a hydroxyl group, a C2-C4 acyl group, a C1-C6 alkoxy group and a C1-C12 aliphatic hydrocarbon group. Examples of $Y^1$ include groups represented by the formulae (W1) to (W24):

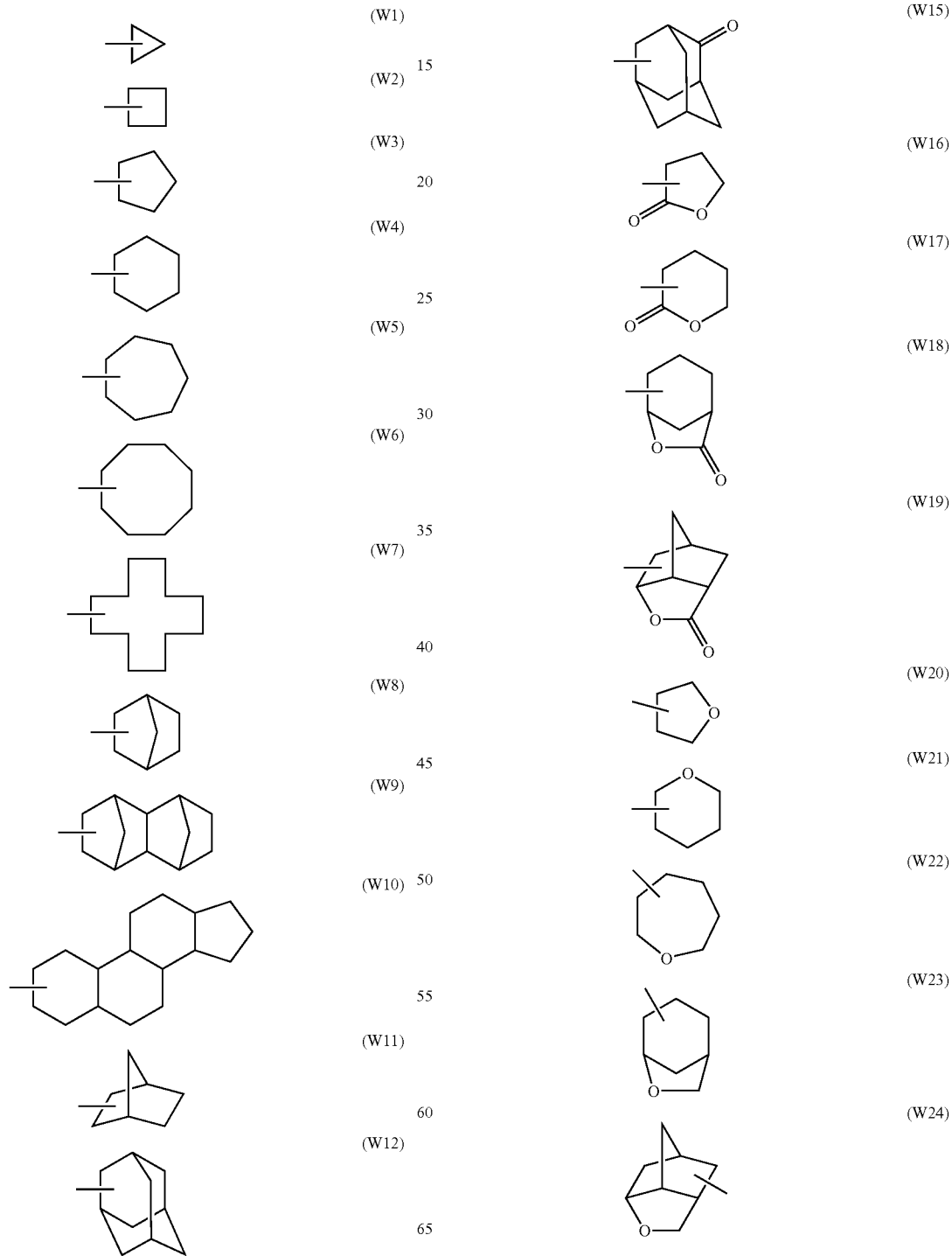

The above-mentioned groups represented by the formulae (W1) to (W19) can have one or more substituents. Among them, groups represented by the formulae (W1) to (W19) are preferable, and groups represented by the formulae (W12), (W15), (W16) and (W19) are more preferable.
Examples of the anion part of the salt represented by the formula (I-AA) include the followings.
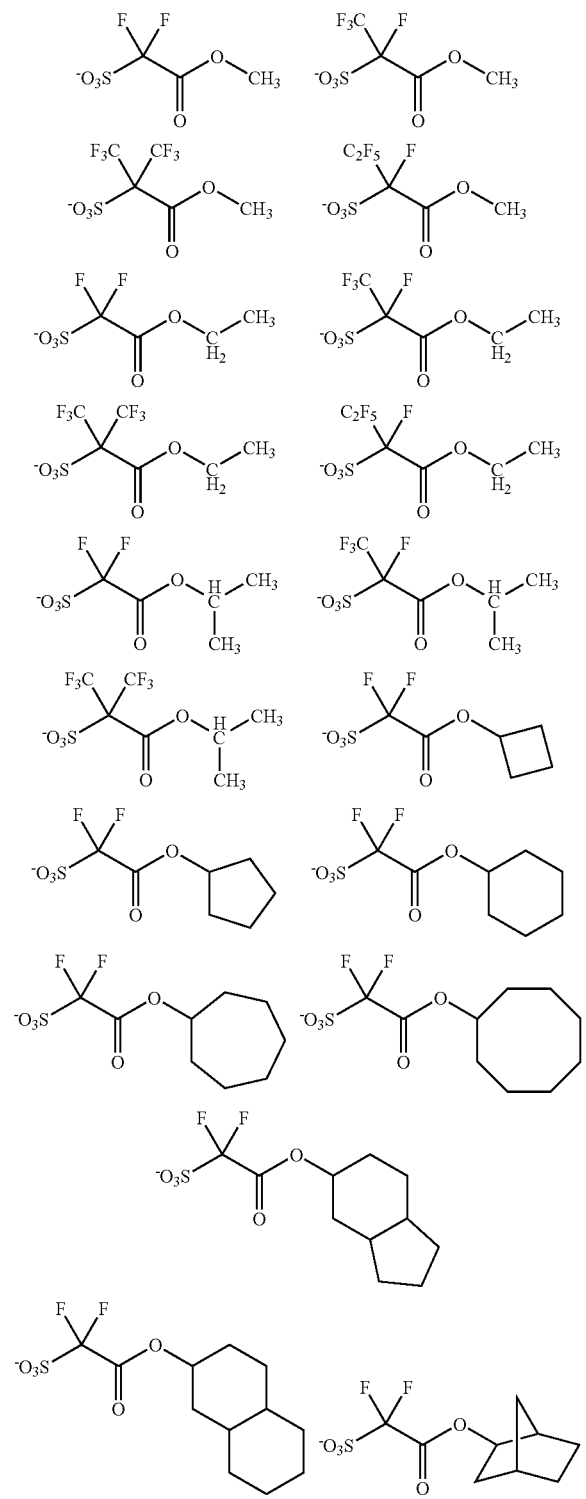
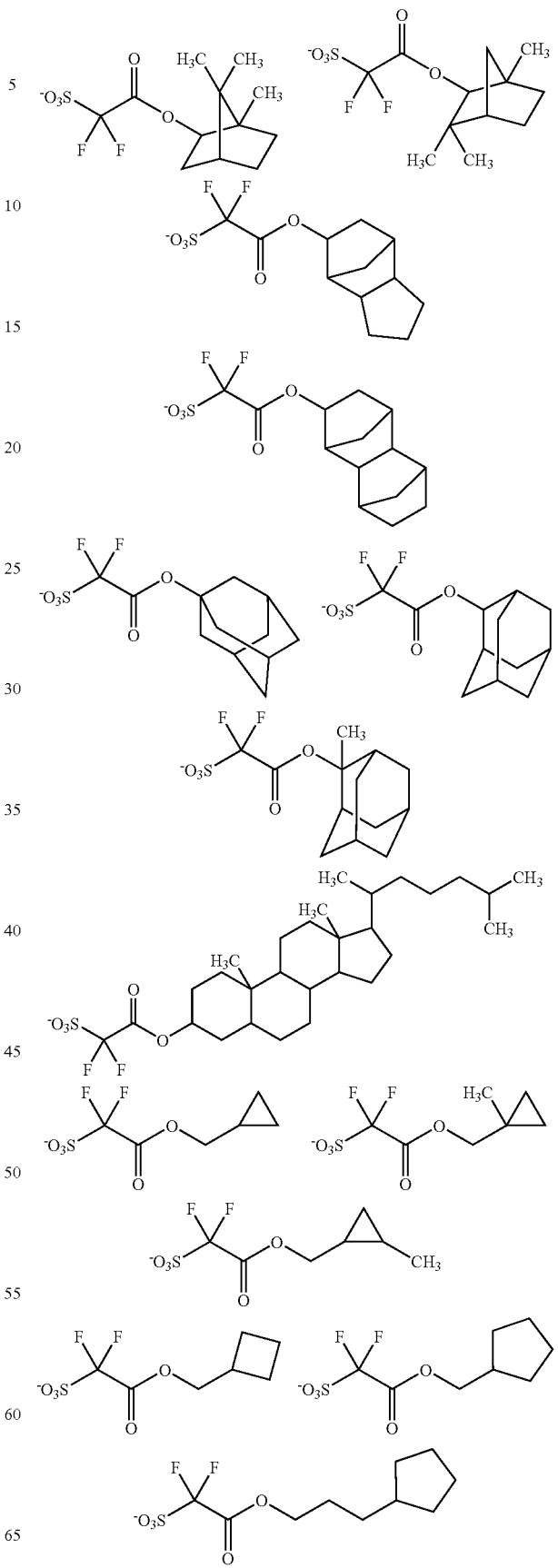

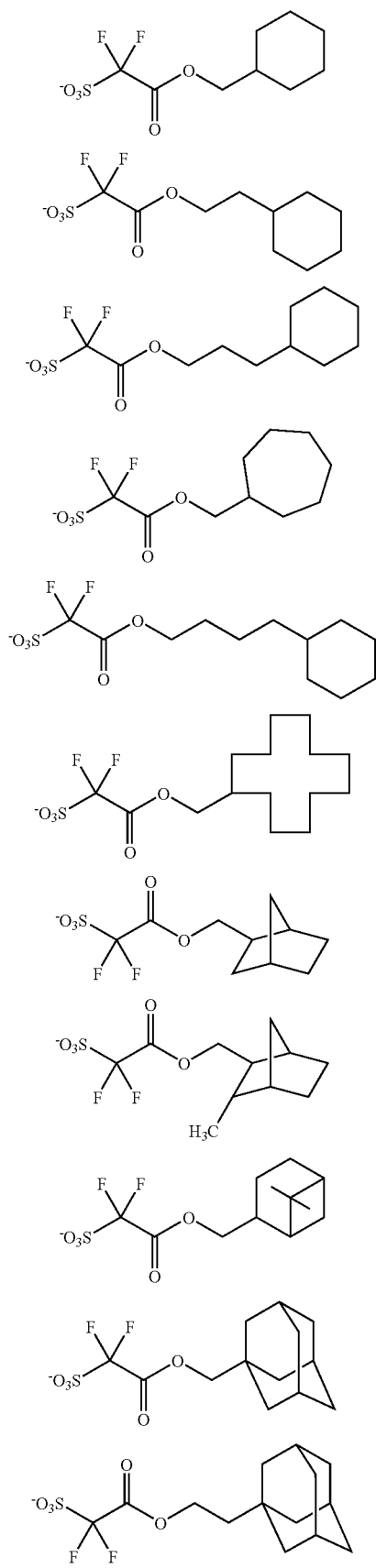
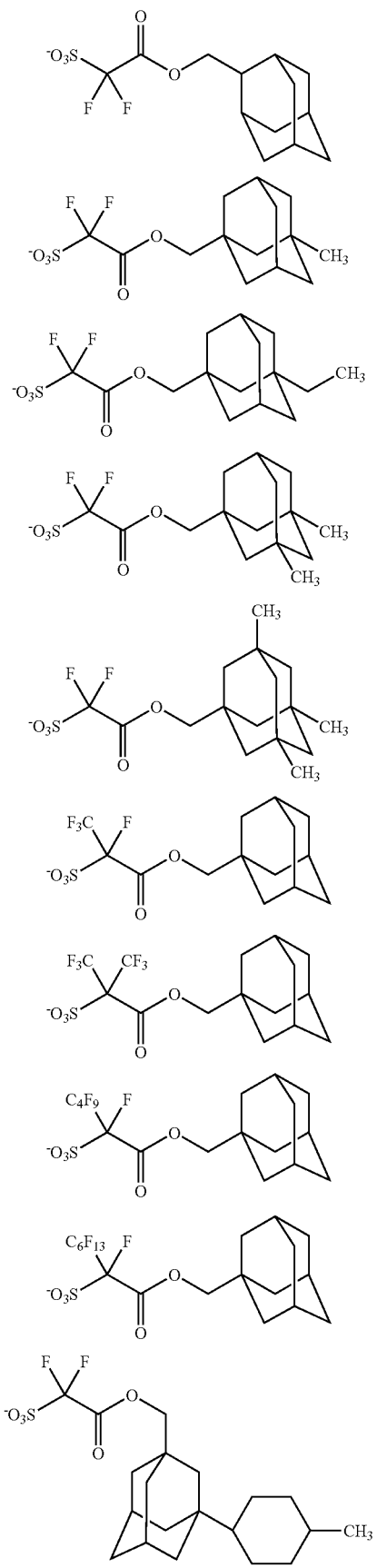

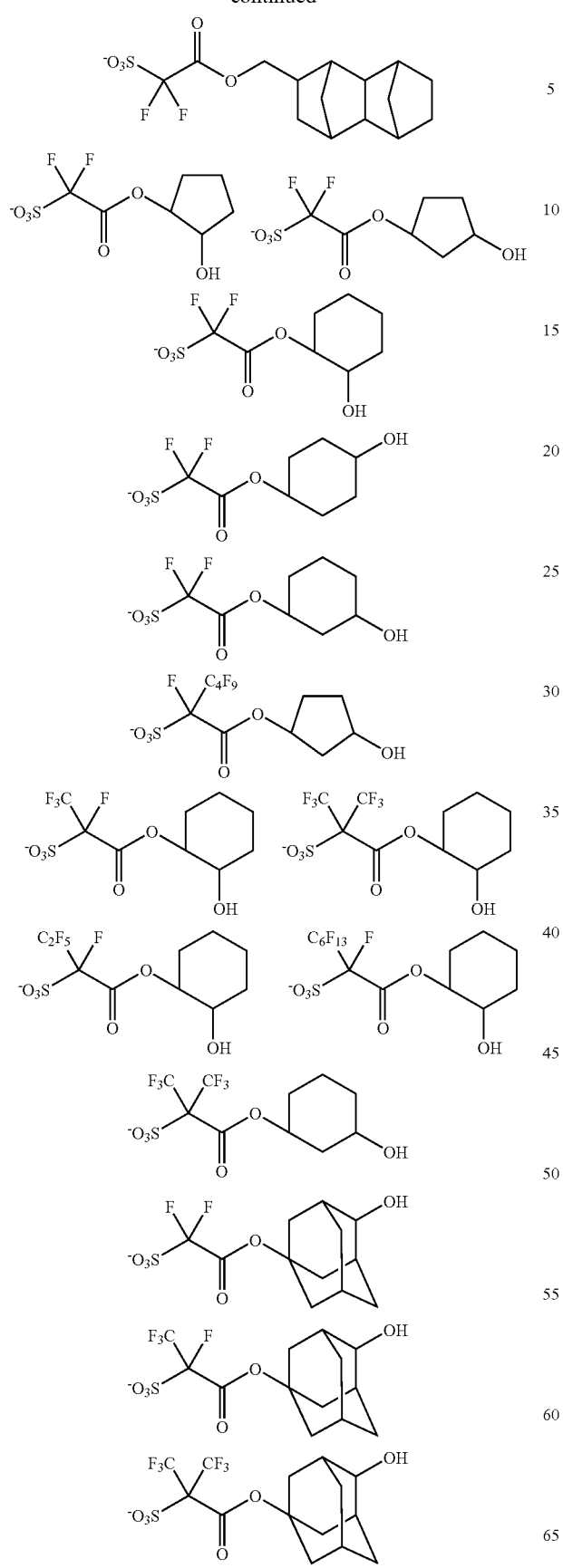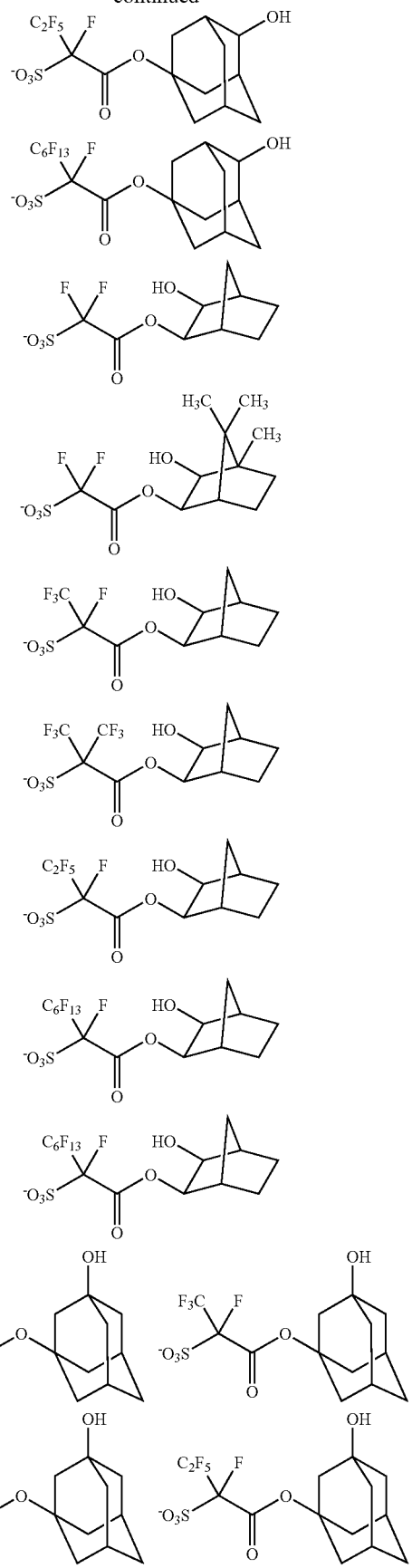

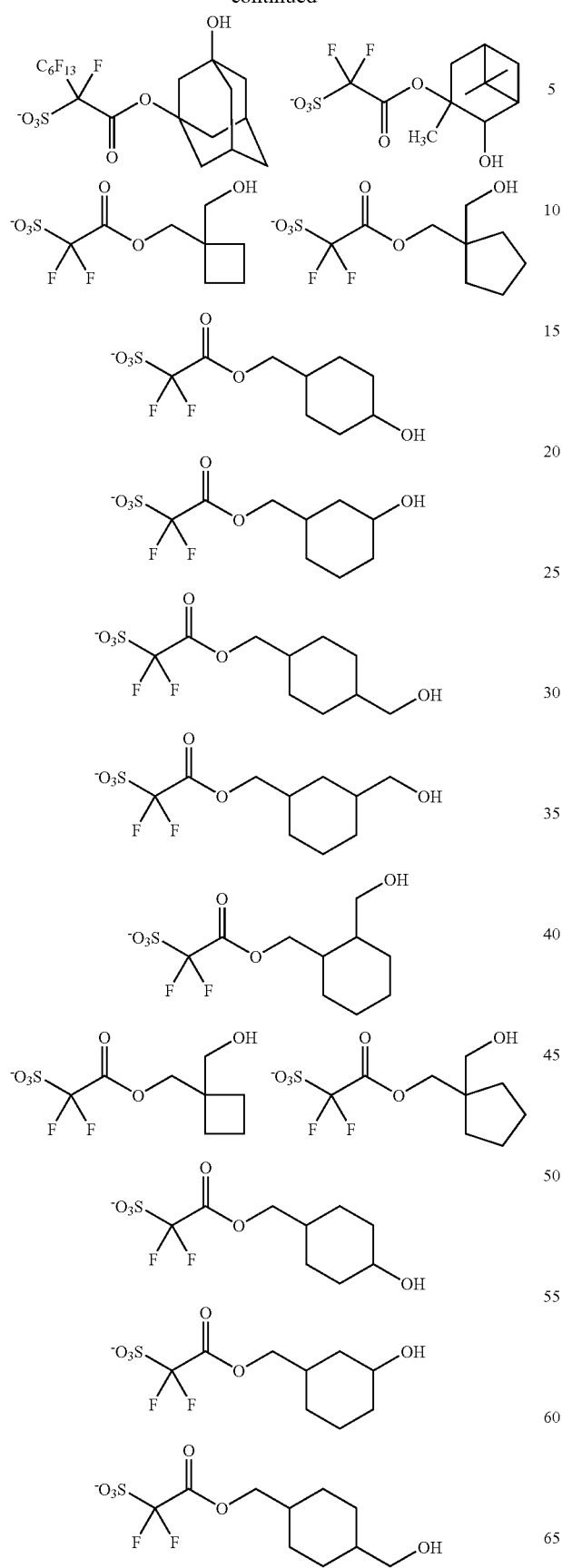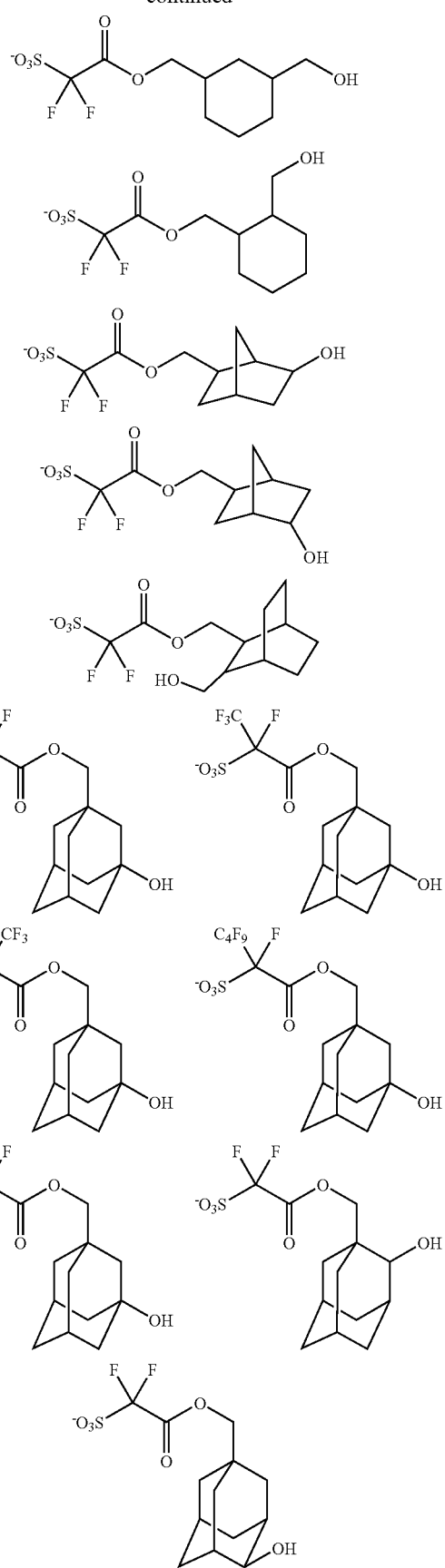

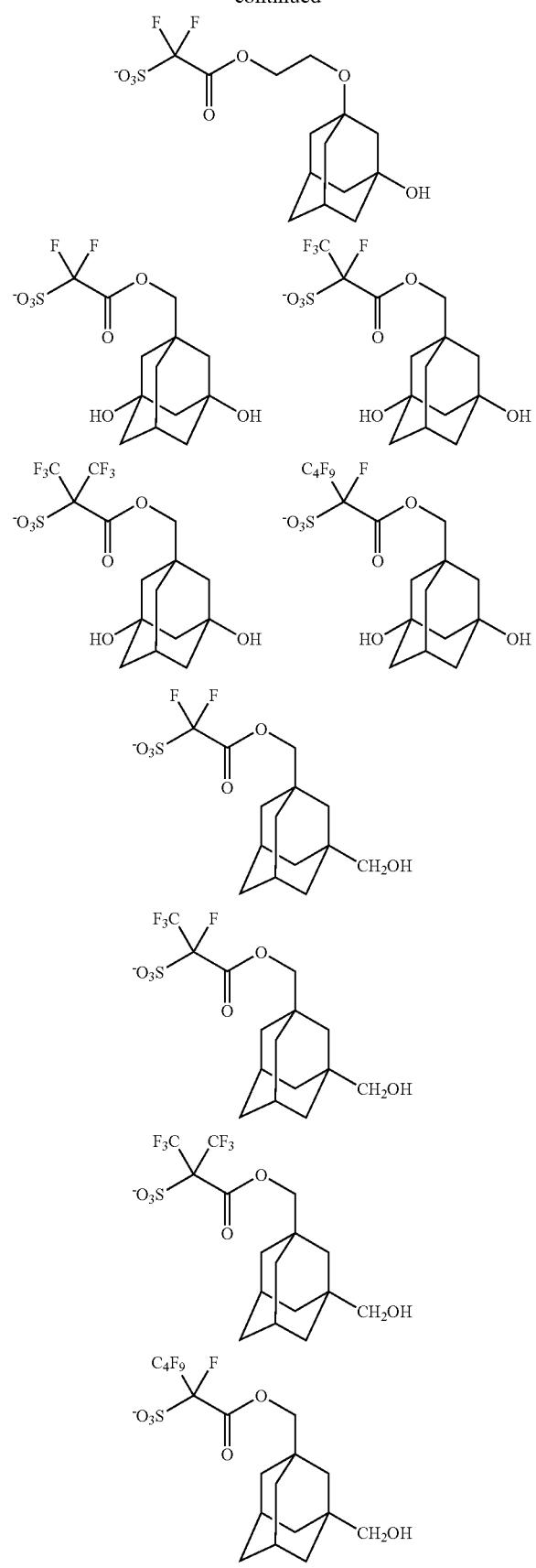
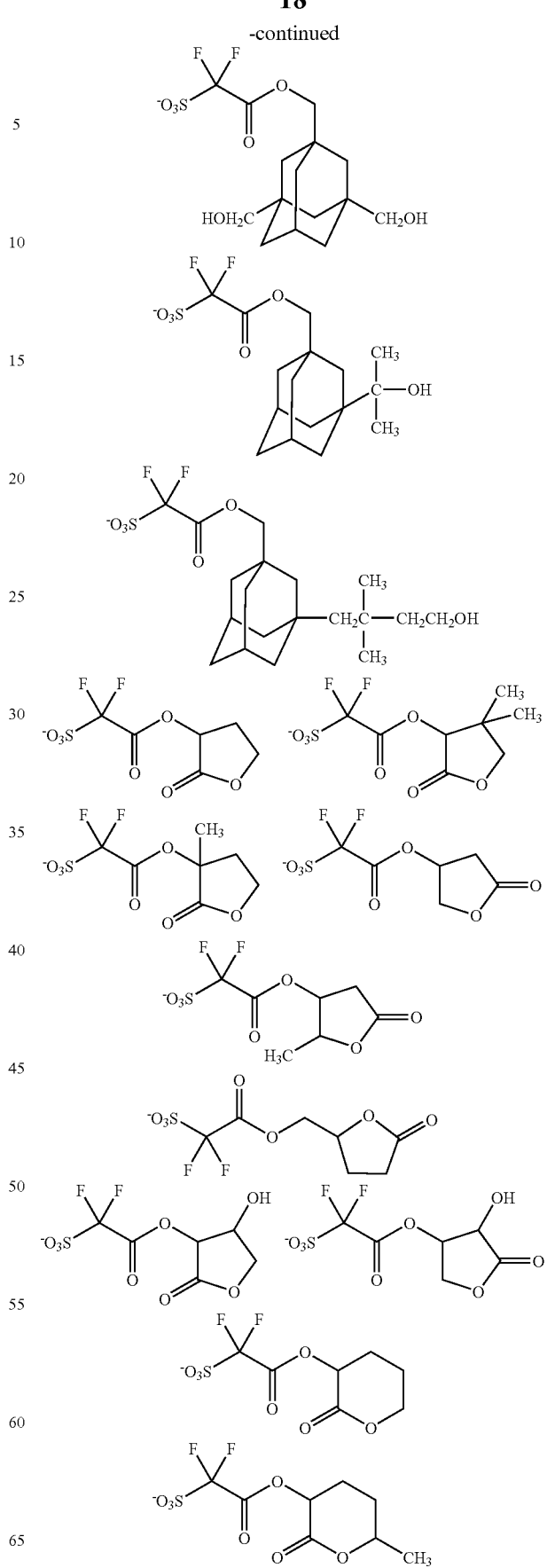

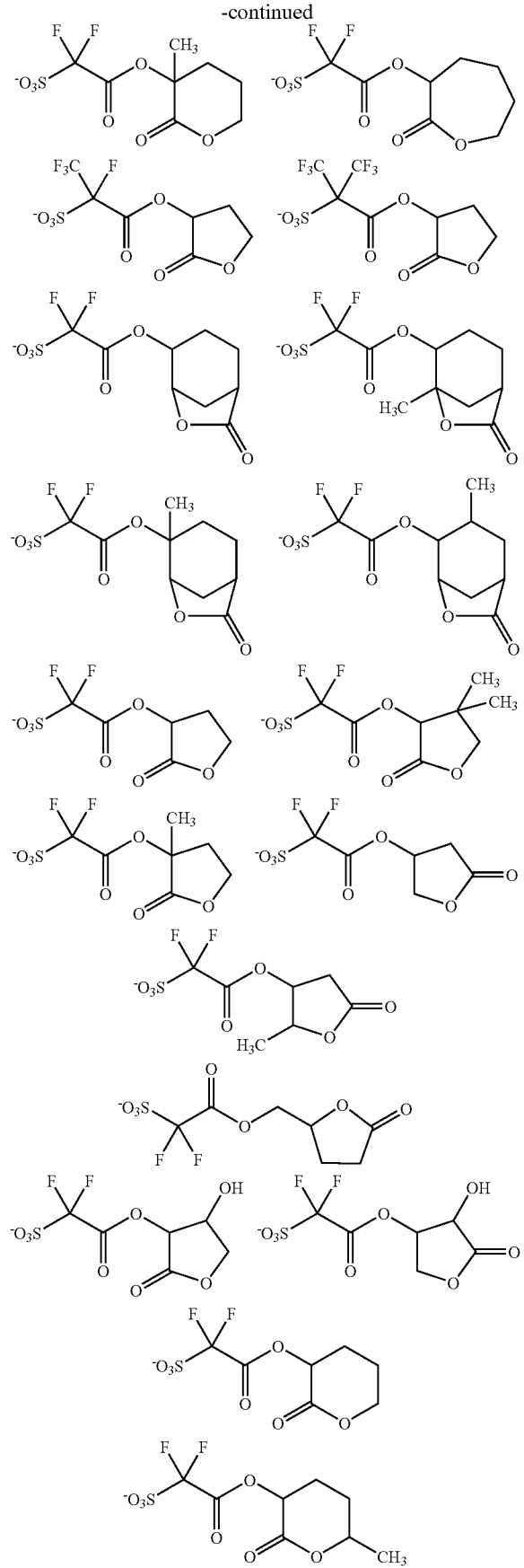
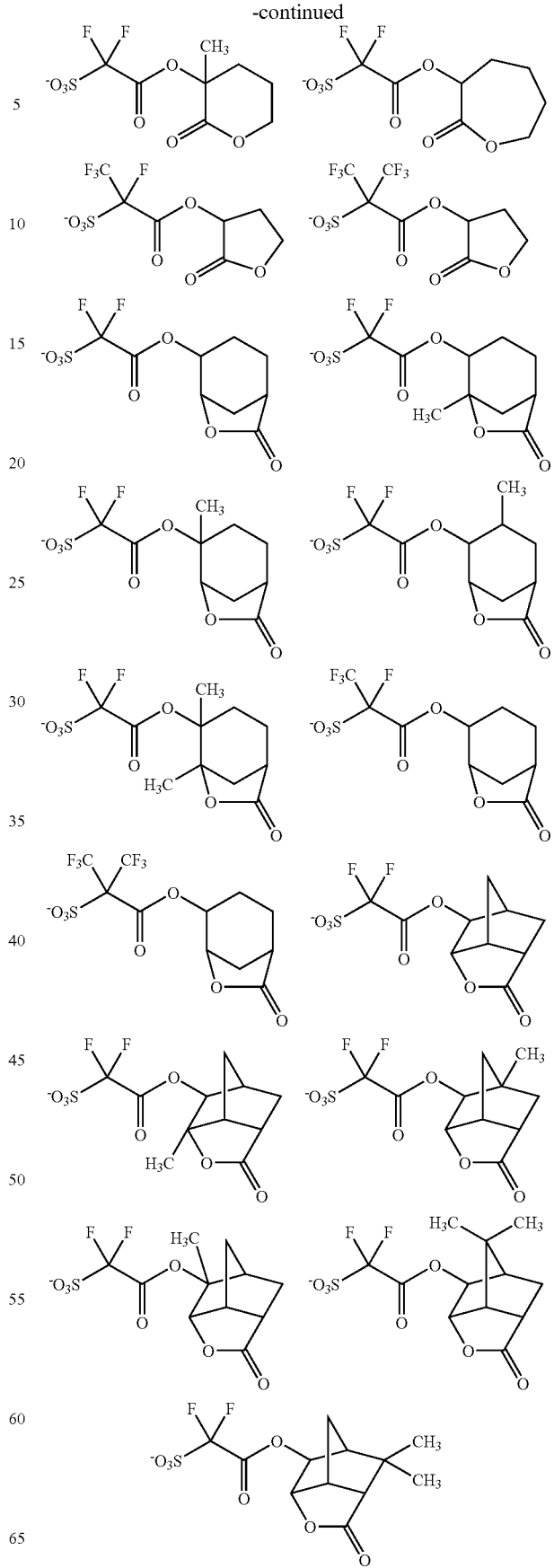

-continued
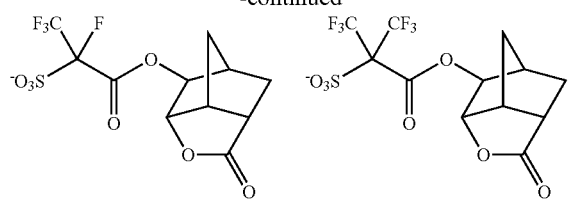
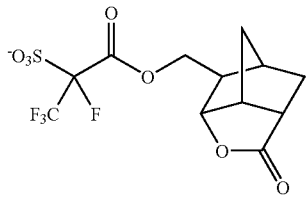
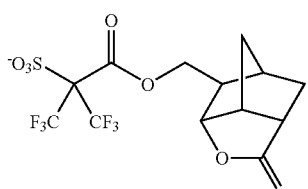
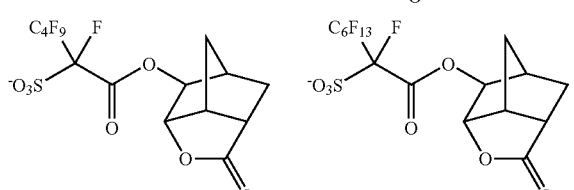
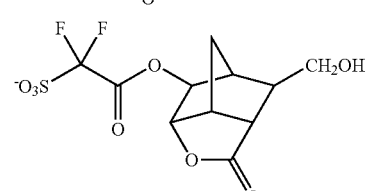
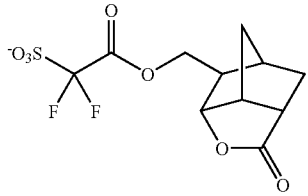
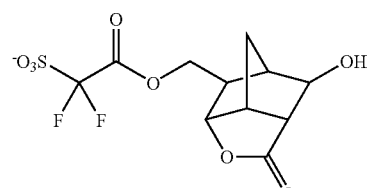
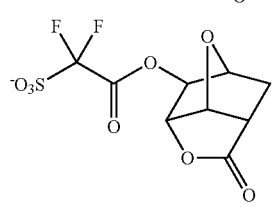
-continued
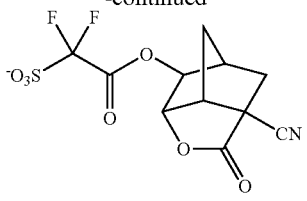
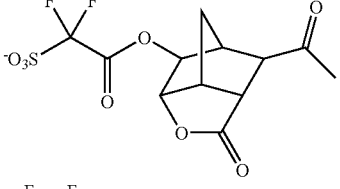
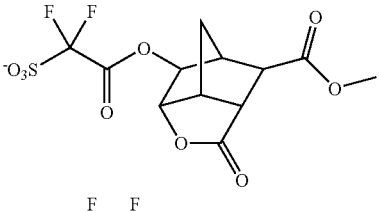
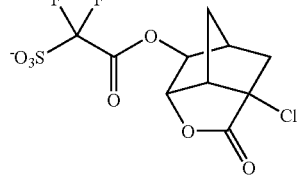
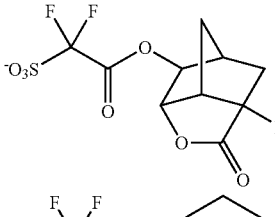
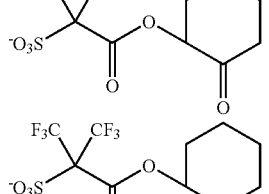
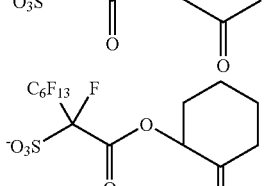
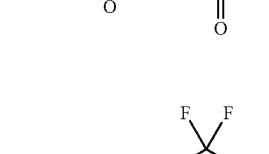
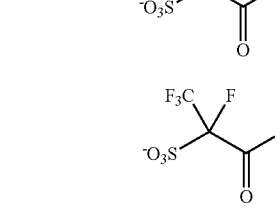

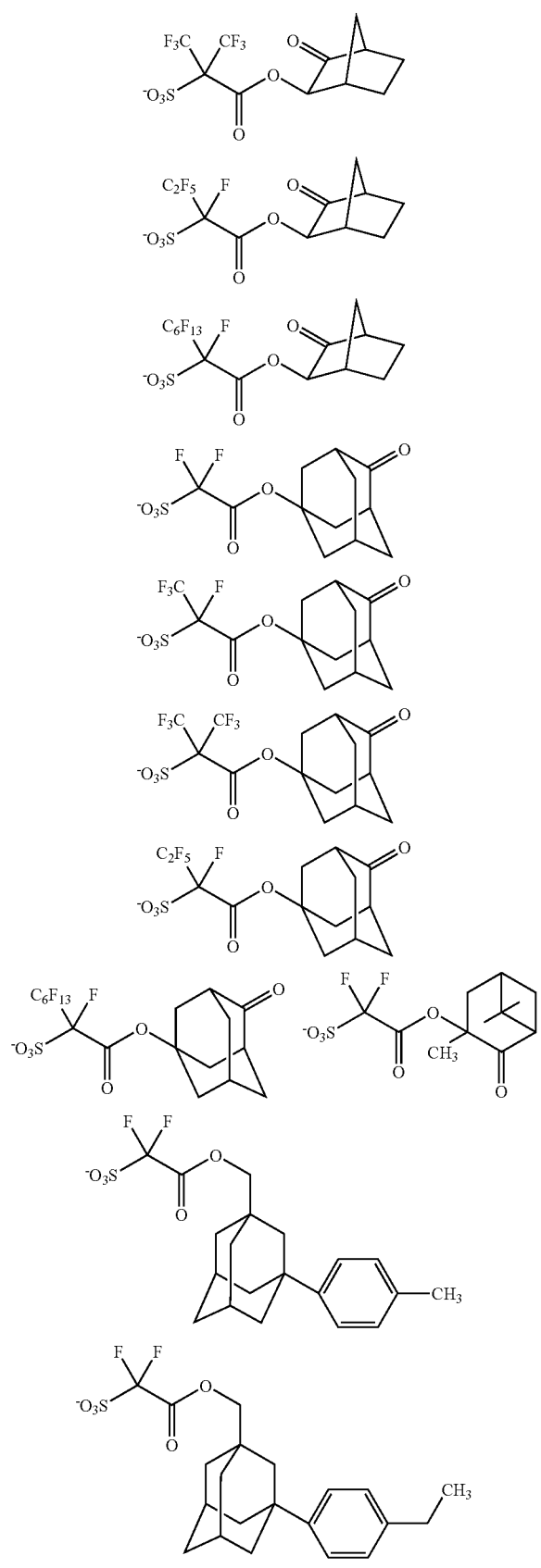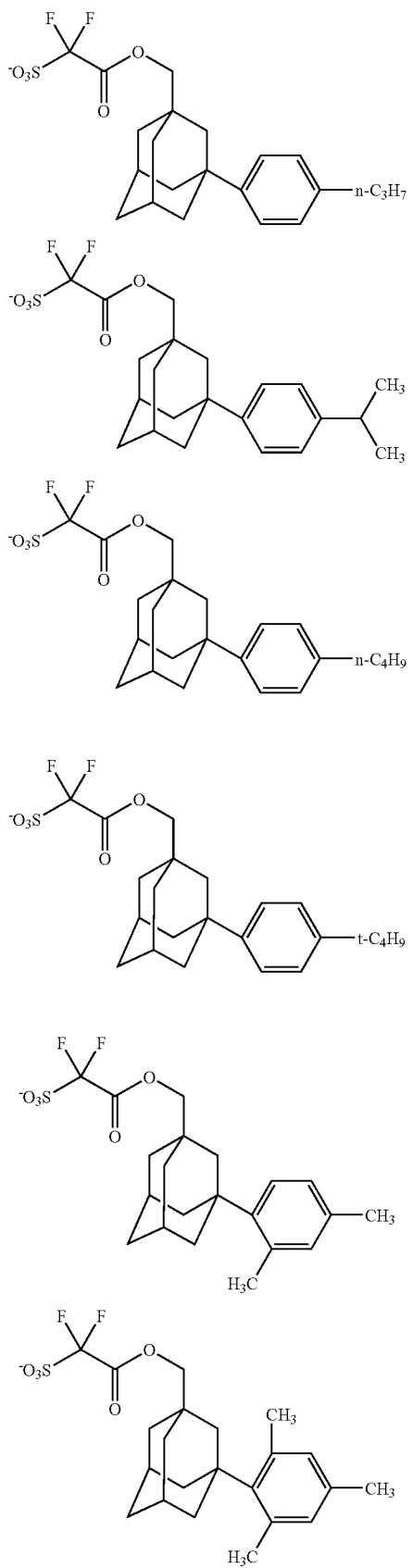

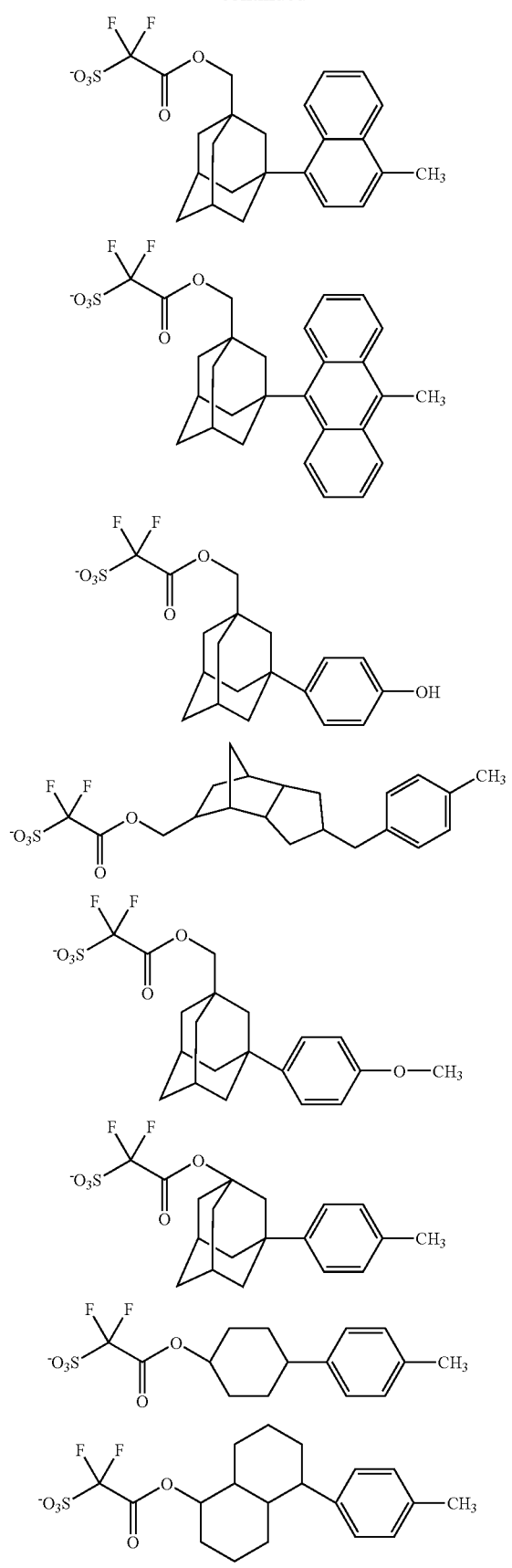
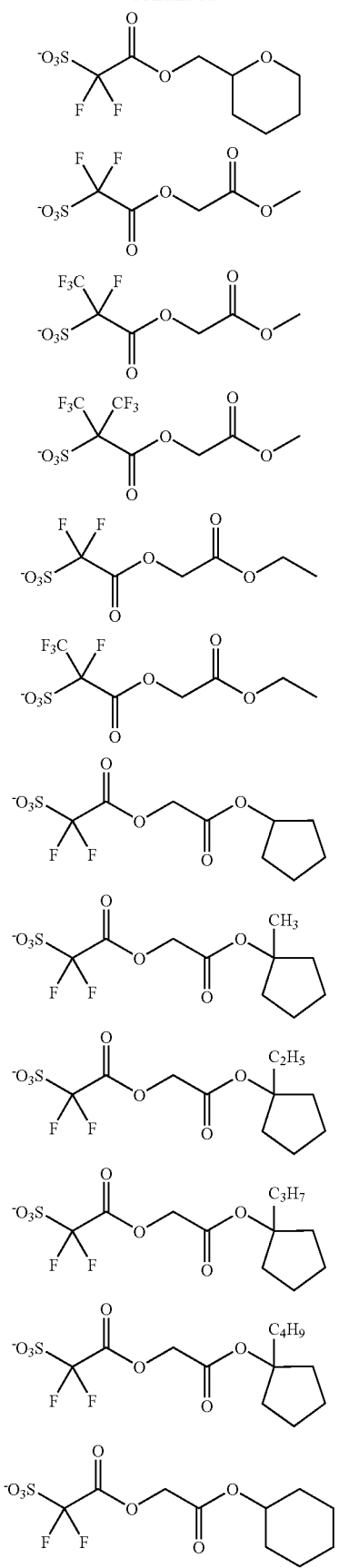

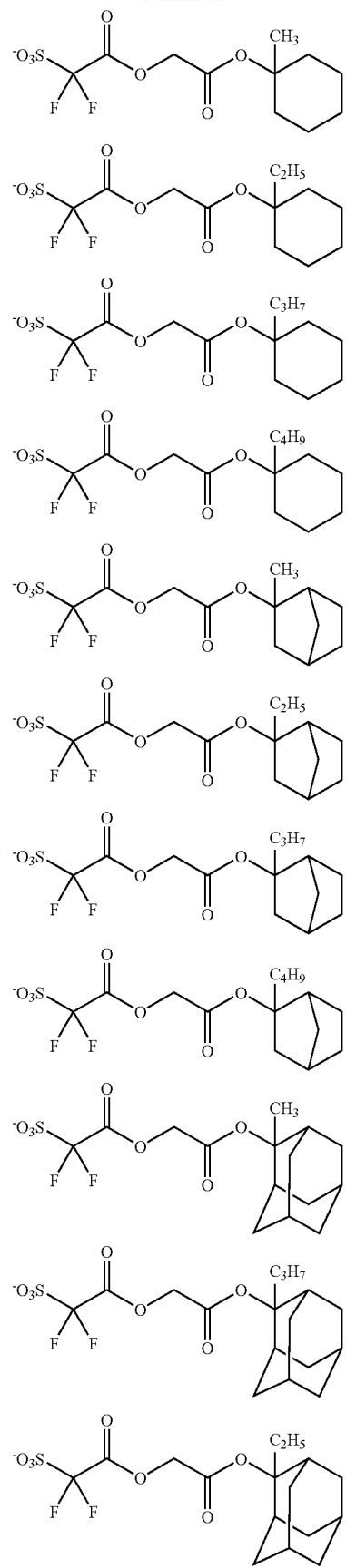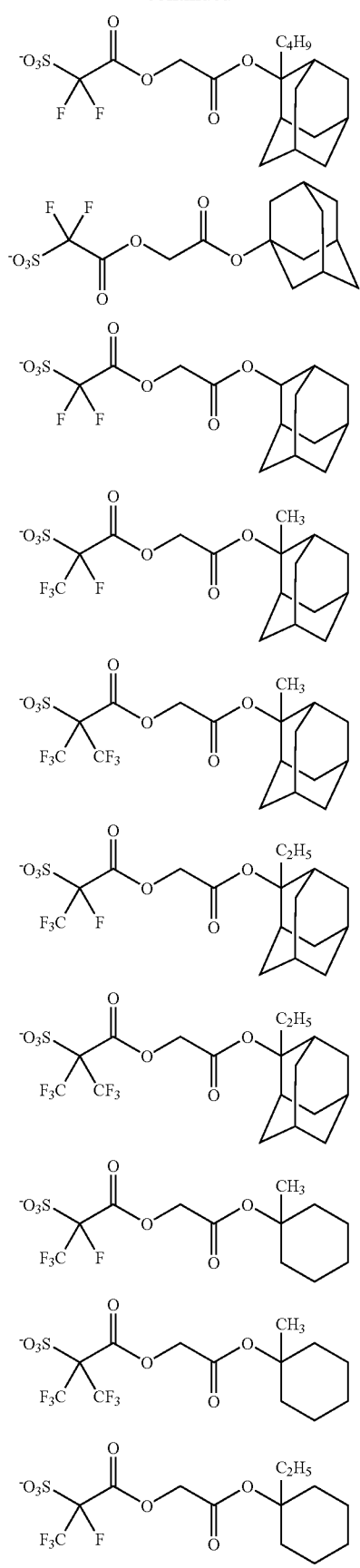

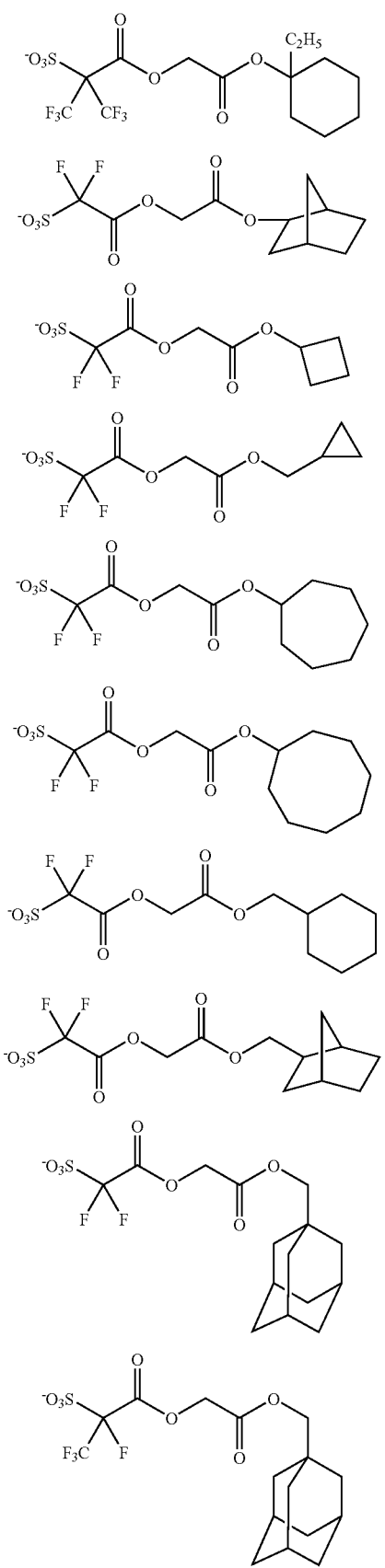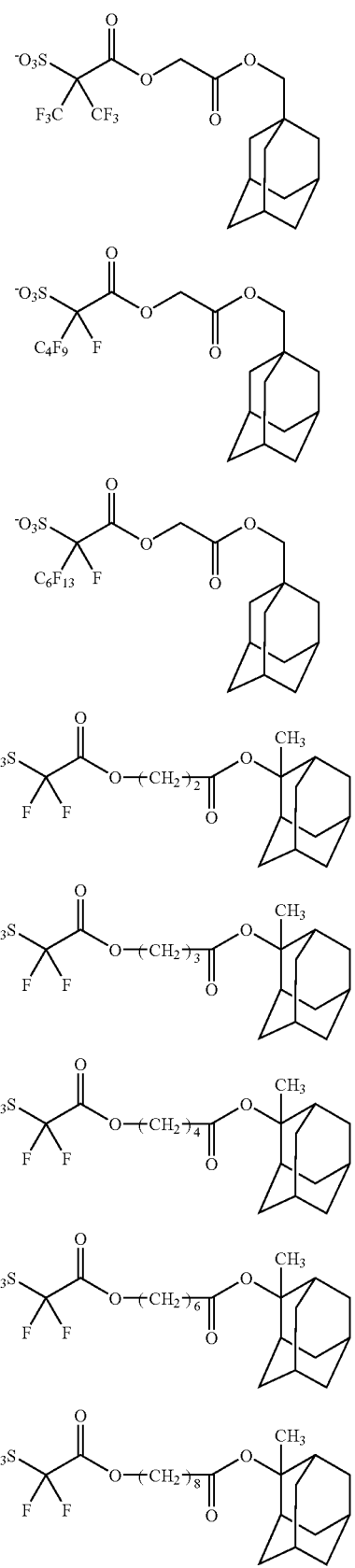

31
-continued
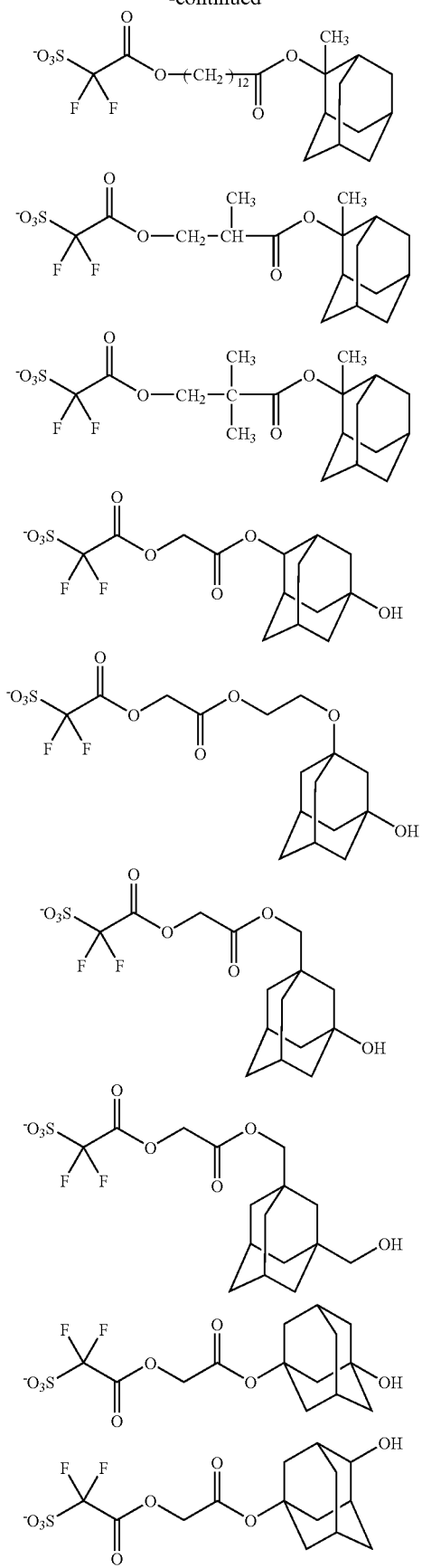
32
-continued
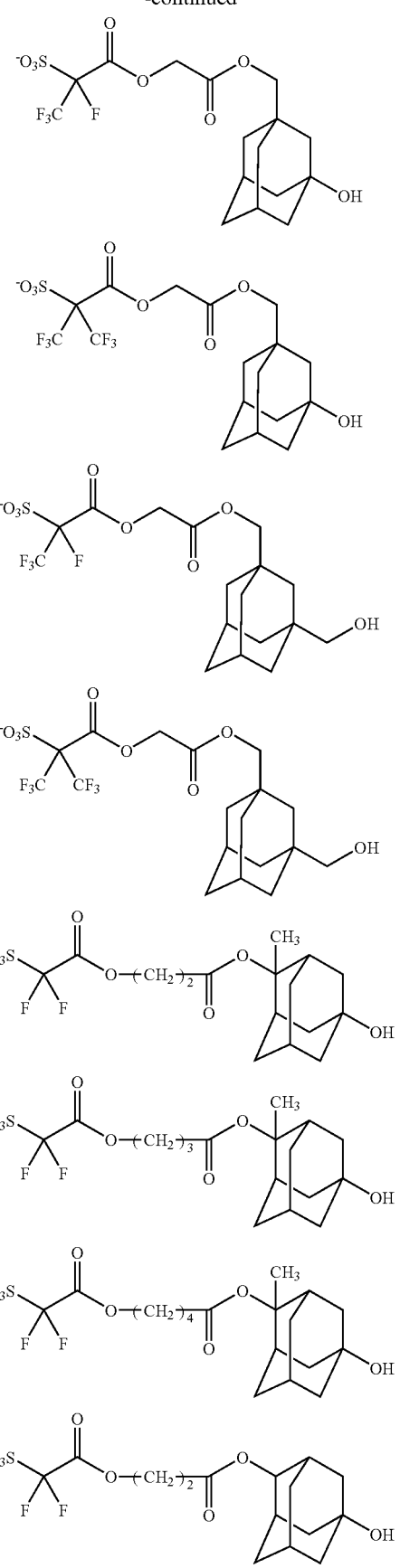

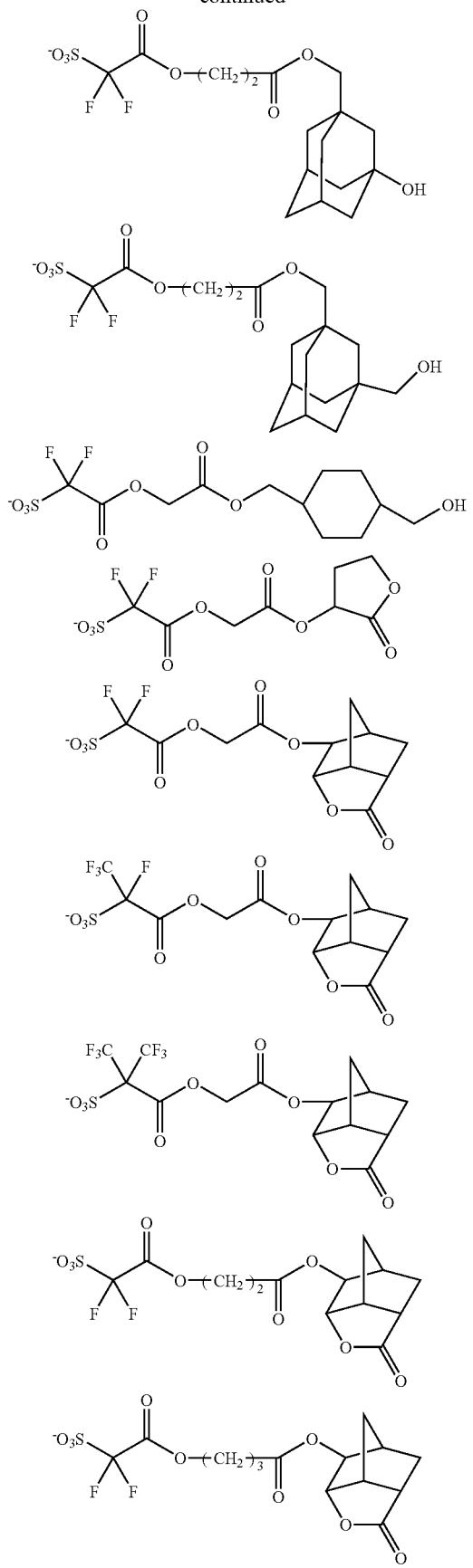
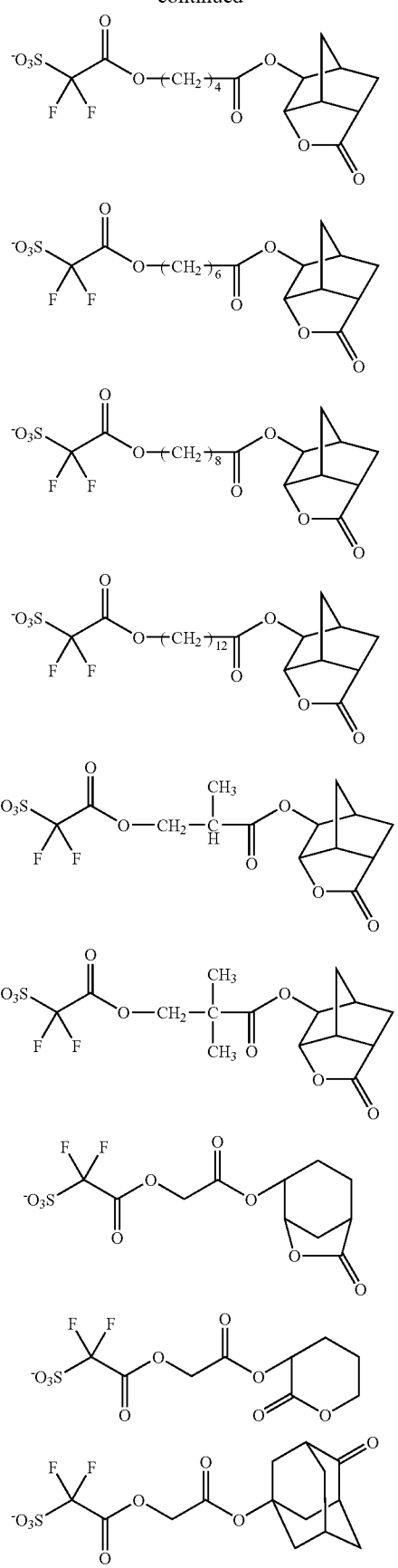

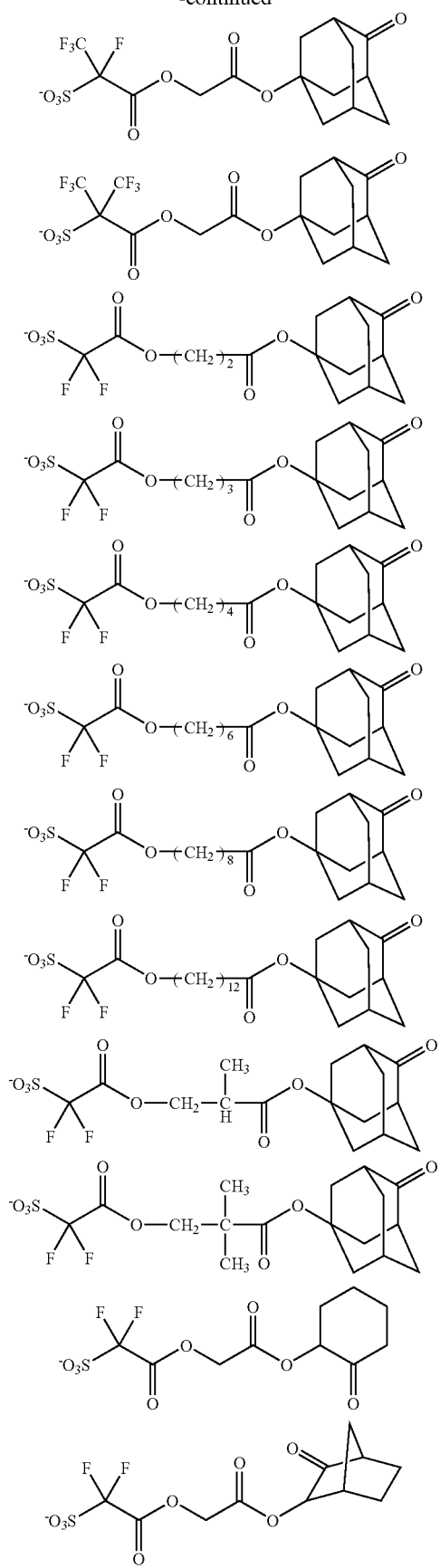
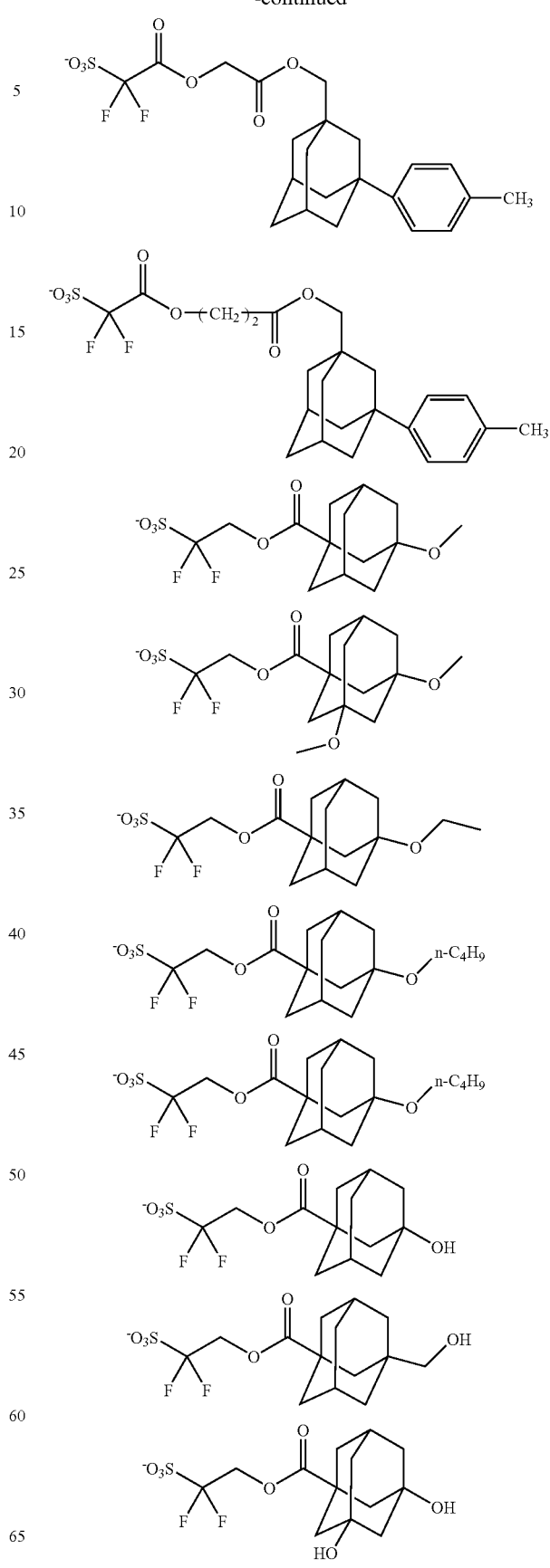

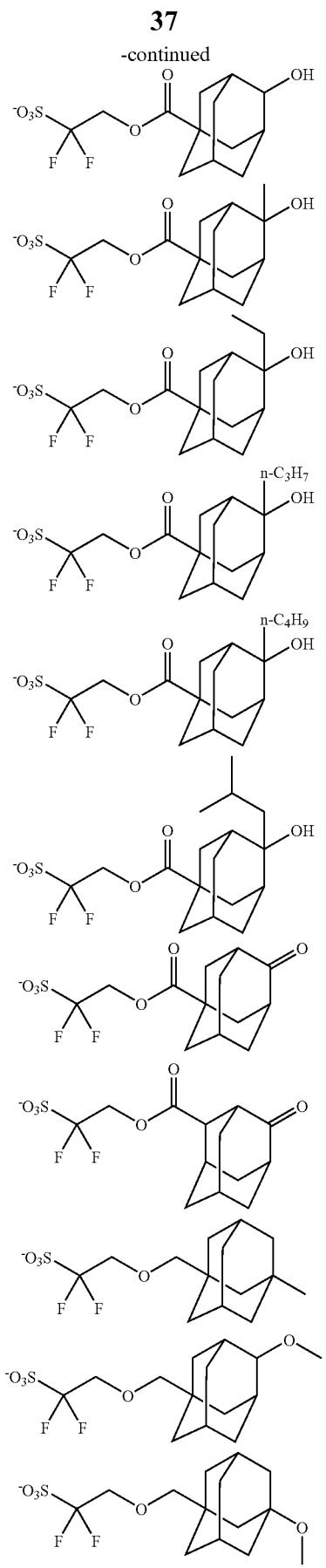
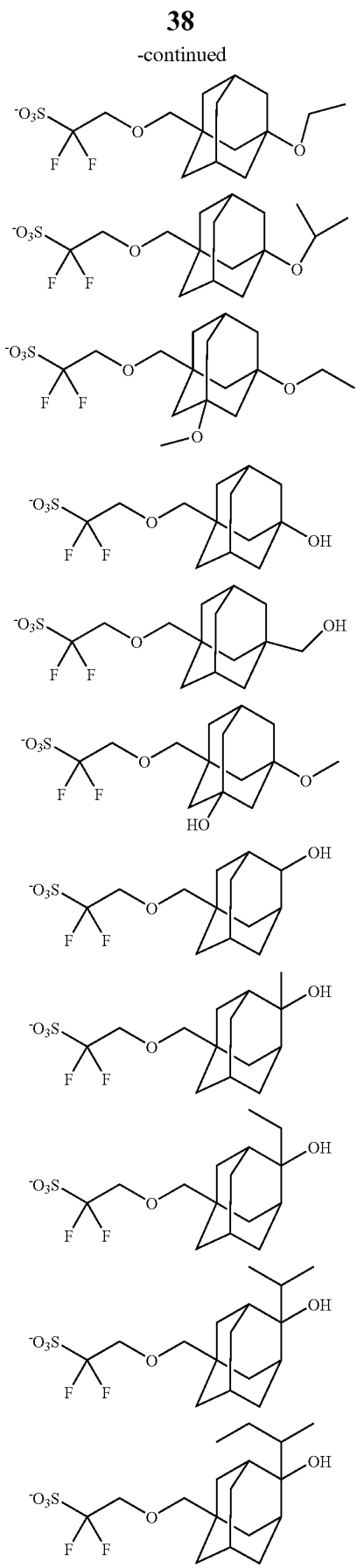

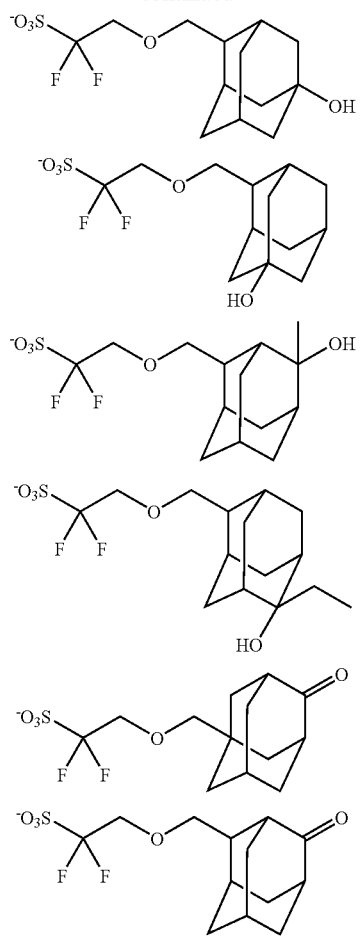

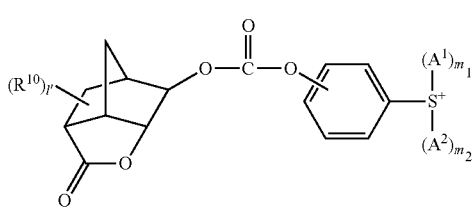

wherein $A^1$, $A^2$, $R^9$, $R^{10}$, $m_1$, $m_2$, l and l' are the same as defined above. Among them, the following cation parts represented by the formulae (AA-a2-1), (AA-a2-2), (AA-b2-1) and (AA-b2-2):

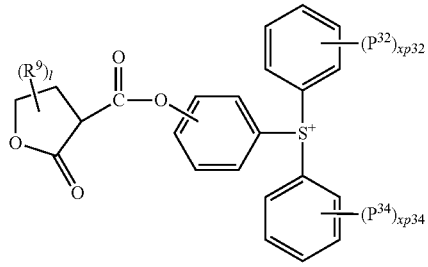

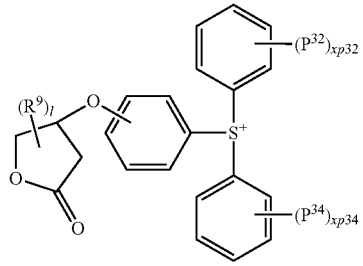

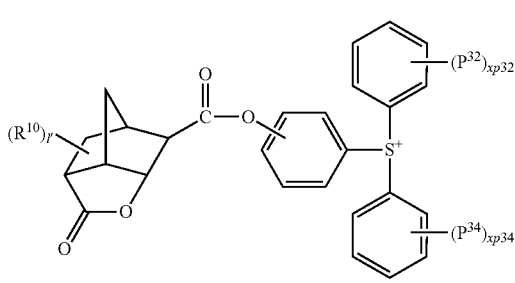

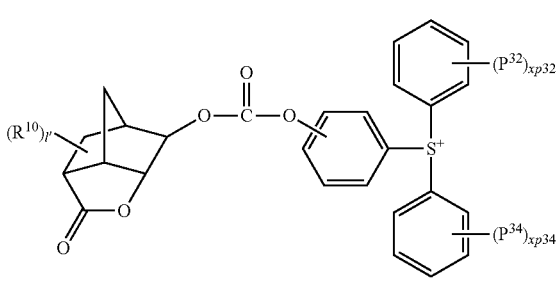

Examples of the cation part of the salt represented by the formula (I-AA) include the following cation parts represented by the formulae (AA-a1-1), (AA-a1-2), (AA-b1-1) and (AA-b1-2):

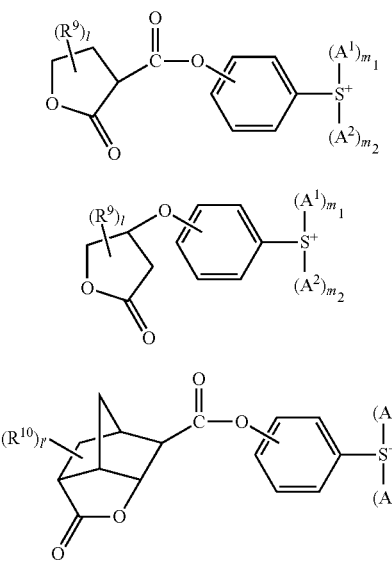

wherein $R^9$, $R^{10}$, l and l' are the same as defined above, $P^{32}$ and $P^{34}$ are independently in each occurrence a hydrogen atom, a hydroxyl group, a C1-C12 alkyl group, a C1-C12 alkoxy group or a C4-C36 alicyclic hydrocarbon group, and xp32 and xp34 independently each represents an integer of 0 to 5, are preferable.

The following cation parts represented by the formulae (AA-a3-1), (AA-a3-2), (AA-b3-1) and (AA-b3-2):

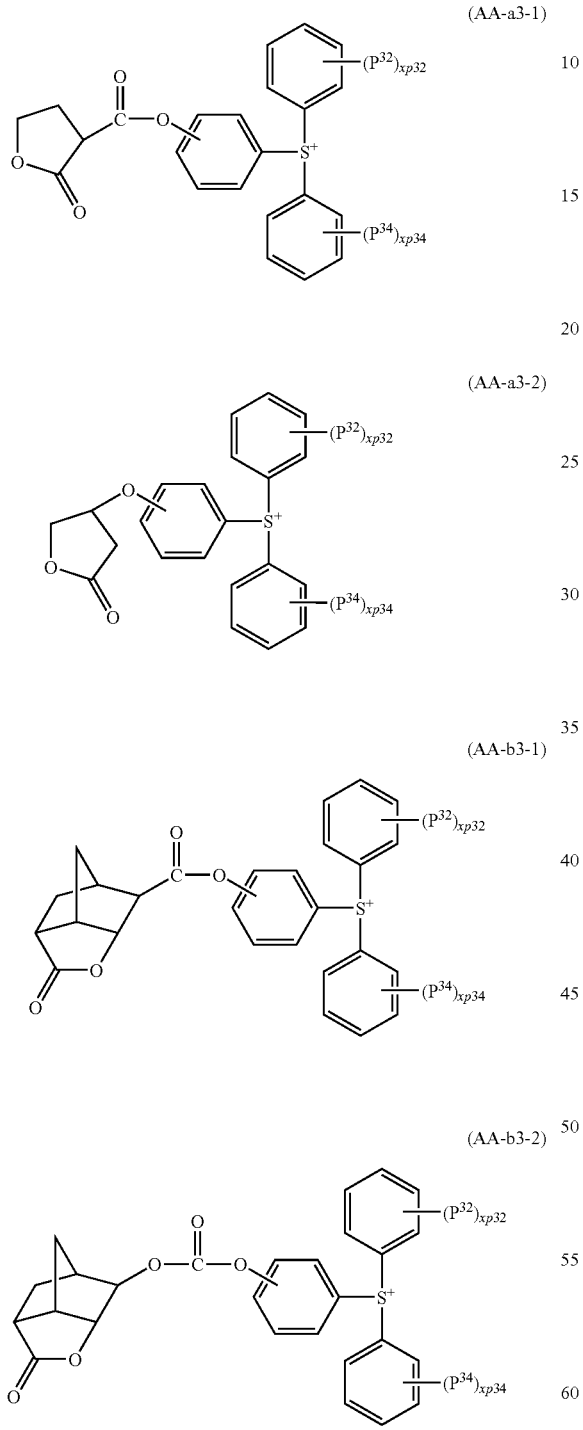

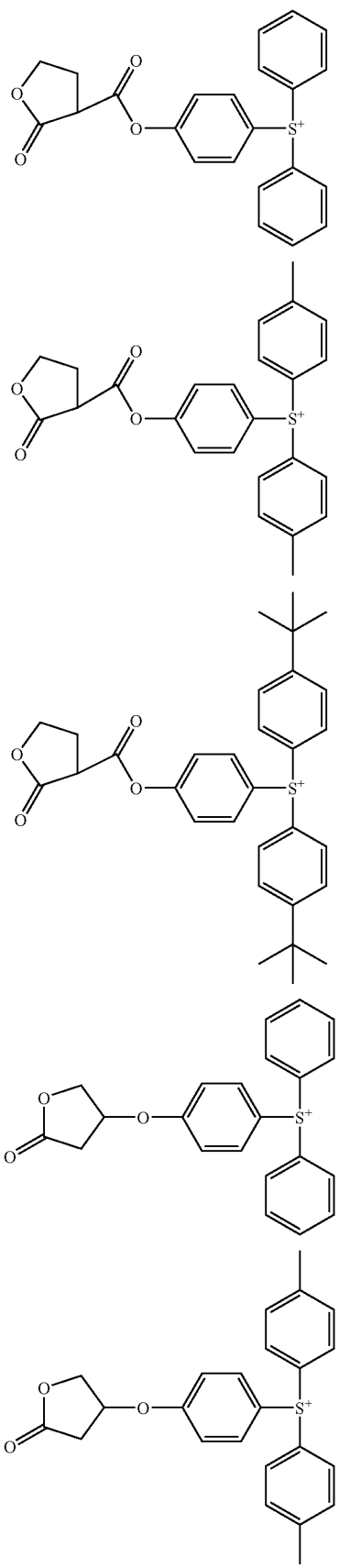

wherein $P^{32}$, $P^{34}$, xp32 and xp34 are the same as defined above, are more preferable. In the above formulae, xp32 and xp34 are preferably 0 or 1.

Specific examples of the cation part include the followings.

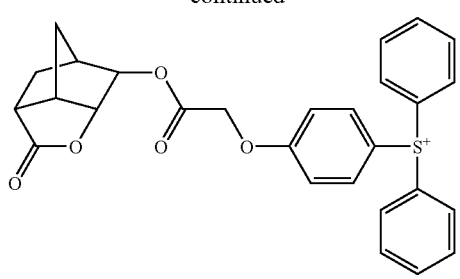
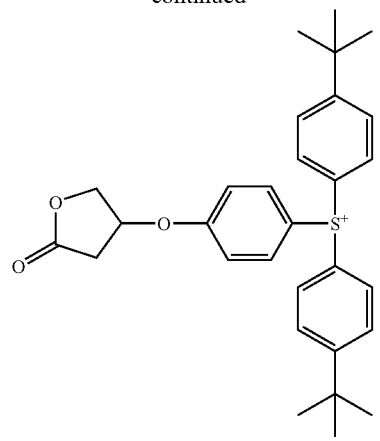
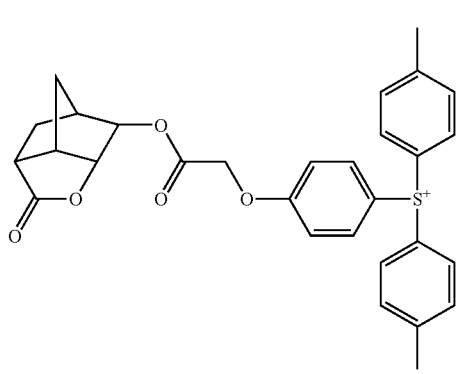
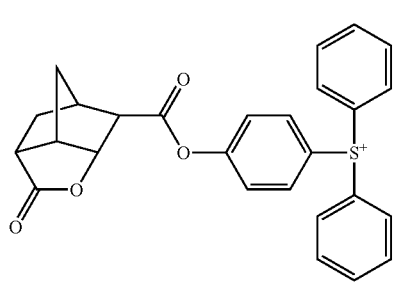
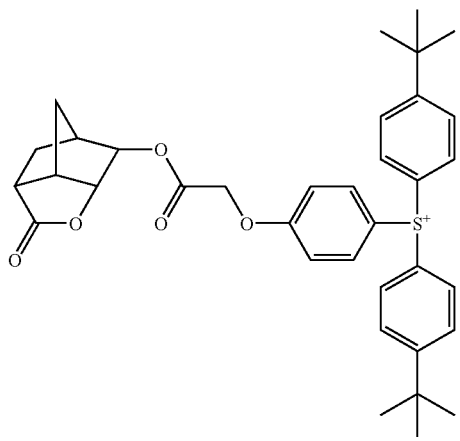
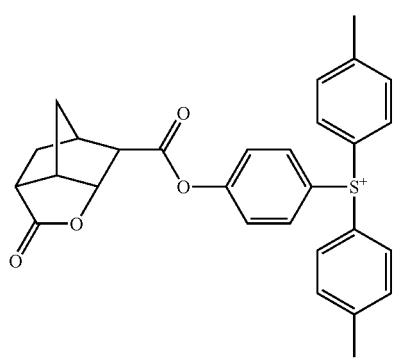
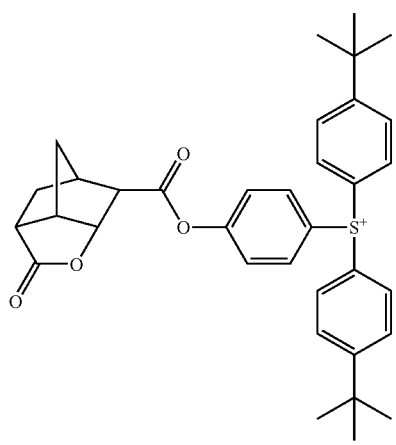
The salt of the present invention consists of any one of the above-mentioned anion part and any one of the above-mentioned cation part and the above-mentioned anion part and the above-mentioned cation part can be arbitrarily combined.
The salts represented by the formulae (I-AA-1') to (I-AA-19') are preferable.

(I-AA-1′)
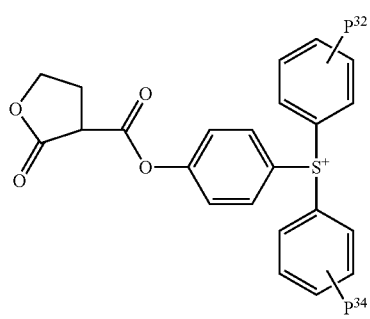
(I-AA-4′)
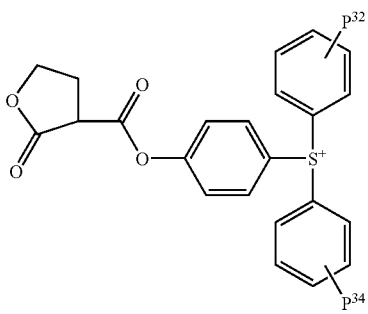
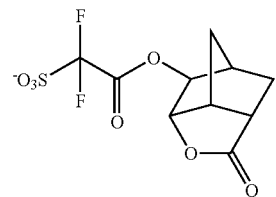
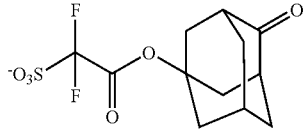
(I-AA-2′)
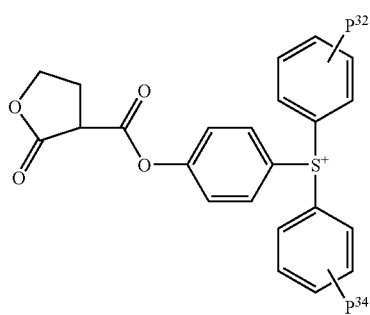
(I-AA-5′)
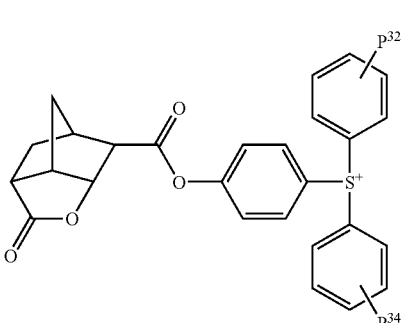
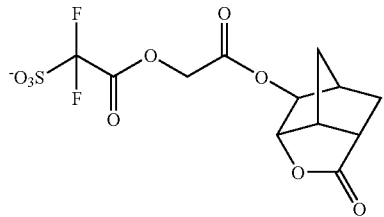
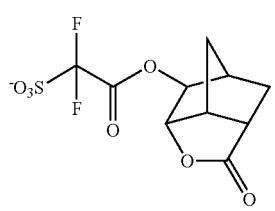
(I-AA-3′)
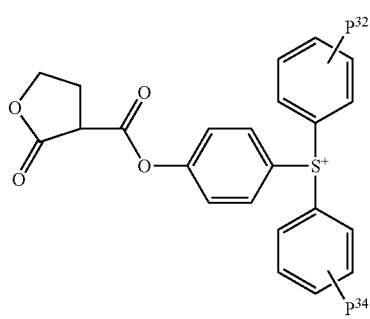
(I-AA-6′)
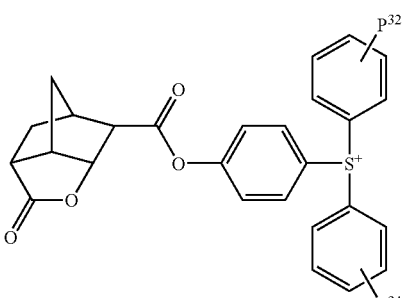
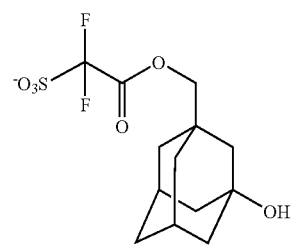
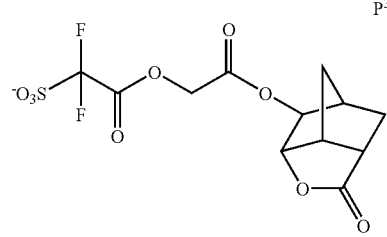

-continued
(I-AA-7')
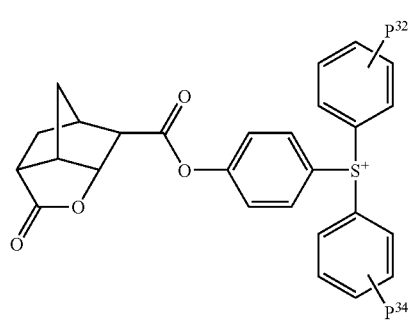
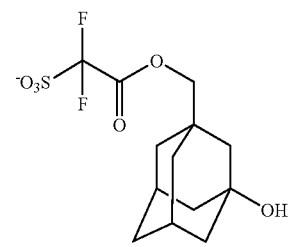
(I-AA-8')
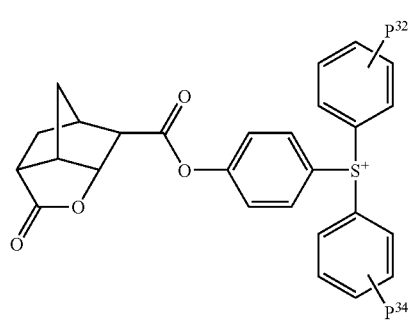
(I-AA-9')
-continued
(I-AA-10')
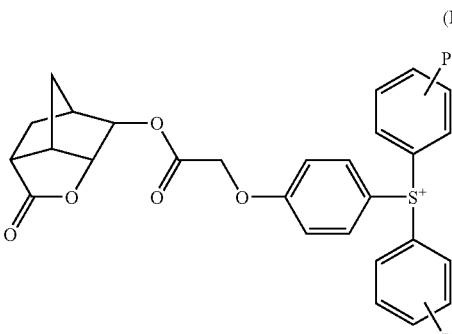
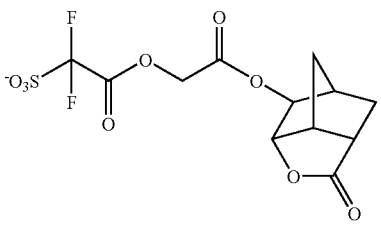
(I-AA-11')
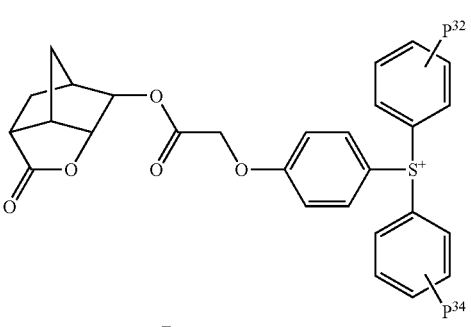
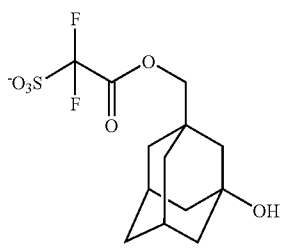
(I-AA-12')
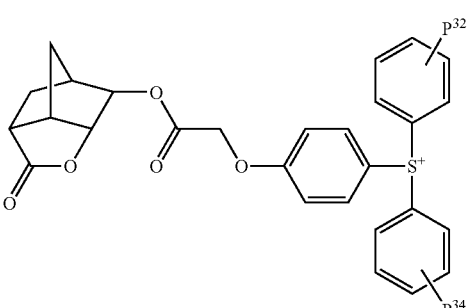
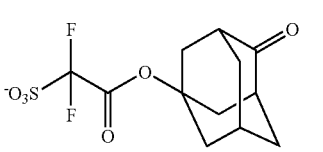

(I-AA-13′)
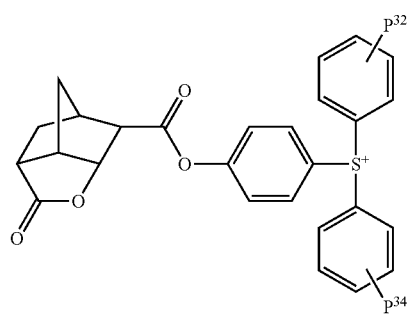
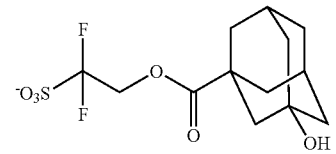
(I-AA-14′)
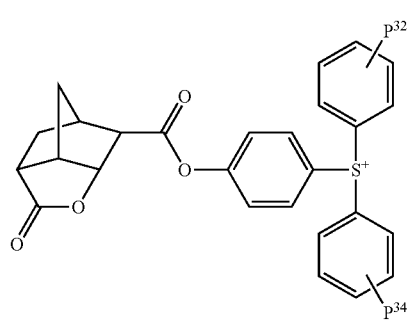
(I-AA-15′)
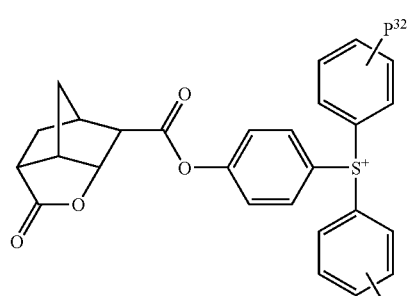
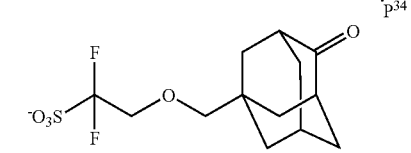
(I-AA-16′)
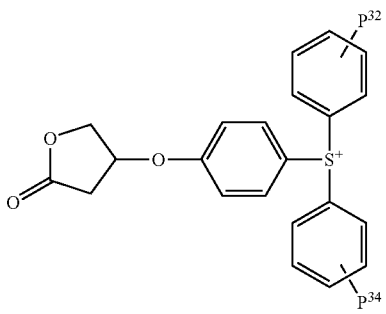
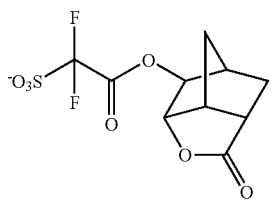
(I-AA-17′)
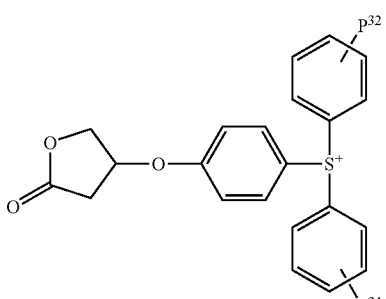
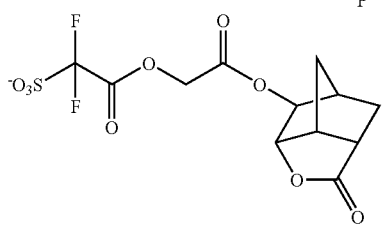
(I-AA-18′)
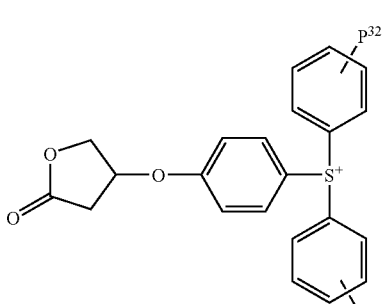
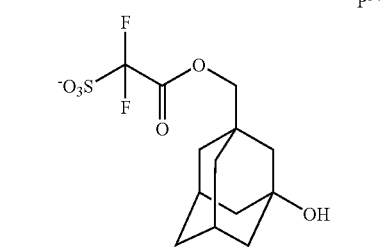

(I-AA-19')
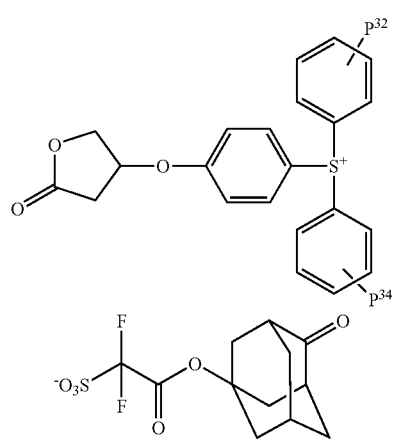
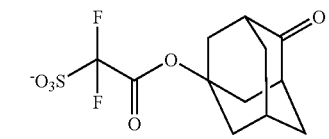
wherein P³² and P³⁴ are the same as defined above.
Preferable examples thereof include the followings.
(I-AA-1)
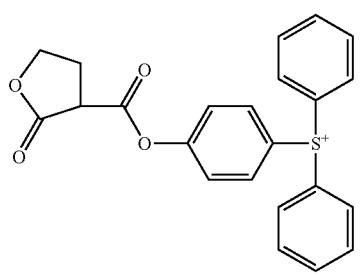
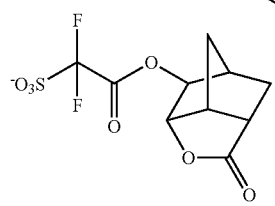
(I-AA-2)
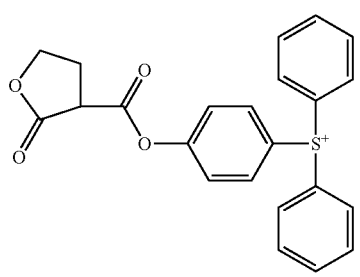
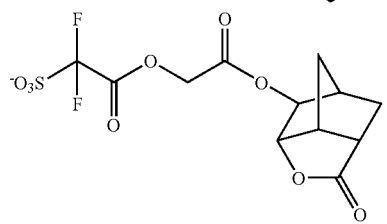
(I-AA-3)
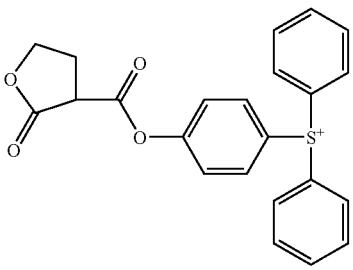
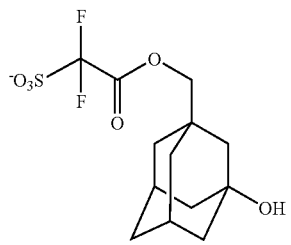
(I-AA-4)
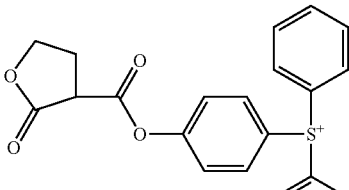
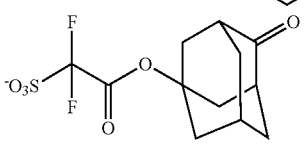
(I-AA-5)
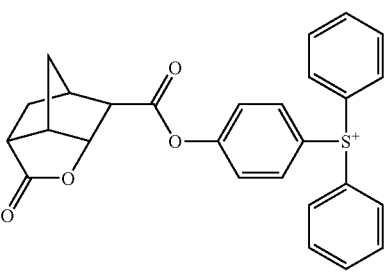
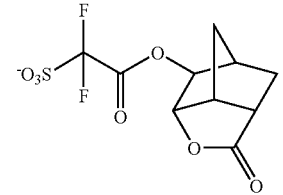

(I-AA-6)
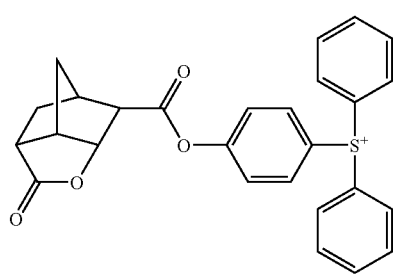
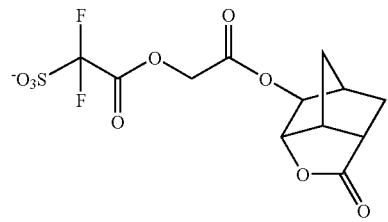
(I-AA-7)
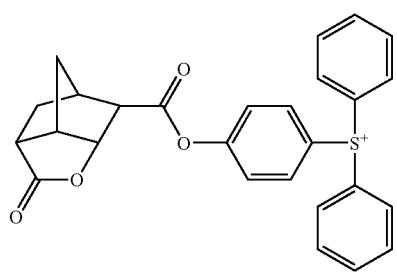
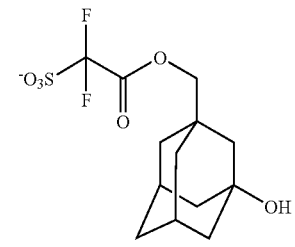
(I-AA-8)
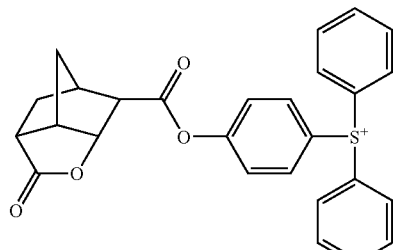
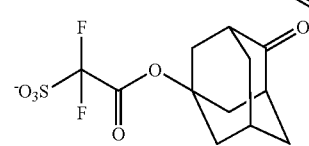
(I-AA-9)
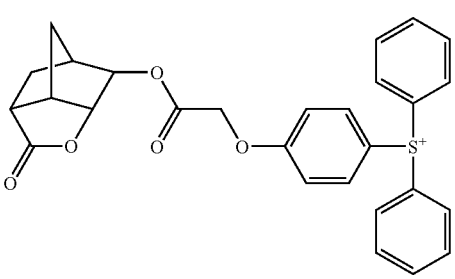
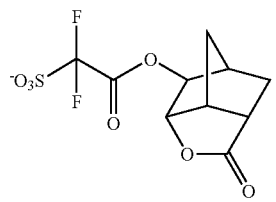
(I-AA-10)
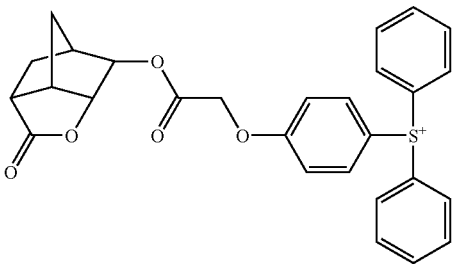
(I-AA-11)
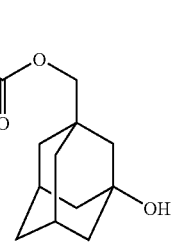

(I-AA-12)
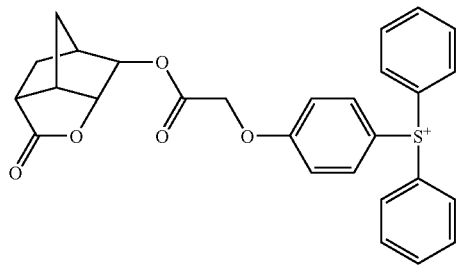
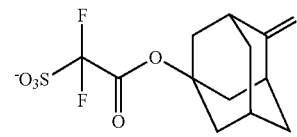
(I-AA-13)
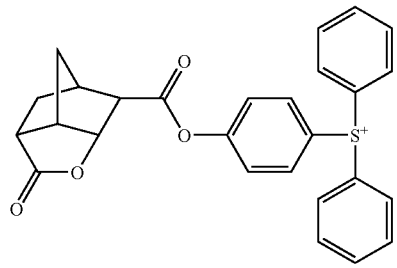
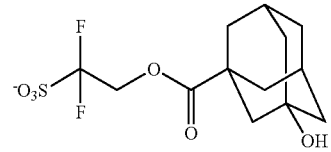
(I-AA-14)
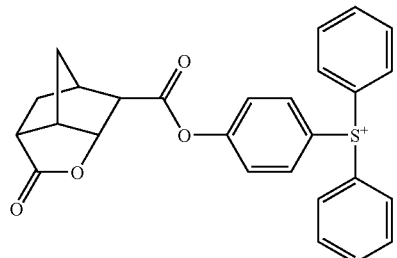
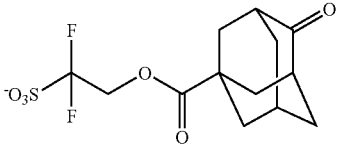
(I-AA-15)
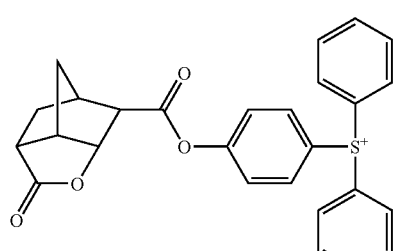
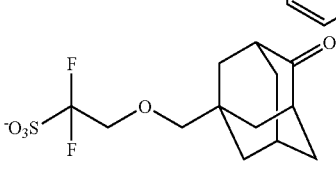
(I-AA-16)
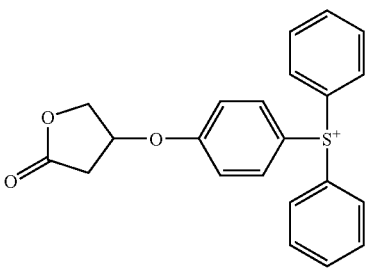
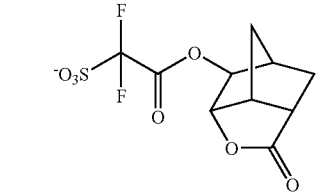
(I-AA-17)
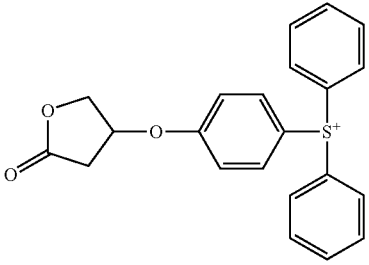
(I-AA-18)
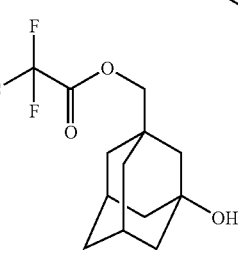

(I-AA-19)

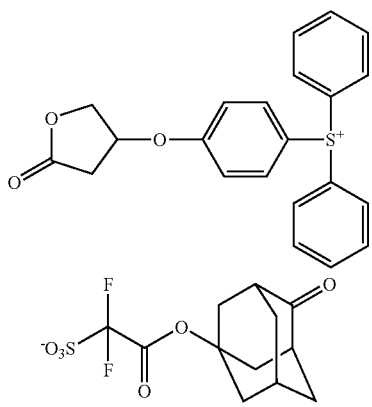

A compound comprising the cation part of the salt of the present invention can be produced according to the known method in the art. For example, a salt represented by the formula (IA) can be produced by reacting a salt represented by the formula (IA-3) with a salt represented by the formula (IA-4) in a solvent such as chloroform.

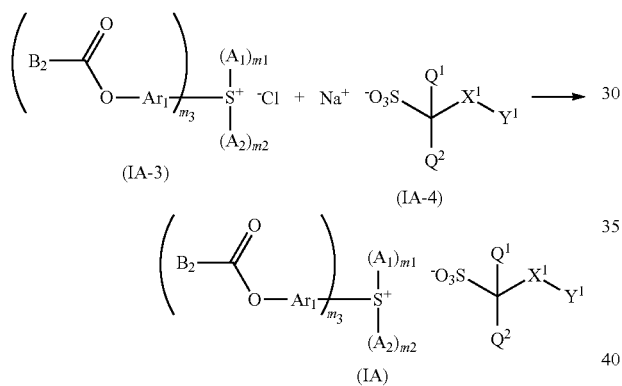

The salt represented by the formula (IA-4) can be produced according to the method described in JP 2008-165216 A.

The salt represented by the formula (IA-3) can be produced by reacting a salt represented by the formula (IA-1) with a compound represented by the formula (IA-2) in the presence of an acid such as sulfuric acid in a solvent such as monochlorobenzene.

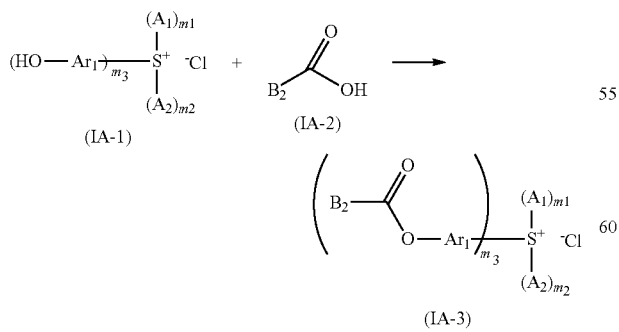

Examples of the salt represented by the formula (IA-1) include 4-hydrorxyphenyldiphenylsulfonium chloride.

Examples of the compound represented by the formula (IA-2) include 5-oxotetrahydrofuran-2-carboxylic acid.

The reaction of the salt represented by the formula (IA-3) with the salt represented by the formula (IA-4) can be conducted, for example, according to the method described in JP 2008-165216 A.

The salt represented by the formula (I-AA) works as an acid generator in a photoresist composition. The acid generator is a substance which is decomposed to generate an acid by applying a radiation such as a light, an electron beam or the like on the substance itself or on a resist composition containing the substance.

The acid generated from the salt of the present invention acts on a resin in a photoresist composition resulting in cleavage of the acid-labile group existing in the resin.

The photoresist composition of the present invention comprises a salt represented by the formula (I-AA) and a resin comprising a structural unit having an acid-labile group and being insoluble or poorly soluble in an aqueous alkali solution but becoming soluble in an aqueous alkali solution by the action of an acid. The photoresist composition can contain one or more acid generators other than the salt represented by the formula (I-AA).

In this specification, "an acid-labile group" means a group capable of being eliminated by the action of an acid.

Examples of the acid-labile group include a group represented by the formula (1a):

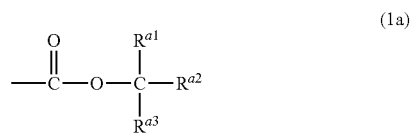

(1a)

wherein $R^{a1}$, $R^{a2}$ and $R^{a1}$ independently each represent a C1-C8 aliphatic hydrocarbon group or a C3-C20 alicyclic hydrocarbon group, or $R^{a1}$ and $R^{a2}$ are bonded each other to form a C3-C20 ring.

Examples of the C1-C8 aliphatic hydrocarbon group include a C1-C8 alkyl group such as a methyl group, an ethyl group, a propyl group, an isopropyl group, a butyl group, a pentyl group, a hexyl group, a heptyl group and an octyl group. The C3-C20 alicyclic hydrocarbon group may be monocyclic or polycyclic, and examples thereof include a monocyclic alicyclic hydrocarbon group such as a C3-C20 cycloalkyl group (e.g. a cyclopentyl group, a cyclohexyl group, a methylcyclohexyl group, a dimethylcyclohexyl group, a cycloheptyl group and a cyclooctyl group) and a polycyclic alicyclic hydrocarbon group such as a decahydronaphthyl group, an adamantyl group, a norbornyl group, a methylnorbornyl group, and the followings:

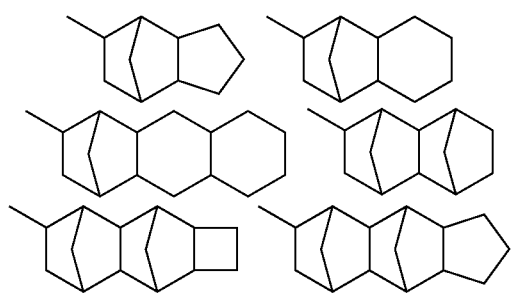

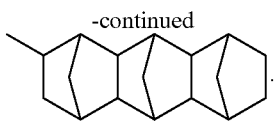

The alicyclic hydrocarbon group preferably has 3 to 16 carbon atoms.

Examples of the ring formed by bonding $R^{a1}$ and $R^{a2}$ each other include the following groups and the ring preferably has 3 to 12 carbon atoms.

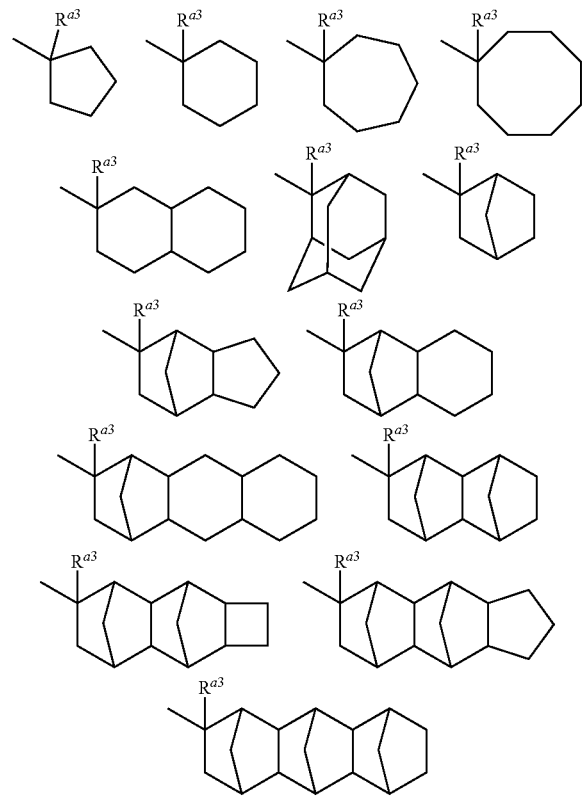

wherein $R^{a3}$ is the same as defined above.

The group represented by the formula (1a) wherein $R^{a1}$, $R^{a2}$ and $R^{a3}$ independently each represent a C1-C8 alkyl group such as a tert-butyl group, the group represented by the formula (1a) wherein $R^{a1}$ and $R^{a2}$ are bonded each other to form an adamantyl ring and $R^{a3}$ is a C1-C8 alkyl group such as a 2-alkyl-2-adamantyl group, and the group represented by the formula (1a) wherein $R^{a1}$ and $R^{a2}$ are C1-C8 alkyl groups and $R^{a3}$ is an adamantyl group such as a 1-(1-adamantyl)-1-alkylalkoxycarbonyl group are preferable.

The structural unit having an acid-labile group is derived from a monomer having an acid-labile group in its side chain and a carbon-carbon double bond, and an acrylate monomer having an acid-labile group in its side chain or a methacrylte monomer having an acid-labile group in its side chain is preferable.

Preferable examples of the monomer include a 2-alkyl-2-adamantyl acrylate, a 2-alkyl-2-adamantyl methacrylate, 1-(1-adamantyl)-1-alkylalkyl acrylate, a 1-(1-adamantyl)-1-alkylalkyl methacrylate, a 2-alkyl-2-adamantyl 5-norbornene-2-carboxylate, a 1-(1-adamantyl)-1-alkylalkyl 5-norbornene-2-carboxylate, a 2-alkyl-2-adamantyl α-chloroacrylate and a 1-(1-adamantyl)-1-alkylalkyl α-chloroacrylate. Particularly when the 2-alkyl-2-adamantyl acrylate or the 2-alkyl-2-adamantyl methacrylate is used as the monomer for the resin component in the photoresist composition, a photoresist composition having excellent resolution tend to be obtained. Typical examples thereof include 2-methyl-2-adamantyl acrylate, 2-methyl-2-adamantyl methacrylate, 2-ethyl-2-adamantyl acrylate, 2-ethyl-2-adamantyl methacrylate, 2-isopropyl-2-adamantyl acrylate, 2-isopropyl-2-adamantyl methacrylate, 2-n-butyl-2-adamantyl acrylate, 2-methyl-2-adamantyl α-chloroacrylate and 2-ethyl-2-adamantyl α-chloroacrylate. When particularly 2-ethyl-2-adamantyl acrylate, 2-ethyl-2-adamantyl methacrylate, 2-isopropyl-2-adamantyl acrylate or 2-isopropyl-2-adamantyl methacrylate is used for the photoresist composition, a photoresist composition having excellent sensitivity and heat resistance tends to be obtained.

The 2-alkyl-2-adamantyl acrylate can be usually produced by reacting a 2-alkyl-2-adamantanol or a metal salt thereof with an acrylic halide, and the 2-alkyl-2-adamantyl methacrylate can be usually produced by reacting a 2-alkyl-2-adamantanol or a metal salt thereof with a methacrylic halide. Two or more kinds of monomers having a group or groups dissociated by the action of the acid may be used together, if necessary.

The content of the structural unit having an acid-labile group in the resin is usually 10 to 80% by mole based on total molar of all the structural units of the resin.

The resin preferably contains one or more structural units having one or more highly polar substituents. Examples of the structural unit having one or more highly polar substituents include a structural unit having a hydrocarbon group having at least one selected from the group consisting of a hydroxyl group, a cyano group, a nitro group and an amino group and a structural unit having a hydrocarbon group having one or more —CO—O—, —CO—, —O—, —SO$_2$— or —S—. A structural unit having a saturated cyclic hydrocarbon group having a cyano group or a hydroxyl group, a structural unit having a saturated cyclic hydrocarbon group in which one or more —CH$_2$— replaced by —O— or —CO—, and a structural unit having a lactone structure in its side chain are preferable, and a structural unit having a bridged hydrocarbon group having one or more hydroxyl groups, and a structural unit having a bridged hydrocarbon group having —CO—O— or —CO— are more preferable. Examples thereof include a structural unit derived from 2-norbornene having one or more hydroxyl groups, a structural unit derived from acrylonitrile or methacrylonitrile, a structural unit derived from hydroxyl-containing adamantyl acrylate or hydroxyl-containing adamantyl methacrylate, a structural unit derived from styrene monomer such as p-hydroxystyrene and m-hydroxystyrene, a structural unit derived from a structural unit derived from 1-adamantyl acrylate or 1-adamantyl methacrylate, and a structural unit derived from acryloyloxy-γ-butyrolactone or methacryloyloxy-γ-butyrolactone having a lactone ring which may have an alkyl group.

Specific examples of the structural unit derived from hydroxyl-containing adamantyl acrylate or hydroxyl-containing adamantyl methacrylate include a structural unit derived from 3-hydroxy-1-adamantyl acrylate; a structural unit derived from 3-hydroxy-1-adamantylmethacrylate; a structural unit derived from 3,5-dihydroxy-1-adamantyl acrylate; and a structural unit derived from 3,5-dihydroxy-1-adamantyl methacrylate.

3-Hydroxy-1-adamantyl acrylate, 3-hydroxy-1-adamantyl methacrylate, 3,5-dihydroxy-1-adamantyl acrylate and 3,5-dihydroxy-1-adamantyl methacrylate can be produced, for example, by reacting corresponding hydroxyadamantane with acrylic acid, methacrylic acid or its acid halide, and they are also commercially available.

When the resin has a structural unit derived from hydroxyl-containing adamantyl acrylate or hydroxyl-containing adamantyl methacrylate, the content thereof is preferably 5 to 50% by mole based on 100% by mole of all the structural units of the resin.

Examples of the structural unit derived from a monomer having a lactone ring which may have an alkyl group include a structural unit derived from acryloyloxy-γ-butyrolactone, a structural unit derived from methacryloyloxy-γ-butyrolactone and structural units represented by the formulae (a) and (b):

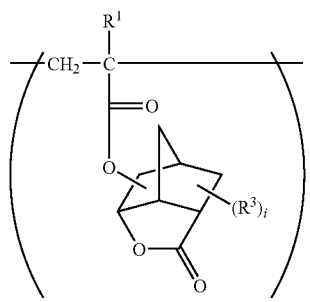

(a)

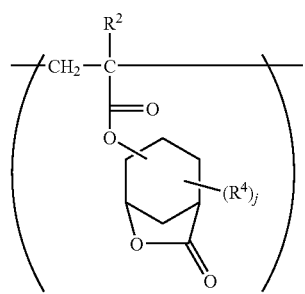

(b)

wherein $R^1$ and $R^2$ independently each represents a hydrogen atom or a methyl group, $R^3$ and $R^4$ are independently in each occurrence a hydrogen atom, a methyl group, a trifluoromethyl group or a halogen atom, and i and j independently each represents an integer of 1 to 3.

Further, the acryloyloxy-γ-butyrolactone and the methacryloyloxy-γ-butyrolactone can be produced by reacting corresponding α- or β-bromo-γ-butyrolactone with acrylic acid or methacrylic acid, or reacting corresponding α- or β-hydroxy-γ-butyrolactone with the acrylic halide or the methacrylic halide.

Examples of the monomers giving structural units represented by the formulae (a) and (b) include an acrylate of alicyclic lactones and a methacrylate of alicyclic lactones having the hydroxyl group described below, and mixtures thereof. These esters can be produced, for example, by reacting the corresponding alicyclic lactone having the hydroxyl group with acrylic acid or methacrylic acid, and the production method thereof is described in, for example, JP 2000-26446 A.

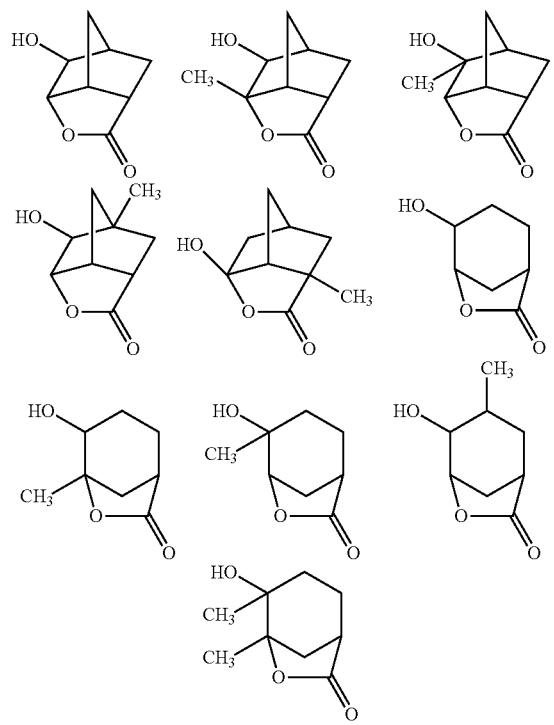

Examples of the acryloyloxy-γ-butyrolactone and the methacryloyloxy-γ-butyrolactone in which lactone ring may be substituted with the alkyl group include α-acryloyloxy-γ-butyrolactone, α-methacryloyloxy-γ-butyrolactone, α-acryloyloxy-β,β-dimethyl-γ-butyrolactone, α-methacryloyloxy-β,β-dimethyl-γ-butyrolactone, α-acryloyloxy-α-methyl-γ-butyrolactone, α-methacryloyloxy-α-methyl-γ-butyrolactone, β-acryloyloxy-γ-butyrolactone, β-methacryloyloxy-γ-butyrolactone and β-methacryloyloxy-α-methyl-γ-butyrolactone.

When the resin has a structural unit derived from a monomer having a lactone ring which may have an alkyl group, the content thereof is preferably 5 to 50% by mole based on 100% by mole of all the structural units of the resin.

Among them, the structural unit derived from 3-hydroxy-1-adamantyl acrylate, the structural unit derived from 3-hydroxy-1-adamantyl methacrylate, the structural unit derived from 3,5-dihydroxy-1-adamantyl acrylate, the structural unit derived from 3,5-dihydroxy-1-adamantyl methacrylate, the structural unit derived from α-acryloyloxy-γ-butyrolactone, the structural unit derived from α-methacryloyloxy-γ-butyrolactone, the structural unit derived from β-acryloyloxy-γ-butyrolactone, the structural unit derived from β-methacryloyloxy-γ-butyrolactone, the structural unit represented by the formula (a) and the structural unit represented by the formula (b) are preferable, because a photoresist composition having good resolution and adhesiveness of photoresist to a substrate tends to be obtained.

When the exposing is conducted using KrF excimer laser, the resin preferably has a structural unit derived from a styrene monomer such as p-hydroxystyrene and m-hydroxystyrene, and the content thereof is preferably 5 to 90% by mole based on 100% by mole of all the structural units of the resin.

The resin can contain the other structural unit or units. Examples thereof include a structural unit derived from acrylic acid or methacrylic acid, a structural unit derived from an alicyclic compound having an olefinic double bond such as a structural unit represented by the formula (c):

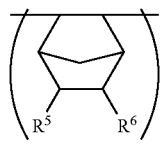

wherein $R^5$ and $R^6$ each independently represents a hydrogen atom, a C1-C3 alkyl group, a carboxyl group, a cyano group or a —COOU group in which U represents an alcohol residue, or $R^5$ and $R^6$ can be bonded together to form a carboxylic anhydride residue represented by —C(=O)OC(=O)
a structural unit derived from an aliphatic unsaturated dicarboxylic anhydride such as a structural unit represented by the formula (d):

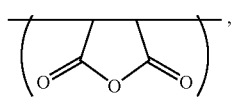

or
a structural unit represented by the formula (e):

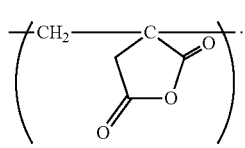

In $R^5$ and $R^6$, examples of the C1-C3 alkyl group include a methyl group, an ethyl group, a propyl group and an isopropyl group. The —COOU group is an ester formed from the carboxyl group, and examples of the alcohol residue corresponding to U include an optionally substituted C1-C8 alkyl group, 2-oxooxolan-3-yl group and 2-oxooxolan-4-yl group, and examples of the substituent on the C1-C8 alkyl group include a hydroxyl group and an alicyclic hydrocarbon group.

Specific examples of the monomer giving the structural unit represented by the above-mentioned formula (c) may include 2-norbornene, 2-hydroxy-5-norbornene, 5-norbornene-2-carboxylic acid, methyl 5-norbornene-2-carboxylate, 2-hydroxyethyl 5-norbornene-2-carboxylate, 5-norbornene-2-methanol and 5-norbornene-2,3-dicarboxylic anhydride.

When U in the —COOU group is the acid-labile group, the structural unit represented by the formula (c) is a structural unit having the acid-labile group even if it has the norbornane structure. Examples of monomers giving a structural unit having the acid-labile group include tert-butyl 5-norbornene-2-carboxylate, 1-cyclohexyl-1-methylethyl 5-norbornene-2-carboxylate, 1-methylcyclohexyl 5-norbornene-2-carboxylate, 2-methyl-2-adamantyl 5-norbornene-2-carboxylate, 2-ethyl-2-adamantyl 5-norbornene-2-carboxylate, 1-(4-methylcyclohexyl)-1-methylethyl 5-norbornene-2-carboxylate, 1-(4-hydroxylcyclohexyl)-1-methylethyl 5-norbornene-2-carboxylate, 1-methyl-1-(4-oxocyclohexyl)ethyl 5-norbornene-2-carboxylate and 1-(1-adamantyl)-1-methylethyl 5-norbornene-2-carboxylate.

The resin can be obtained by conducting polymerization reaction of a monomer or monomers having the acid-labile group and an olefinic double bond. The polymerization reaction is usually carried out in the presence of a radical initiator. This polymerization reaction can be conducted according to known methods.

The resin usually has 10,000 or more of the weight-average molecular weight, preferably 10,500 or more of the weight-average molecular weight, more preferably 11,000 or more of the weight-average molecular weight, much more preferably 11,500 or more of the weight-average molecular weight, and especially preferably 12,000 or more of the weight-average molecular weight. When the weight-average molecular weight of the resin is too large, defect of the photoresist film tends to generate, and therefore, the resin preferably has 40,000 or less of the weight-average molecular weight, more preferably 39,000 or less of the weight-average molecular weight, much more preferably 38,000 or less of the weight-average molecular weight, and especially preferably 37,000 or less of the weight-average molecular weight. The weight-average molecular weight can be measured with gel permeation chromatography.

The present resist composition preferably includes 80 to 99.9% by weight of the resin component and 0.1 to 20% by weight of the acid generator component based on sum of the resin component and the acid generator component. Herein, "acid generator component" means the salt represented by the formula (I-AA) and the other acid generator(s) contained in the photoresist composition.

In the present resist composition, performance deterioration caused by inactivation of acid which occurs due to post exposure delay can be diminished by adding an organic base compound, particularly a nitrogen-containing organic base compound as a quencher.

Specific examples of the nitrogen-containing organic base compound include an amine compound represented by the following formulae:

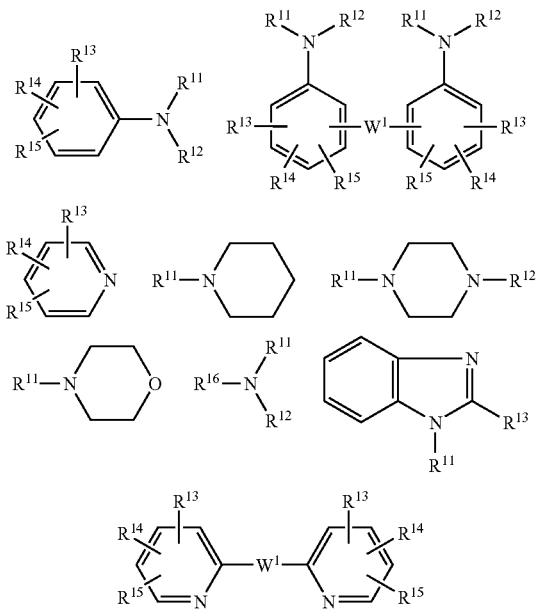

-continued

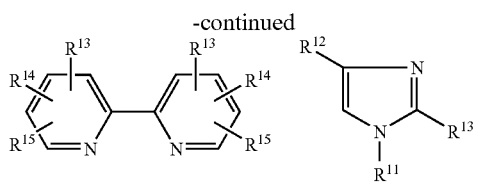

wherein $R^{11}$ and $R^{12}$ independently represent a hydrogen atom, a C1-C6 alkyl group, a C5-C10 cycloalkyl group or a C6-C10 aryl group, and the alkyl, cycloalkyl and aryl groups may be substituted with at least one group selected from the group consisting of a hydroxyl group, an amino group which may be substituted with a C1-C4 alkyl group and a C1-C6 alkoxy group which may be substituted with a C1-C6 alkoxy group, $R^{13}$ and $R^{14}$ independently represent a hydrogen atom, a C1-C6 alkyl group, a C5-C10 cycloalkyl group, a C6-C10 aryl group or a C1-C6 alkoxy group, and the alkyl, cycloalkyl, aryl and alkoxy groups may be substituted with at least one group selected from the group consisting of a hydroxyl group, an amino group which may be substituted with a C1-C4 alkyl group and a C1-C6 alkoxy group, or $R^{13}$ and $R^{14}$ bond together with the carbon atoms to which they bond to form an aromatic ring, $R^{15}$ represent a hydrogen atom, a C1-C6 alkyl group, a C5-C10 cycloalkyl group, a C6-C10 aryl group, a C1-C6 alkoxy group or a nitro group, and the alkyl, cycloalkyl, aryl and alkoxy groups may be substituted with at least one group selected from the group consisting of a hydroxyl group, an amino group which may be substituted with a C1-C4 alkyl group and a C1-C6 alkoxy group, $R^{16}$ represents a C1-C6 alkyl group or a C5-C10 cycloalkyl group, and the alkyl and cycloalkyl groups may be substituted with at least one group selected from the group consisting of a hydroxyl group, an amino group which may be substituted with a C1-C4 alkyl group and a C1-C6 alkoxy group, and $W^1$ represents —CO—, —NH—, —S—, —S—S—, an C2-C6 alkylene group, and a quaternary ammonium hydroxide represented by the following formula:

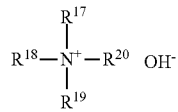

wherein $R^{17}$, $R^{18}$, $R^{19}$ and $R^{20}$ independently represent a C1-C6 alkyl group, a C5-C10 cycloalkyl group or a C6-C10 aryl group, and the alkyl, cycloalkyl and aryl groups may be substituted with at least one group selected from the group consisting of a hydroxyl group, an amino group which may be substituted with a C1-C4 alkyl group and a C1-C6 alkoxy group.

Examples of the amino group which may be substituted with the C1-C4 alkyl group include an amino group, a methylamino group, an ethylamino group, a butylamino group, a dimethylamino group and a diethylamino group. Examples of the C1-C6 alkoxy group which may be substituted with the C1-C6 alkoxy group include a methoxy group, an ethoxy group, a propoxy group, an isopropoxy group, a butoxy group, a tert-butoxy group, a pentyloxy group, a hexyloxy group and a 2-methoxyethoxy group.

Specific examples of the C1-C6 alkyl group which may be substituted with at least one group selected from the group consisting of a hydroxyl group, an amino group which may be substituted with a C1-C4 alkyl group, and a C1-C6 alkoxy group which may be substituted with a C1-C6 alkoxy group include a methyl group, an ethyl group, a propyl group, an isopropyl group, a butyl group, a tert-butyl group, a pentyl group, a hexyl group, a 2-(2-methoxyethoxy)ethyl group, a 2-hydroxyethyl group, a 2-hydroxypropyl group, a 2-aminoethyl group, a 4-aminobutyl group and a 6-aminohexyl group.

Specific examples of the C5-C10 cycloalkyl group which may be substituted with at least one group selected from the group consisting of a hydroxyl group, an amino group which may be substituted with a C1-C4 alkyl group and a C1-C6 alkoxy group include a cyclopentyl group, a cyclohexyl group, a cycloheptyl group and a cyclooctyl group.

Specific examples of the C6-C10 aryl group which may be substituted with at least one group selected from the group consisting of a hydroxyl group, an amino group which may be substituted with a C1-C4 alkyl group or a C1-C6 alkoxy group include a phenyl group and a naphthyl group.

Specific examples of the C1-C6 alkoxy group include a methoxy group, an ethoxy group, a propoxy group, an isopropoxy group, a butoxy group, a tert-butoxy group, a pentyloxy group and a hexyloxy group.

Specific examples of the C2-C6 alkylene group include an ethylene group, a trimethylene group and a tetramethylene group.

Specific examples of the amine compound include hexylamine, heptylamine, octylamine, nonylamine, decylamine, aniline, 2-methylaniline, 3-methylaniline, 4-methylaniline, 4-nitroaniline, 1-naphthylamine, 2-naphthylamine, ethylenediamine, tetramethylenediamine, hexamethylenediamine, 4,4'-diamino-1,2-diphenylethane, 4,4'-diamino-3,3'-dimethyldiphenylmethane, 4,4'-diamino-3,3'-diethyldiphenylmethane, dibutylamine, dipentylamine, dihexylamine, diheptylamine, dioctylamine, dinonylamine, didecylamine, N-methylaniline, piperidine, diphenylamine, triethylamine, trimethylamine, tripropylamine, tributylamine, tripentylamine, trihexylamine, triheptylamine, trioctylamine, trinonylamine, tridecylamine, methyldibutylamine, methyldipentylamine, methyldihexylamine, methyldicyclohexylamine, methyldiheptylamine, methyldioctylamine, methyldinonylamine, methyldidecylamine, ethyldibutylamine, ethyldipentylamine, ethyldihexylamine, ethyldiheptylamine, ethyldioctylamine, ethyldinonylamine, ethyldidecylamine, dicyclohexylmethylamine, tris[2-(2-methoxyethoxy)ethyl] amine, triisopropanolamine, N,N-dimethylaniline, 2,6-diisopropylaniline, imidazole, benzimidazole, pyridine, 4-methylpyridine, 4-methylimidazole, bipyridine, 2,2'-dipyridylamine, di-2-pyridyl ketone, 1,2-di(2-pyridyl) ethane, 1,2-di(4-pyridyl)ethane, 1,3-di(4-pyridyl)propane, 1,2-bis(2-pyridyl)ethylene, 1,2-bis(4-pyridyl)ethylene, 1,2-bis(4-pyridyloxy)ethane, 4,4'-dipyridyl sulfide, 4,4'-dipyridyl disulfide, 1,2-bis(4-pyridyl)ethylene, 2,2'-dipicolylamine and 3,3'-dipicolylamine.

Examples of the quaternary ammonium hydroxide include tetramethylammonium hydroxide, tetrabutylammonium hydroxide, tetrahexylammonium hydroxide, tetraoctylammonium hydroxide, phenyltrimethylammonium hydroxide, (3-trifluoromethylphenyl)trimethylammonium hydroxide and (2-hydroxyethyl)trimethylammonium hydroxide (so-called "choline").

A hindered amine compound having a piperidine skeleton as disclosed in JP 11-52575 A1 can be also used as the quencher.

In the point of forming patterns having higher resolution, the quaternary ammonium hydroxide is preferably used as the quencher.

When the basic compound is used as the quencher, the present resist composition preferably includes 0.01 to 1% by weight of the basic compound based on the total amount of the resin component and the acid generator component.

The present resist composition can contain, if necessary, a small amount of various additives such as a sensitizer, a dissolution inhibitor, other polymers, a surfactant, a stabilizer and a dye as long as the effect of the present invention is not prevented.

The present resist composition is usually in the form of a resist liquid composition in which the above-mentioned ingredients are dissolved in a solvent and the resist liquid composition is applied onto a substrate such as a silicon wafer by a conventional process such as spin coating. The solvent used is sufficient to dissolve the above-mentioned ingredients, have an adequate drying rate, and give a uniform and smooth coat after evaporation of the solvent. Solvents generally used in the art can be used.

Examples of the solvent include a glycol ether ester such as ethyl cellosolve acetate, methyl cellosolve acetate and propylene glycol monomethyl ether acetate; an acyclic ester such as ethyl lactate, butyl acetate, amyl acetate and ethyl pyruvate; a ketone such as acetone, methyl isobutyl ketone, 2-heptanone and cyclohexanone; and a cyclic ester such as γ-butyrolactone. These solvents may be used alone and two or more thereof may be mixed to use.

A photoresist pattern can be produced by the following steps (1) to (5):

(1) a step of applying the photoresist composition according to claim 8 or 9 on a substrate, (2) a step of forming a photoresist film by conducting drying, (3) a step of exposing the photoresist film to radiation, (4) a step of baking the exposed photoresist film, and (5) a step of developing the baked photoresist film with an alkaline developer, thereby forming a photoresist pattern. The alkaline developer used may be any one of various alkaline aqueous solution used in the art. Generally, an aqueous solution of tetramethylammonium hydroxide or (2-hydroxyethyl) trimethylammonium hydroxide (commonly known as "choline") is often used.

EXAMPLES

The present invention will be described more specifically by Examples, which are not construed to limit the scope of the present invention.

The "%" and "part(s)" used to represent the content of any component and the amount of any material used in the following examples and comparative examples are on a weight basis unless otherwise specifically noted. The weight-average molecular weight of any material used in the following examples is a value found by gel permeation chromatography [HLC-8120GPC Type, Column (Three Columns with guard column): TSKgel Multipore HXL-M, manufactured by TOSOH CORPORATION, Solvent: Tetrahydrofuran, Flow rate: 1.0 mL/min., Detector: RI detector, Column temperature: 40° C., Injection volume: 100 μL] using polystyrene as a standard reference material. Structures of compounds were determined by NMR (EX-270 Type, manufactured by JEOL LTD.) and mass spectrometry (Liquid Chromatography: 1100 Type, manufactured by AGILENT TECHNOLOGIES LTD., Mass Spectrometry: LC/MSD Type or LC/MSD TOF Type, manufactured by AGILENT TECHNOLOGIES LTD.).

Example 1

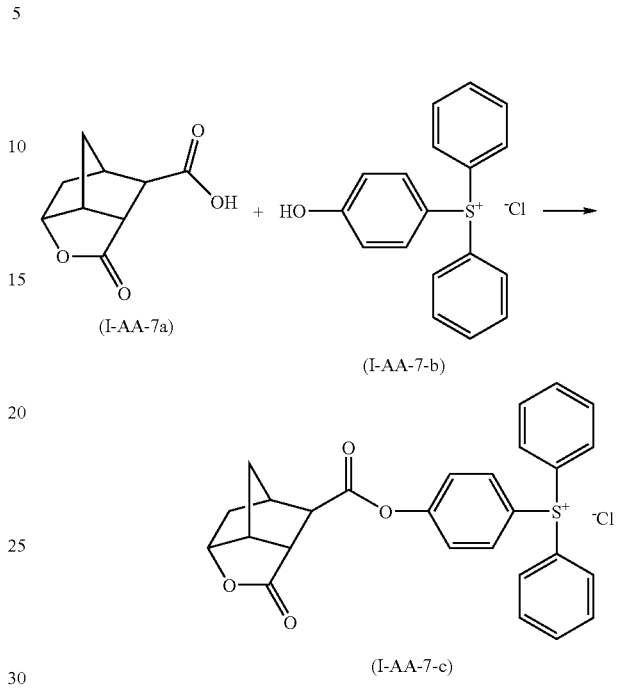

Twenty five parts of monochlorobenzene, 1.82 parts of a compound represented by the formula (I-AA-7a) and 3.15 parts of a compound represented by the formula (I-AA-7-b) were mixed and the resultant mixture was stirred at 23° C. for 30 minutes. To the mixture, 0.98 part of sulfuric acid and 14 parts of molecular sieves 3A available from Wako Pure Chemical Industries, Ltd. were added, and the resultant mixture was stirred at 125° C. for 8 hours. The obtained mixture was cooled and then, concentrated. The obtained residue was mixed with 38.85 parts of chloroform and the resultant mixture was stirred at 23° C. for 30 minutes. The mixture was washed three times with 13.60 parts of ion-exchanged water and the obtained organic layer was concentrated to obtain a compound represented by the formula (I-AA-7-c) in the form of a pale yellow oil.

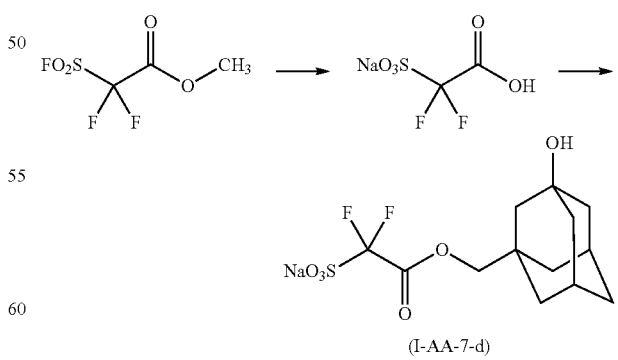

Into a mixture of 100 parts of methyl difluoro(fluorosulfonyl)acetate and 150 parts of ion-exchanged water, 230 parts of 30% aqueous sodium hydroxide solution was added dropwise in an ice bath. The resultant mixture was heated and refluxed at 100° C. for 3 hours. After cooling down to 23° C., the mixture was neutralized with 88 parts of concentrated hydrochloric acid and the solution obtained was concentrated to obtain 164.4 parts of sodium salt of difluorosulfoacetic acid (containing inorganic salt, purity: 62.7%).

To a mixture of 1.9 parts of sodium salt of difluorosulfoacetic acid (purity: 62.7%) and 9.5 parts of N,N-dimethylformamide, 1.0 part of 1,1'-carbonyldiimidazole was added and the resultant solution was stirred for 2 hours. The solution was added to the solution prepared by mixing 1.1 parts of 3-hydroxyadamantanemethanol, 5.5 parts of N,N-dimethylformamide and 0.2 part of sodium hydride and stirring for 2 hours. The resultant solution was stirred for 15 hours to obtain the solution containing the salt represented by the above-mentioned formula (I-AA-7-d).

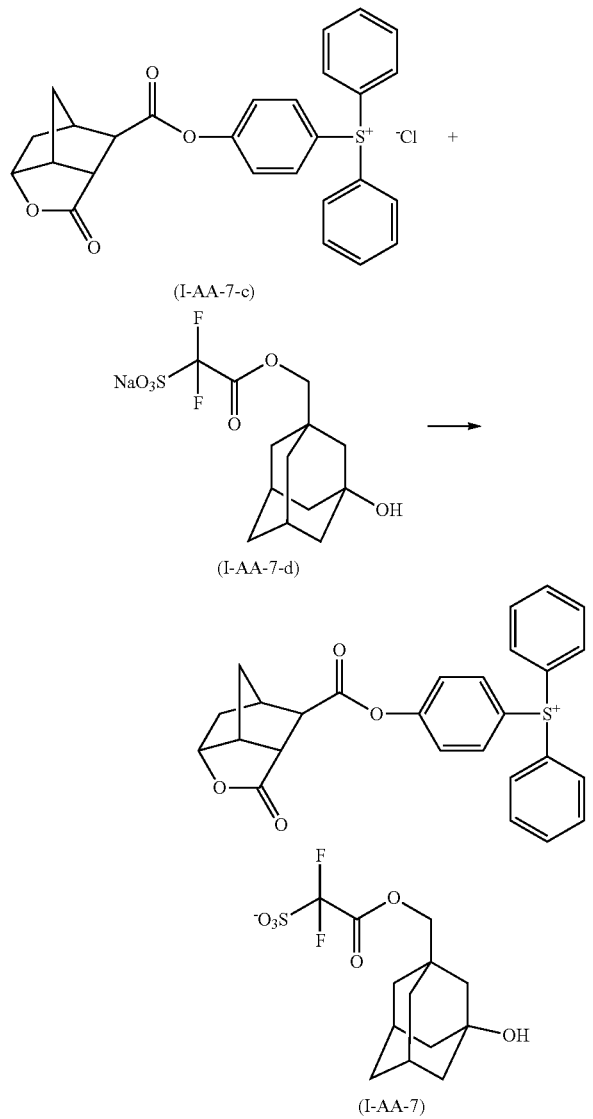

To a solution containing 1.81 parts of the salt represented by the above-mentioned formula (I-AA-7-d), 3.2 parts of chloroform and 2.39 parts of the compound represented by the formula (I-AA-7-c) were added. The resultant mixture was stirred for 15 hours, and then washed with ion-exchanged water. To the obtained organic layer, 1.2 parts of active carbon was added to stir. The resultant mixture was filtrated and the obtained filtrate was concentrated. The obtained residue was mixed with 10 parts of ethyl acetate and the supernatant solution was removed. The obtained residue was mixed with 10 parts of tert-butyl methyl ether and the supernatant solution was removed. The obtained residue was dissolved in chloroform, and the obtained solution was concentrated to obtain 0.98 part of the salt represented by the above-mentioned formula (I-AA-7) in the form of an orange-colored oil, which is called as Salt A1.

Purity: 100%, Yield: 25%.
MS (ESI(+) Spectrum): M$^+$ 443.1
MS (ESI(−) Spectrum): M$^−$ 339.1
$^1$H-NMR (dimethylsulfoxide-d$_6$, Internal Standard: tetramethylsilane): δ (ppm) 1.30-2.08 (m, 17H), 2.10 (m, 2H), 2.63 (m, 1H), 2.87-2.94 (m, 2H), 3.85 (s, 2H), 3.90 (m, 1H), 4.42 (brs, 1H), 7.32-7.38 (m, 2H), 7.70-7.90 (m, 12H)

Example 2

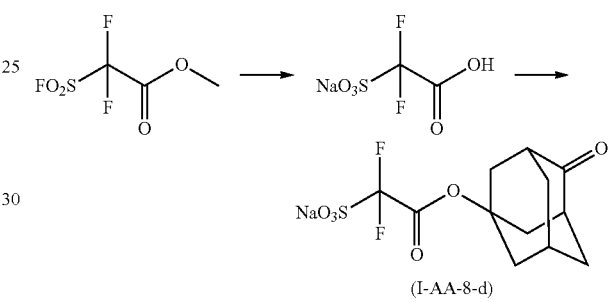

Into a mixture of 100 parts of methyl difluoro (fluorosulfonyl)acetate and 250 parts of ion-exchanged water, 230 parts of 30% aqueous sodium hydroxide solution was added dropwise in an ice bath. The resultant mixture was heated and refluxed at 100° C. for 3 hours. After cooling down to 23° C., the mixture was neutralized with 88 parts of concentrated hydrochloric acid and the solution obtained was concentrated to obtain 164.8 parts of sodium salt of difluorosulfoacetic acid (containing inorganic salt, purity: 62.6%).

To a mixture of 5.0 parts of sodium salt of difluorosulfoacetic acid (purity: 62.6%), 2.6 parts of 4-oxo-1-1adamantanol and 100 parts of ethylbenzene, 0.8 part of concentrated sulfuric acid was added and the resultant mixture was refluxed for 30 hours. The mixture was cooled and filtrated. The obtained solid was washed with methyl tert-butyl ether to obtain 5.5 parts of the salt represented by the above-mentioned formula (I-AA-8-d). The purity thereof was 35.6% according to $^1$H-NMR analysis.

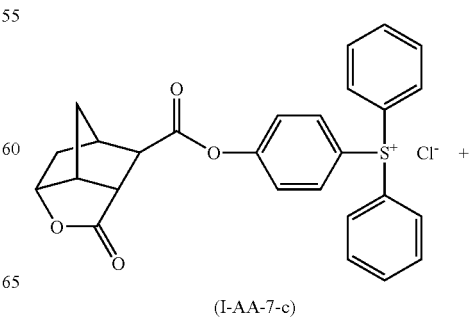

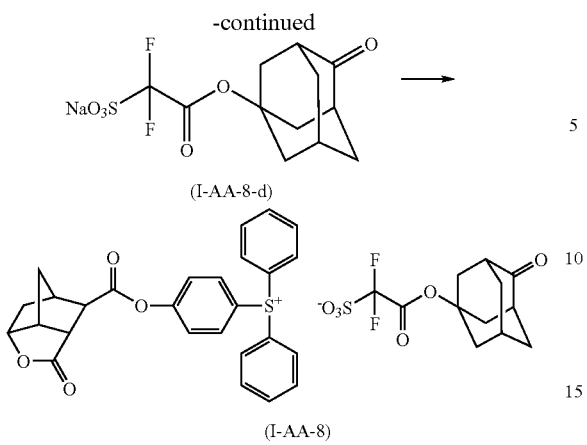

To 4.86 parts of the salt represented by the above-mentioned formula (I-AA-8-d), 15 parts of acetonitrile and 15 parts of ion-exchanged water were added, and 2.39 parts of the compound represented by the formula (I-AA-7-c), 5 parts of acetonitrile and 5 parts of ion-exchanged water were added thereto. The resultant mixture was stirred for 15 hours, and then concentrated. The obtained residue was extracted with 50 parts of chloroform, and the obtained organic layer was washed with ion-exchanged water. To the obtained organic layer, 1.2 parts of active carbon was added to stir. The resultant mixture was filtrated and the obtained filtrate was concentrated. The obtained residue was mixed with 10 parts of ethyl acetate and the supernatant solution was removed. The obtained residue was mixed with 10 parts of tert-butyl methyl ether and the supernatant solution was removed. The obtained residue was dissolved in chloroform, and the obtained solution was concentrated to obtain 1.24 parts of the salt represented by the above-mentioned formula (I-AA-8) in the form of an orange-colored oil, which is called as Salt A2. Purity: 100%, Yield: 32%.

MS (ESI(+) Spectrum): M$^+$ 443.1
MS (ESI(−) Spectrum): M$^-$ 323.0
$^1$H-NMR (dimethylsulfoxide-d$_6$, Internal Standard: tetramethylsilane): δ (ppm) 1.28-2.32 (m, 16H), 2.53 (s, 2H), 2.63 (m, 1H), 2.87-2.94 (m, 2H), 3.90 (m, 1H), 7.32-7.38 (m, 2H), 7.70-7.90 (m, 12H)

Example 3

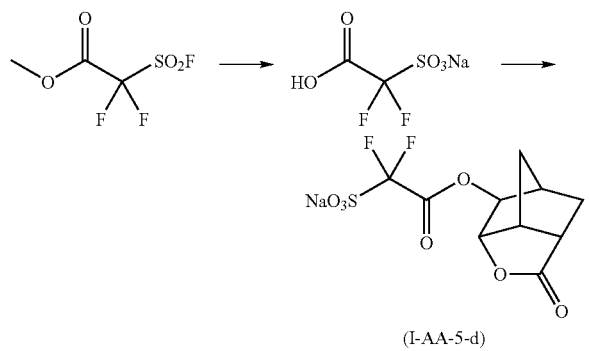

Into a mixture of 100 parts of methyl difluoro (fluorosulfonyl)acetate and 150 parts of ion-exchanged water, 230 parts of 30% aqueous sodium hydroxide solution was added dropwise in an ice bath. The resultant mixture was heated and refluxed at 100° C. for 3 hours. After cooling down to 23° C., the mixture was neutralized with 88 parts of concentrated hydrochloric acid and the solution obtained was concentrated to obtain 164.4 parts of sodium salt of difluorosulfoacetic acid (containing inorganic salt, purity: 62.70).

To a mixture of 30.0 parts of sodium salt of difluorosulfoacetic acid (purity: 62.7%), 14.7 parts of hexahydro-6-hydroxy-3,5-methano-2H-cyclopenta[b]furan-2-one and 300 parts of toluene, 18.1 parts of p-toluenesulfonic acid was added and the resultant mixture was refluxed for 12 hours. The mixture was cooled and filtrated. The obtained solid was dissolved in 100 parts of acetonitrile and the obtained mixture was filtrated. The obtained filtrate was concentrated to obtain 26.7 parts of the salt represented by the above-mentioned formula (I-AA-5-d). The purity thereof was 28.6% according to $^1$H-NMR analysis.

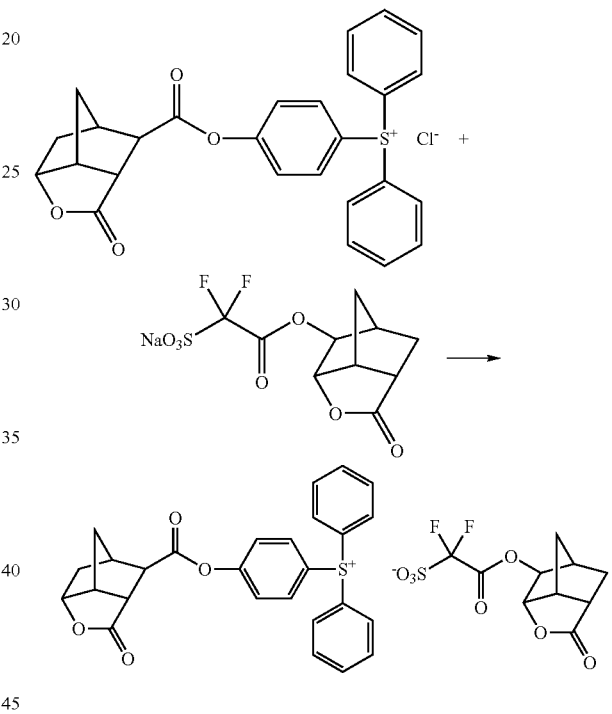

To 5.84 parts of the salt represented by the above-mentioned formula (I-AA-5-d), 20 parts of acetonitrile and 20 parts of ion-exchanged water were added, and 2.39 parts of the compound represented by the formula (I-AA-7-c), 5 parts of acetonitrile and 5 parts of ion-exchanged water were added thereto. The resultant mixture was stirred for 15 hours, and then concentrated. The obtained residue was extracted with 50 parts of chloroform, and the obtained organic layer was washed with ion-exchanged water. To the obtained organic layer, 1.2 parts of active carbon was added to stir. The resultant mixture was filtrated and the obtained filtrate was concentrated. The obtained residue was mixed with 10 parts of ethyl acetate and the supernatant solution was removed. The obtained residue was mixed with 10 parts of tert-butyl methyl ether and the supernatant solution was removed. The obtained residue was dissolved in chloroform, and the obtained solution was concentrated to obtain 0.73 parts of the salt represented by the above-mentioned formula (I-AA-5) in the form of an orange-colored oil, which is called as Salt A3. Purity: 100%, Yield: 190.

MS (ESI(+) Spectrum): M$^+$ 443.1
MS (ESI(−) Spectrum): M$^-$ 311.0

$^1$H-NMR (dimethylsulfoxide-$d_6$, Internal Standard: tetramethylsilane): δ (ppm) 1.28-2.32 (m, 10H), 2.53 (m, 1H), 2.63 (m, 1H), 2.87-2.94 (m, 2H), 3.21 (m 1H), 3.90 (m, 1H), 4.53-4.56 (m, 2H), 7.32-7.38 (m, 2H), 7.70-7.90 (m, 12H)

Example 4

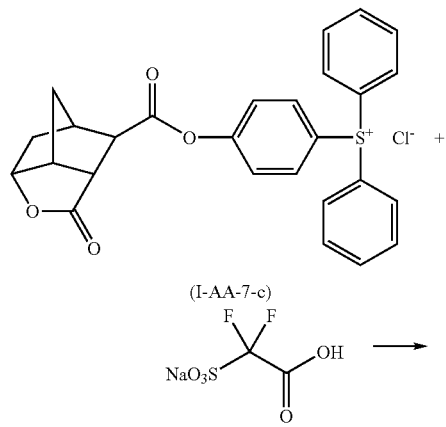

(I-AA-7-c)

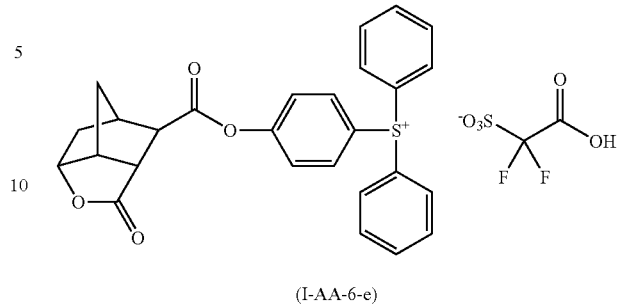

(I-AA-6-e)

To 4.78 parts of the compound represented by the above-mentioned formula (I-AA-7-c), 11.00 parts of 18.0% aqueous sodium salt of difluorosulfoacetic acid solution was added. The resultant mixture was stirred at 25° C. for about 20 hours. The precipitated white solid was collected by filtration and washed with 20 parts of ion-exchanged water and then dried to obtain 4.82 parts of a salt represented by the above-mentioned formula (I-AA-6-e).

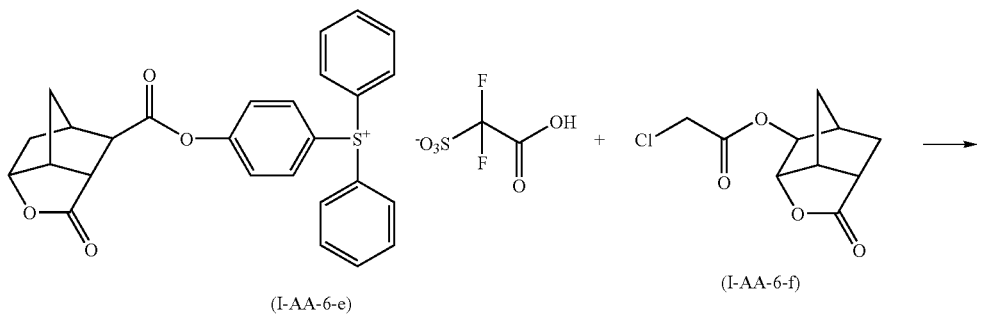

(I-AA-6-e)  (I-AA-6-f)

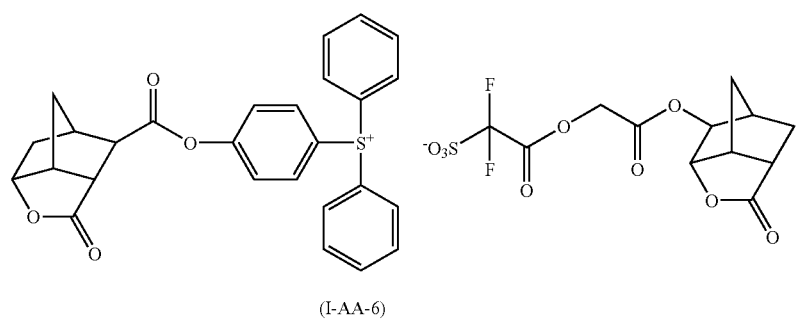

(I-AA-6)

A mixture of 3.09 parts of the salt represented by the above-mentioned formula (I-AA-6-e) and 15.45 parts of N,N-dimethylformamide was stirred at 23° C. for 30 minutes. To the mixture, 0.69 part of potassium carbonate and 0.21 part of potassium iodide were added and the resultant mixture was stirred at 50° C. for 1 hour. The obtained mixture was cooled down to 40° C., and a solution prepared by dissolving 1.15 parts of the compound represented by the formula (I-AA-6-f) in 9.2 parts of N,N-dimethylformamide was added dropwise thereto, and the resultant mixture was stirred at 40° C. for 23 hours. The obtained mixture was cooled down to 23° C., and 30.00 parts of chloroform and 30.00 parts of ion-exchanged water were added thereto. The resultant mixture was stirred and then separated to an organic layer and an aqueous layer. The organic layer was washed with ion-exchanged water until the aqueous layer showed neutral. To the obtained organic layer, 1.2 parts of active carbon was added to stir. The resultant mixture was filtrated and the obtained filtrate was concentrated. The obtained residue was mixed with 10 parts of ethyl acetate and the supernatant solution was removed. The obtained residue was mixed with 10 parts of tert-butyl methyl ether and the supernatant solution was removed.

The obtained residue was dissolved in chloroform, and the obtained solution was concentrated to obtain 1.18 parts of the salt represented by the above-mentioned formula (I-AA-6) in the form of an orange-colored oil, which is called as Salt A4. Purity: 100%, Yield: 29%.

MS (ESI(+) Spectrum): $M^+$ 443.1

MS (ESI(-) Spectrum): $M^-$ 369.0

$^1$H-NMR (dimethylsulfoxide-$d_6$, Internal Standard: tetramethylsilane): δ (ppm) 1.28-2.32 (m, 10H), 2.53 (m, 1H), 2.63 (m, 1H), 2.87-2.94 (m, 2H), 3.20 (m, 1H), 3.90 (m, 1H), 4.53-4.56 (m, 2H), 4.89 (s, 2H), 7.32-7.38 (m, 2H), 7.70-7.90 (m, 12H)

Example 5

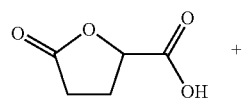

(I-AA-3-a)

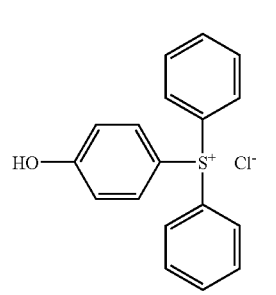

(I-AA-7-b)

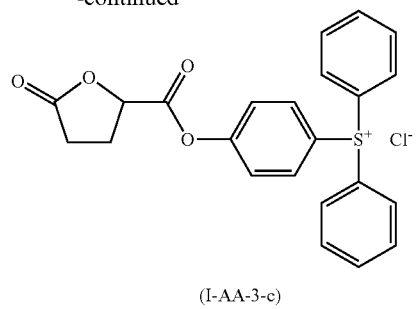

(I-AA-3-c)

A mixture of 22.25 parts of monochlorobenzene, 1.30 parts of a compound represented by the formula (I-AA-3-a) and 3.15 parts of a compound represented by the formula (I-AA-7-b) was stirred at 23° C. for 30 minutes. To the mixture, 0.98 part of sulfuric acid and 14 parts of molecular sieves 3A available from Wako Pure Chemical Industries, Ltd. were added, and the resultant mixture was stirred at 125° C. for 8 hours. The obtained mixture was cooled down to 23° C. and then, concentrated. The obtained residue was mixed with 38.85 parts of chloroform and the resultant mixture was washed three times with 13.00 parts of ion-exchanged water and the obtained organic layer was filtrated and then, concentrated to obtain a compound represented by the formula (I-AA-3-c) in the form of a pale yellow oil.

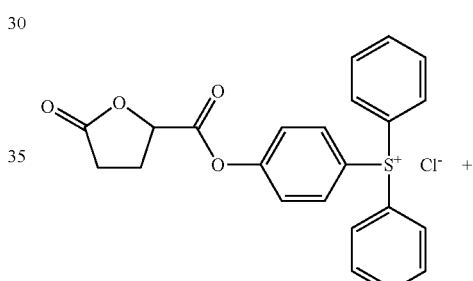

(I-AA-3-c)

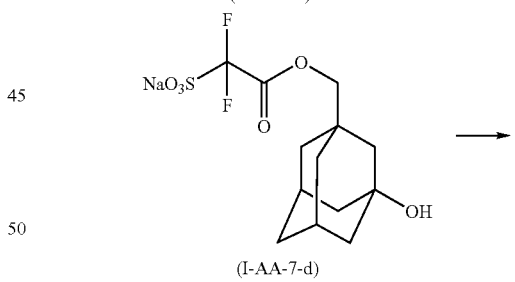

(I-AA-7-d)

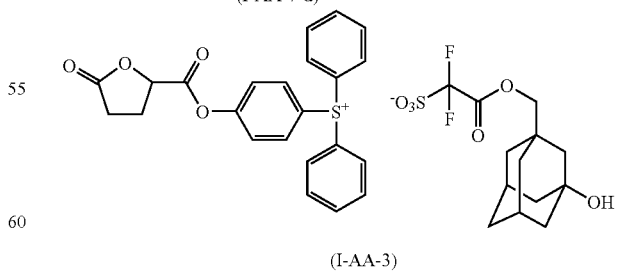

(I-AA-3)

To a solution containing 1.81 parts of the salt represented by the above-mentioned formula (I-AA-7-d), 3.2 parts of chloroform and 2.13 parts of the compound represented by the formula (I-AA-3-c) were added. The resultant mixture was stirred for 15 hours, and then washed with ion-exchanged water. To the obtained organic layer, 1.2 parts of active carbon was added to stir. The resultant mixture was filtrated and the obtained filtrate was concentrated. The obtained residue was mixed with 10 parts of ethyl acetate and the supernatant solution was removed. The obtained residue was mixed with 10 parts of tert-butyl methyl ether and the supernatant solution was removed. The obtained residue was dissolved in chloroform, and the obtained solution was concentrated to obtain 0.62 part of the salt represented by the above-mentioned formula (I-AA-3) in the form of an orange-colored oil, which is called as Salt A5.

Purity: 100%, Yield: 17%.

MS (ESI(+) Spectrum): M$^+$ 391.1

MS (ESI(−) Spectrum): M$^-$ 339.1

$^1$H-NMR (dimethylsulfoxide-d$_6$, Internal Standard: tetramethylsilane): δ (ppm) 1.30-2.25 (m, 16H), 2.39-2.55 (m, 2H), 3.85 (s, 2H), 4.42 (brs, 1H), 4.80-5.05 (m, 1H), 7.32-7.38 (m, 2H), 7.70-7.90 (m, 12H)

Example 6

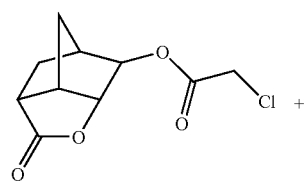

(I-AA-11-a)

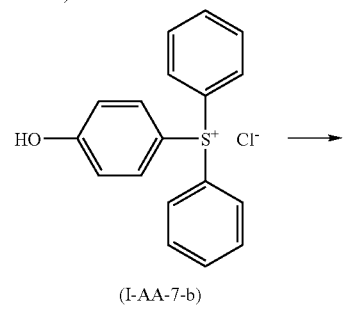

(I-AA-7-b)

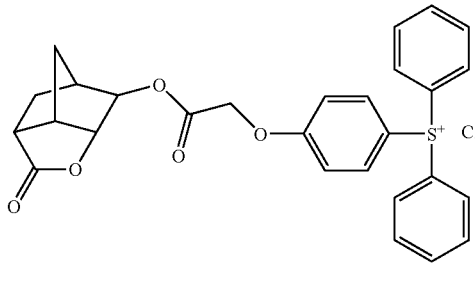

(I-AA-11-c)

A mixture of 14.00 parts of N,N-dimethylformamide and 2.31 parts of a compound represented by the formula (I-AA-11-a) was stirred at 23° C. for 30 minutes. To the mixture, 1.04 parts of potassium carbonate and 0.33 part of potassium iodide were added, and the resultant mixture was stirred at 50° C. for 1 hour. The obtained mixture was cooled down to 40° C. and then a solution prepared by dissolving 3.15 parts of the compound represented by the formula (I-AA-7-b) in 14.00 parts of N,N-dimethylformamide was added dropwise thereto over 1 hour, and the resultant mixture was stirred at 75° C. for 5 hours. The obtained mixture was cooled down to 23° C. and 30.00 parts of chloroform and 30.00 parts of 1N hydrochloric acid were added thereto. The obtained mixture was stirred and separated to an organic layer and an aqueous layer. The obtained organic layer was washed with ion-exchanged water until the aqueous layer showed neutral. To the obtained organic layer, 1.2 parts of active carbon was added to stir. The resultant mixture was filtrated and the obtained filtrate was concentrated. The obtained residue was mixed with 10 parts of ethyl acetate and the supernatant solution was removed. The obtained residue was mixed with 10 parts of tert-butyl methyl ether and the supernatant solution was removed. The obtained residue was dissolved in chloroform, and the obtained solution was concentrated to obtain 2.68 parts of the salt represented by the above-mentioned formula (I-AA-11-c) in the form of an orange-colored oil.

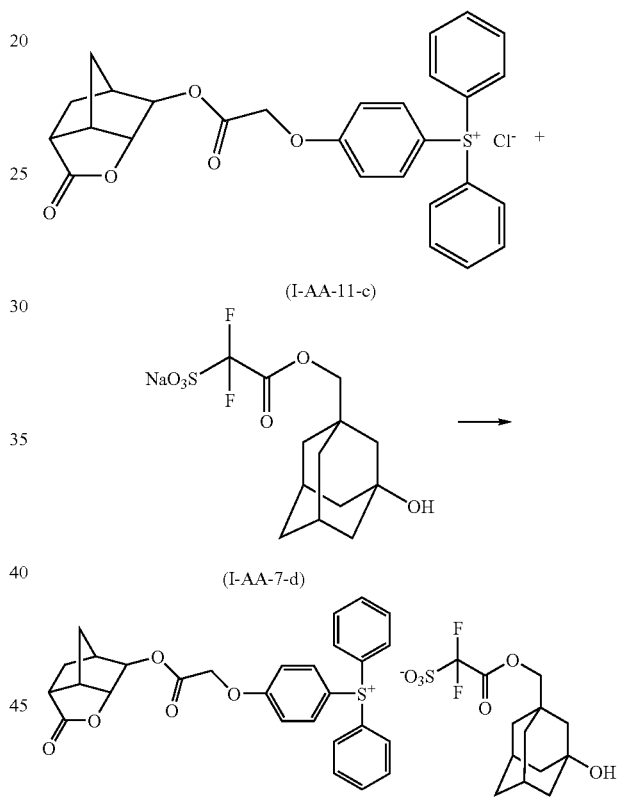

To a solution containing 1.81 parts of the salt represented by the above-mentioned formula (I-AA-7-d), 3.2 parts of chloroform and 2.55 parts of the compound represented by the formula (I-AA-11-c) were added. The resultant mixture was stirred for 15 hours, and then washed with ion-exchanged water. To the obtained organic layer, 1.2 parts of active carbon was added to stir. The resultant mixture was filtrated and the obtained filtrate was concentrated. The obtained residue was mixed with 10 parts of ethyl acetate and the supernatant solution was removed. The obtained residue was mixed with 10 parts of tert-butyl methyl ether and the supernatant solution was removed. The obtained residue was dissolved in chloroform, and the obtained solution was concentrated to obtain 0.73 part of the salt represented by the above-mentioned formula (I-AA-11) in the form of an orange-colored oil, which is called as Salt A6.

Purity: 100%, Yield: 18%.

MS (ESI(+) Spectrum): M+ 473.1

MS (ESI(−) Spectrum): M− 339.1

$^1$H-NMR (dimethylsulfoxide-d$_6$, Internal Standard: tetramethylsilane): δ (ppm) 1.30-2.18 (m, 18H), 2.50-2.65 (m, 2H), 3.25 (m, 1H), 3.85 (s, 2H), 4.42 (brs, 1H), 4.46-4.61 (m, 2H), 5.00 (s, 2H), 7.32-7.37 (m, 2H), 7.70-7.90 (m, 12H)

Example 7

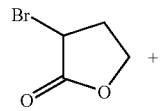

(I-AA-18-a)

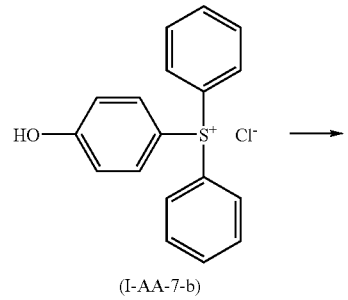

(I-AA-7-b)

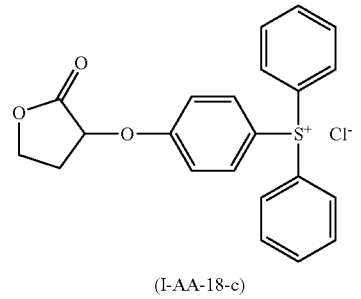

(I-AA-18-c)

A mixture of 14.00 parts of N,N-dimethylformamide and 1.65 parts of a compound represented by the formula (I-AA-18-a) was stirred at 23° C. for 30 minutes. To the mixture, 1.04 parts of potassium carbonate and 0.33 part of potassium iodide were added, and the resultant mixture was stirred at 50° C. for 1 hour. The obtained mixture was cooled down to 40° C. and then a solution prepared by dissolving 3.15 parts of the compound represented by the formula (I-AA-7-b) in 14.00 parts of N,N-dimethylformamide was added dropwise thereto over 1 hour, and the resultant mixture was stirred at 75° C. for 5 hours. The obtained mixture was cooled down to 23° C. and 30.00 parts of chloroform and 30.00 parts of 1N hydrochloric acid were added thereto. The obtained mixture was stirred and separated to an organic layer and an aqueous layer. The obtained organic layer was washed with ion-exchanged water until the aqueous layer showed neutral. To the obtained organic layer, 1.2 parts of active carbon was added to stir. The resultant mixture was filtrated and the obtained filtrate was concentrated. The obtained residue was mixed with 10 parts of ethyl acetate and the supernatant solution was removed. The obtained residue was mixed with 10 parts of tert-butyl methyl ether and the supernatant solution was removed. The obtained residue was dissolved in chloroform, and the obtained solution was concentrated to obtain the salt represented by the above-mentioned formula (I-AA-18-c) in the form of an orange-colored oil.

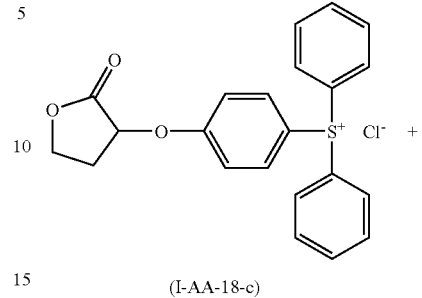

(I-AA-18-c)

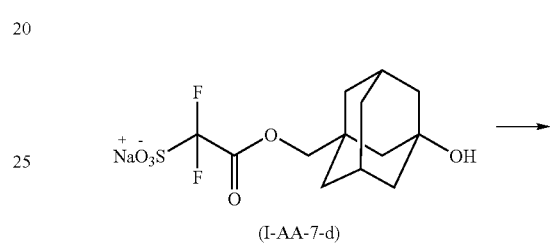

(I-AA-7-d)

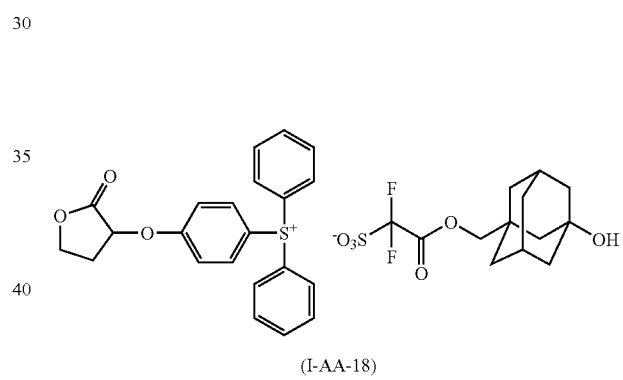

(I-AA-18)

To a solution containing 1.81 parts of the salt represented by the above-mentioned formula (I-AA-7-d), 3.2 parts of chloroform and 1.99 parts of the compound represented by the formula (I-AA-18-c) were added. The resultant mixture was stirred for 15 hours, and then washed with ion-exchanged water. To the obtained organic layer, 1.2 parts of active carbon was added to stir. The resultant mixture was filtrated and the obtained filtrate was concentrated. The obtained residue was mixed with 10 parts of ethyl acetate and the supernatant solution was removed. The obtained residue was mixed with 10 parts of tert-butyl methyl ether and the supernatant solution was removed. The obtained residue was dissolved in chloroform, and the obtained solution was concentrated to obtain 0.48 part of the salt represented by the above-mentioned formula (I-AA-18) in the form of an orange-colored oil, which is called as Salt A7.

Purity: 100%, Yield: 14%.

MS (ESI(+) Spectrum): M+ 363.1

MS (ESI(−) Spectrum): M− 339.1

$^1$H-NMR (dimethylsulfoxide-d$_6$, Internal Standard: tetramethylsilane): δ (ppm) 1.30-2.08 (m, 12H), 2.10 (m, 2H), 2.66-2.91 (m, 2H), 3.86 (s, 2H), 4.22-4.52 (m, 3H), 5.56 (t, 1H), 7.34-7.49 (m, 2H), 7.70-7.90 (m, 12H)

Example 8

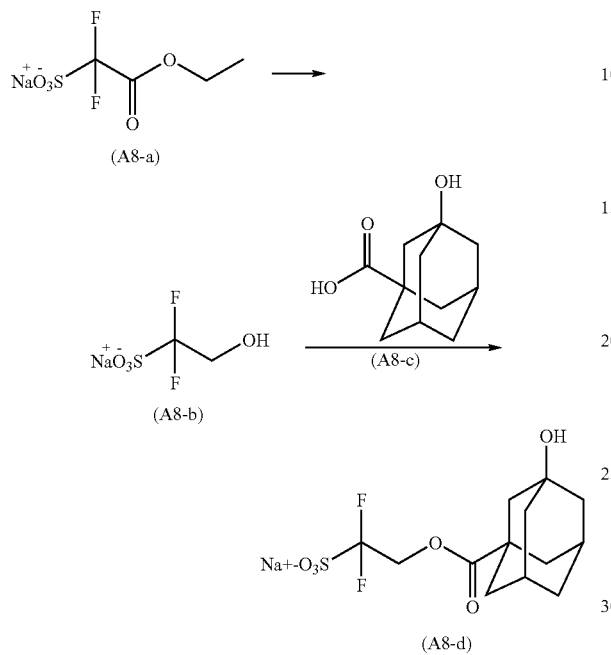

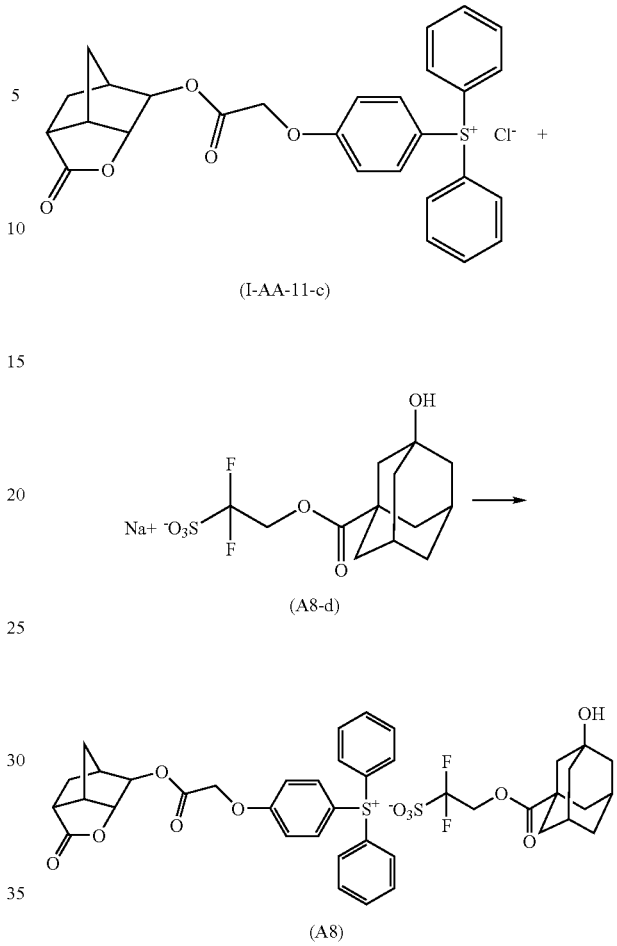

A mixture of 10.4 parts of lithium aluminum hydride and 120 parts of anhydrous tetrahydrofuran was stirred at 23° C. for 30 minutes.

To the mixture, a solution prepared by dissolving 62.2 parts of the compound represented by the above-mentioned formula (A8-a) in 900 parts of anhydrous tetrahydrofuran was added dropwise in an ice bath, and the resultant mixture was stirred at 23° C. for 5 hours. To the obtained mixture, 50.0 parts of ethyl acetate and 50.00 parts of 6N hydrochloric acid were added and then the resultant mixture was stirred and separated to an organic layer and an aqueous layer. The obtained organic layer was concentrated and the obtained residue was purified with silica gel column (silica gel: Merck & Co., Inc., silica gel 60-200 mesh, Developing solvent: chloroform/methanol=5/1) to obtain 84.7 parts of the compound represented by the above-mentioned formula (A8-b). Purity: 60%.

A mixture of 3.51 parts of the compound represented by the above-mentioned formula (A8-c) and 75 parts of anhydrous tetrahydrofuran was stirred at 23° C. for 30 minutes. To the mixture, a solution of 2.89 parts of carbonyldiimidazole in 50 parts of anhydrous tetrahydrofuran was added dropwise at 23° C. and the resultant mixture was stirred at 23° C. for 4 hours. The obtained mixture was added dropwise to a mixture of 6.04 parts of the compound represented by the above-mentioned formula (A8-b) and 50 parts of anhydrous tetrahydrofuran at 54 to 60° C. over 25 minutes. The resultant mixture was heated at 65° C. for 18 hours, and then, cooled and filtrated.

The obtained filtrate was concentrated and the obtained residue was purified with silica gel column (silica gel: Merck & Co., Inc., silica gel 60-200 mesh, Developing solvent: chloroform/methanol=5/1) to obtain 2.99 parts of the salt represented by the above-mentioned formula (A8-d).

To a solution containing 1.21 parts of the salt represented by the above-mentioned formula (A8-d), 4.79 parts of chloroform and 1.70 parts of the compound represented by the formula (I-AA-11-c) were added. The resultant mixture was stirred for 15 hours, and then washed with ion-exchanged water. To the obtained organic layer, 1.0 parts of active carbon was added to stir. The resultant mixture was filtrated and the obtained filtrate was concentrated. The obtained residue was mixed with 10 parts of ethyl acetate and the supernatant solution was removed. The obtained residue was mixed with 10 parts of tert-butyl methyl ether and the supernatant solution was removed. The obtained residue was dissolved in chloroform, and the obtained solution was concentrated to obtain 1.13 parts of the salt represented by the above-mentioned formula (A8) in the form of an orange-colored oil, which is called as Salt A8.

MS (ESI(+) Spectrum): $M^+$ 473.1

MS (ESI(−) Spectrum): $M^-$ 339.1

$^1$H-NMR (dimethylsulfoxide-$d_6$, Internal Standard: tetramethylsilane): δ (ppm) 1.30-2.19 (m, 18H), 2.35 (s, 1H), 2.50-2.65 (m, 2H), 3.25 (m, 1H), 4.46-4.61 (m, 2H), 4.73 (m, 2H), 5.00 (s, 2H), 7.32-7.37 (m, 2H), 7.70-7.90 (m, 12H)

Resin Synthesis Example 1

Monomers used in this Example are following monomers A, B and C.

A 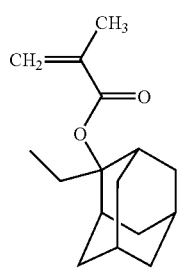

B 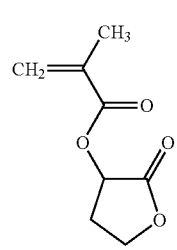

C 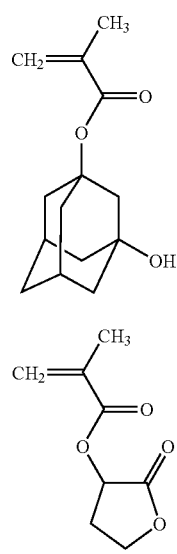

The monomers A, B and C were mixed in a molar ratio of 50/25/25 (monomer A/monomer B/monomer C), and 1,4-dioxane in 1.5 times part based on total parts of all monomers was added to prepare a mixture.

To the mixture, azobisisobutyronitrile as an initiator in a ratio of 1 mol % based on all monomer molar amount and azobis(2,4-dimethylvaleronitrile) as an initiator in a ratio of 3 mol % based on all monomer molar amount were added, and the obtained mixture was heated at 77° C. for about 5 hours. The reaction mixture obtained was poured into a mixture of a large amount of methanol and water to cause precipitation, and this operation was repeated three times for purification. As a result, a resin having a weight-average molecular weight of about 8,000 was obtained in a yield of 60%. The resin had the following structural units. This is called as resin B1.

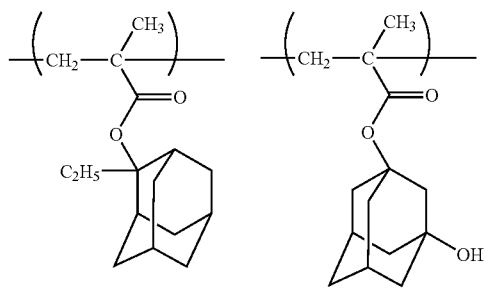

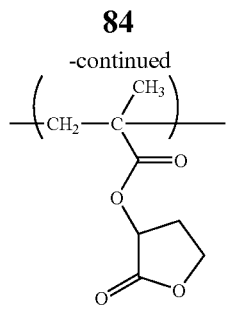

Examples 9 to 16 and Comparative Example 1

Acid Generator

Salt A1, A2, A3, A4, A5, A6, A7, A8, C1

C1:

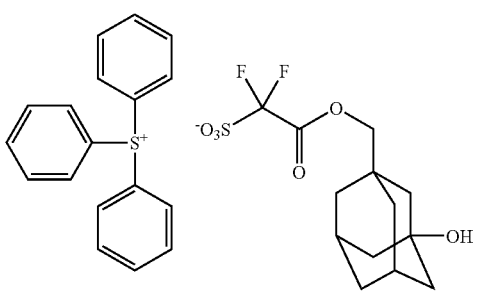

<Resin>
Resin B1
<Quencher>
Q1: 2,6-diisopropylaniline
<Solvent>

| Y1: | propylene glycol monomethyl ether | 265 parts |
|---|---|---|
| | 2-heptanone | 20 parts |
| | propylene glycol monomethyl ether acetate | 20 parts |
| | γ-butyrolactone | 3.5 parts |

The following components were mixed and dissolved, further, filtrated through a fluorine resin filter having pore diameter of 0.2 μm, to prepare photoresist compositions.
Resin (kind and amount are described in Table 1)
Acid generator (kind and amount are described in Table 1)
Quencher (kind and amount are described in Table 1)
Solvent (kind is described in Table 1)

TABLE 1

| Ex. No. | Resin (kind/amount (part)) | Acid generator (kind/amount (part)) | Quencher (kind/amount (part)) | Solvent |
|---|---|---|---|---|
| Ex. 9 | B1/10 | A1/0.7 | Q1/0.065 | Y1 |
| Ex. 10 | B1/10 | A2/0.7 | Q1/0.065 | Y1 |
| Ex. 11 | B1/10 | A3/0.7 | Q1/0.065 | Y1 |
| Ex. 12 | B1/10 | A4/0.7 | Q1/0.065 | Y1 |
| Ex. 13 | B1/10 | A5/0.7 | Q1/0.065 | Y1 |
| Ex. 14 | B1/10 | A6/0.7 | Q1/0.065 | Y1 |
| Ex. 15 | B1/10 | A7/0.7 | Q1/0.065 | Y1 |
| Ex. 16 | B1/10 | A8/0.7 | Q1/0.065 | Y1 |
| Comp. Ex. 1 | B1/10 | C1/0.7 | Q1/0.065 | Y1 |

Silicon wafers were each coated with "ARC-29", which is an organic anti-reflective coating composition available from Nissan Chemical Industries, Ltd., and then baked at 205° C. for 60 seconds, to form a 78 nm-thick organic anti-reflective coating. Each of the photoresist compositions prepared as above was spin-coated over the anti-reflective coating so that the thickness of the resulting film became 85 nm after drying. The silicon wafers thus coated with the respective photoresist compositions were each prebaked on a proximity hotplate at 100° C. for 60 seconds. Using an ArF excimer stepper ("FPA-5000AS3" manufactured by CANON INC., NA=0.75, ⅔ Annular), each wafer thus formed with the respective resist film was subjected to line and space pattern exposure, with the exposure quantity being varied stepwise.

After the exposure, each wafer was subjected to post-exposure baking on a hotplate at 100° C. for 60 seconds and then to paddle development for 15 seconds with an aqueous solution of 2.38 wt % tetramethylammonium hydroxide at 23° C.

Each of a dark field pattern developed on the organic anti-reflective coating substrate after the development was observed with a scanning electron microscope, the results of which are shown in Table 2. The term "dark field pattern", as used herein, means a pattern obtained by exposure and development through a reticle comprising chromium base surface (light-shielding portion) and linear glass layers (light-transmitting portion) formed in the chromium surface and aligned with each other. Thus, the dark field pattern is such that, after exposure and development, resist layer surrounding the line and space pattern remains on substrate.

Effective Sensitivity (ES): It is expressed as the amount of exposure that the line pattern and the space pattern become 1:1 after exposure through 100 nm line and space pattern mask and development.

Pattern Profile: The photoresist pattern at the exposure amount of the effective sensitivity was observed with a scanning electron microscope. When 85 nm line and space pattern was resolved and the cross-section shape of the pattern is rectangle, the pattern profile is good and its evaluation is marked by "○", and when 85 nm line and space pattern was resolved but the cross-section shape of the pattern is taper shape or upper side of the cross-section shape of the pattern is round, the pattern profile is bad and its evaluation is marked by "x".

Mask Error Factor (MEF): The photoresist patterns were obtained using 90 nm, 95 nm and 100 nm line and space pattern masks, respectively at the exposure amount of the effective sensitivity.

The line width of the line patterns were measured respectively, and a graph wherein the mask size is a vertical axis and the line width of the line patterns is a horizontal axis was made and the straight line was drawn. When the slope of the straight line is 2.3 or less, MEF is good and its evaluation is marked by "○", and when the slope of the straight line is more than 2.3, MEF is bad and its evaluation is marked by "x".

Focus margin (DOF): The photoresist patterns were obtained using 85 nm line and space pattern mask at the exposure amount where the line width of the line pattern and the space pattern became 85 nm, with the focal point distance being varied stepwise. Each of patterns were observed and the focal point distances wherein the patterns of which line width was in 85 nm±5% (about 80.8 to 89.3 nm) were obtained were measured and the difference between the maximum value of the focal point distance and the minimum value of the focal point distance was calculated. When the difference is 0.30 μm or more, DOF is good and its evaluation is marked by "○", and when the difference is less than 0.30 μm, DOF is bad and its evaluation is marked by "x".

TABLE 2

| Ex. No. | Pattern Profile | MEF | DOF |
|---|---|---|---|
| Ex. 9 | ○ | ○ | ○ |
| Ex. 10 | ○ | ○ | ○ |
| Ex. 11 | ○ | ○ | ○ |
| Ex. 12 | ○ | ○ | ○ |
| Ex. 13 | ○ | ○ | ○ |
| Ex. 14 | ○ | ○ | ○ |
| EX. 15 | ○ | ○ | ○ |
| Ex. 16 | ○ | ○ | ○ |
| Comp. Ex. 1 | X | X | X |

The salt of the present invention is novel and is useful as an acid generator, and the photoresist composition containing the salt of the present invention provides a photoresist pattern having good pattern profile, good MEF and good DOF, and is especially suitable for ArF excimer laser lithography, KrF excimer laser lithography and ArF immersion lithography.

What is claimed is:
1. A salt represented by the formula (I-AA):

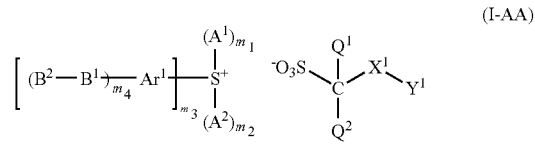

wherein $Q^1$ and $Q^2$ each independently represent a fluorine atom or a C1-C4 perfluoroalkyl group, $X^1$ represents a single bond or —$(CH_2)_k$—, and one or more —$CH_2$— in —$(CH_2)_k$— can be replaced by —O— or —CO— and one or more hydrogen atoms in —$(CH_2)_k$— can be replaced C1-C4 aliphatic hydrocarbon group, and k represents an integer of 1 to 17, $Y^1$ represents a C3-C36 alicyclic hydrocarbon group which can have one or more substituents having no fluorine atom, and one or more —$CH_2$— of which can be replaced by —O— or —CO—, $A^1$ and $A^2$ independently each represents a C1-C20 aliphatic hydrocarbon group, a C3-C20 alicyclic hydrocarbon group or a C6-C20 aromatic hydrocarbon group, or $A^1$ and $A^2$ are bonded each other to form a C3-C20 ring, and one or more hydrogen atoms in the aliphatic hydrocarbon group, the alicyclic hydrocarbon group, the aromatic hydrocarbon group and the ring can be replaced by a hydroxyl group, a C1-C12 alkyl group, a C1-C12 alkoxy group or a C3-C36 alicyclic hydrocarbon group, $Ar^1$ represents a ($m_4$+1)-valent C6-C20 aromatic hydrocarbon group which can have one or more substituents, $B^1$ represents a single bond or C1-C6 alkylene group, and one or more —$CH_2$— in the alkylene group can be replaced by —O— or —CO—, $B^2$ represents a C4-C18 lactone ring group not capable of being eliminated by the action of an acid and one or more hydrogen atoms in the lactone ring group can be replaced by a cyano group, a C1-C20 aliphatic hydrocarbon group or a C3-C20 alicyclic hydrocarbon group, $m_1$ and $m_2$ independently each represents an integer of 0 to 2, $m_3$ represents an integer of 1 to 3, with the proviso that $m_1$ plus $m_2$ plus $m_3$ equals 3, and $m_4$ represents an integer of 1 to 3.

2. The salt according to claim 1, wherein $Y^1$ represents a C3-C36 alicyclic hydrocarbon group in which one or more hydrogen atoms can be replaced by a chlorine atom, a bromine atom, a hydroxyl group, a cyano group, a C2-C7 acyl group, C2-C18 acyloxy group, a C1-C6 alkoxy group, a C2-C7 alkoxycarbonyl group, a C1-C12 aliphatic hydrocarbon group, a C3-C10 alicyclic hydrocarbon group or a C6-C20 aromatic hydrocarbon group, and $Ar^1$ represents a ($m_4$+1)-valent C6-C20 aromatic hydrocarbon group and one or more hydrogen atoms in the aromatic hydrocarbon group can be replaced by a halogen atom, a hydroxyl group, a C1-C12 aliphatic hydrocarbon group, a C3-C10 alicyclic hydrocarbon group, a C2-C4 acyl group or a C1-C6 alkoxy group.

3. The salt according to claim 1, wherein $B^2$ is a group represented by the formula (B2-1a) or (B2-1b):

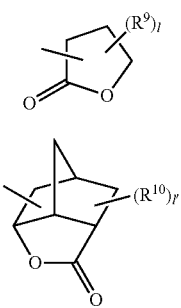

wherein $R^9$ is independently in each occurrence a C1-C20 aliphatic hydrocarbon group or a C3-C20 alicyclic hydrocarbon group, l represents an integer of 0 to 5, $R^{10}$ is independently in each occurrence a cyano group, a C1-C20 aliphatic hydrocarbon group or a C3-C20 alicyclic hydrocarbon group, and l' represents an integer of 0 to 3.

4. The salt according to claim 1, wherein $Ar^1$ is a phenylene group and $m_4$ is 1.

5. The salt according to claim 1, wherein $m_1$, $m_2$ and $m_3$ are 1.

6. The salt according to claim 1, wherein $B^1$ is *—O—CO—, —CO—O—, —O— or *—O—CH$_2$—CO—O— wherein * represents a binding position to $Ar^1$.

7. The salt according to claim 1, wherein $Ar^1$ is a p-phenylene group.

8. A photoresist composition comprising the salt according claim 1 and a resin comprising a structural unit having an acid-labile group and being insoluble or poorly soluble in an aqueous alkali solution but becoming soluable in an aqueous alkali solution by the action of an acid.

9. The photoresist composition according to claim 8, wherein the photoresist composition further contains a basic compound.

10. A process for producing a photoresist pattern comprising the following steps (1) to (5):
   (1) a step of applying the photoresist composition according to claim 8 or 9 on a substrate,
   (2) a step of forming a photoresist film by conducting drying,
   (3) a step of exposing the photoresist film to radiation,
   (4) a step of baking the exposed photoresist film, and
   (5) a step of developing the baked photoresist film with an alkaline developer, thereby forming a photoresist pattern.

* * * * *